(12) United States Patent
Fujimoto et al.

(10) Patent No.: US 9,408,855 B2
(45) Date of Patent: Aug. 9, 2016

(54) THERMORESPONSIVE, BIODEGRADABLE, ELASTOMERIC MATERIAL AND USES THEREFOR

(71) Applicant: University of Pittsburgh—Of the Commonwealth System of Higher Education, Pittsburgh, PA (US)

(72) Inventors: Kazuro Lee Fujimoto, Pittsburgh, PA (US); Jianjun Guan, Dublin, OH (US); Zuwei Ma, Woburn, MA (US); William R. Wagner, Gibsonia, PA (US)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 0 days.

(21) Appl. No.: 14/166,117

(22) Filed: Jan. 28, 2014

(65) Prior Publication Data

US 2014/0213517 A1 Jul. 31, 2014

Related U.S. Application Data

(62) Division of application No. 13/265,067, filed as application No. PCT/US2010/033181 on Apr. 30, 2010, now Pat. No. 8,673,295.

(60) Provisional application No. 61/174,088, filed on Apr. 30, 2009.

(51) Int. Cl.
| | |
|---|---|
| *A61K 31/56* | (2006.01) |
| *A61K 38/18* | (2006.01) |
| *A61K 38/22* | (2006.01) |
| *A61K 38/30* | (2006.01) |
| *A61K 47/32* | (2006.01) |
| *A61K 9/00* | (2006.01) |
| *A61L 27/52* | (2006.01) |
| *A61L 27/58* | (2006.01) |

(52) U.S. Cl.
CPC .............. *A61K 31/56* (2013.01); *A61K 9/0024* (2013.01); *A61K 38/1825* (2013.01); *A61K 38/22* (2013.01); *A61K 38/30* (2013.01); *A61K 47/32* (2013.01); *A61L 27/52* (2013.01); *A61L 27/58* (2013.01)

(58) Field of Classification Search
CPC ....... A61K 31/56; A61K 38/18; A61K 38/22; A61K 38/30; A61K 47/32
USPC .................................................. 424/405, 487
See application file for complete search history.

(56) References Cited

U.S. PATENT DOCUMENTS

| | | | |
|---|---|---|---|
| 5,763,548 A | 6/1998 | Matyjaszewski et al. | |
| 5,789,487 A | 8/1998 | Matyjaszewski et al. | |
| 5,807,937 A | 9/1998 | Matyjaszewski et al. | |
| 6,541,580 B1 | 4/2003 | Matyjaszewski et al. | |
| 7,678,869 B2 | 3/2010 | Matyjaszewski et al. | |
| 2002/0015734 A1* | 2/2002 | Uludag et al. | 424/486 |
| 2005/0154376 A1 | 7/2005 | Riviere et al. | |
| 2008/0096975 A1 | 4/2008 | Guan et al. | |

FOREIGN PATENT DOCUMENTS

WO 2004/014969 * 2/2004

OTHER PUBLICATIONS

Fournier et al. (Macromolecules, Published 2007, pp. 915-920).*
Devin Max Nelson (PhD Dissertation, Controlled Drug Delivery from Biomaterials Used for Cardiac Repair, 2012).*
Langloise et al. (Polymer Degradation and Stability, Published 2002, pp. 411-417).*
Aoki et al., Angiogenesis induced by hepatocyte growth factor in non-infarcted myocardium and infarcted myocardium: up-regulation of essential transcription factor for angiogenesis, ets, Gene Therapy, 2000, pp. 417-427, vol. 7.
Appell, Collagen Injection Therapy for Urinary Incontinence, The Craft of Urologic Surgery, Feb. 1994, pp. 177-182, vol. 21, No. 1.
Bae et al., Polymeric Materials Encyclopedia: vol. 4, F-G, 1996, pp. 2490-2492, CRC Press, Editor Joseph C. Salamone, New York.
Batista et al., Partial Left Ventriculectomy to Treat End-Stage Heart Disease, Ann Thorac Surg, 1997, pp. 634-638, vol. 64.
Bromberg et al., Temperature-responsive gels and thermogelling polymer matrices for protein and peptide delivery, Advanced Drug Delivery Reviews, 1998, pp. 197-221, vol. 31.
Chaudhry et al., Passive Epicardial Containment Prevents Ventricular Remodeling in Heart Failure, Ann Thorac Surg, 2000, pp. 1275-1280, vol. 70.
Christman et al., Fibrin Glue Alone and Skeletal Myoblasts in a Fibrin Scaffold Preserve Cardiac Function after Myocardial Infarction, Tissue Engineering, 2004, pp. 403-409, vol. 10, No. 3/4.
Christman et al., Biomaterials for the Treatment of Myocardial Infarction, Journal of the American College of Cardiology, 2006, p. 907-913, vol. 48.
Cloyd et al., Material properties in unconfined compression of human nucleus pulposus, injectable hyaluronic acid-based based hydrogels and tissue engineering scaffolds, Eur Spine J, 2007, pp. 1892-1898, vol. 16.
Cui et al., New Hydrolysis-Dependent Thermosensitive Polymer for an Injectable Degradable System, Biomacromolecules, 2007, pp. 1280-1286, vol. 8.

(Continued)

*Primary Examiner* — Alma Pipic
(74) *Attorney, Agent, or Firm* — The Webb Law Firm

(57) ABSTRACT

Provided are novel biocompatible copolymers and compositions comprising the copolymers. The copolymers are non-toxic and typically have an LCST below 37° C. Compositions comprising the copolymers can be used for wound treatment, as a cellular growth matrix or niche and for injection into cardiac tissue to repair and mechanically support damaged tissue. The copolymers comprise numerous ester linkages so that the copolymers are erodeable in situ. Degradation products of the copolymers are soluble and non-toxic. The copolymers can be amine-reactive so that they can conjugate with proteins, such as collagen. Active ingredients, such as drugs, can be incorporated into compositions comprising the copolymers.

21 Claims, 36 Drawing Sheets

(56) References Cited

OTHER PUBLICATIONS

Davis et al., Local myocardial insulin-like growth factor 1 (IGF-1) delivery with biotinylated peptide nanofibers improves cell therapy for myocardial infarction, PNAS, May 23, 2006, pp. 8155-8160, vol. 103, No. 21.
Defail et al., Controlled release of bioactive doxorubicin from microspheres embedded within gelatin scaffolds, Journal of Biomedical Materials Research Part A, 2006, pp. 954-962, vol. 79.
Dickey et al., Eutectic Gallium—Indium (EGaIn): A Liquid Metal Alloy for the Formation of Stable Structures in Microchannels at Room Temperature, Advanced Functional Materials, 2008, pp. 1097-1104, vol. 18.
Dor et al., Efficacy of Endoventricular Patch Plasty in Large Postinfarction Akinetic Scar and Severe Left Ventricular Dysfunction: Comparison with a Series of Large Dyskinetic Scars, Journal of Thoracic and Cardiovascular Surgery, 1998, pp. 50-59, vol. 116, No. 1.
Dubois et al., Self-Assembling Peptide Nanofibers and Skeletal Myoblast Transplantation in Infarcted Myocardium, Journal of Biomedical Materials Research Part B: Applied Biomaterials, 2008, pp. 222-228, vol. 87B.
Feil et al., Effect of Comonomer Hydrophilicity and Ionization on the Lower Critical Solution Temperature of N-Isopropylacrylamide Copolymers, Macromolecules, 1993, pp. 2496-2500, vol. 26.
Freyman et al., A quantitative, randomized study evaluating three methods of mesenchymal stem cell delivery following myocardial infarction, European Heart Journal, 2006, pp. 1114-1122, vol. 27.
Fujimoto et al., An Elastic, Biodegradable Cardiac Patch Induces Contractile Smooth Muscle and Improves Cardiac Remodeling and Function in Subacute Myocardial Infarction, Journal of the American College of Cardiology, 2007, pp. 2292-2300, vol. 49, No. 23.
Fujimoto et al., Synthesis, characterization and therapeutic efficacy of a biodegradable, thermoresponsive hydrogel designed for application in chronic infarcted myocardium, Biomaterials, Sep. 2009, pp. 4357-4368, vol. 30, No. 26.
Ghoniem et al., The Evolving Role of Submucosal Injectables for Treating Internal Sphincteric Deficiency, Urologic Nursing, Jun. 1998, pp. 125-128, vol. 18, No. 2.
Gil et al., Stimuli-responsive polymers and their bioconjugates, Progress in Polymer Science, 2004, pp. 1173-1222, vol. 29.
Gnecchi et al., Evidence supporting paracrine hypothesis for Akt-modified mesenchymal stem cell-mediated cardiac protection and functional improvement, The FASEB Journal, Apr. 2006, pp. 661-669, vol. 20.
Goldstein et al., New Insights into Dilated Cardiomyopathy, Cardiology Clinics, Nov. 1998, pp. 623-632, vol. 16, Issue 4.
Guan et al., Protein-Reactive, Thermoresponsive Copolymers with High Flexibility and Biodegradability, Biomacromolecules, 2008, pp. 1283-1292, vol. 9.
Hayakawa et al., Inhibition of Granulation Tissue Cell Apoptosis During the Subacute State of Myocardial Infarction Improves Cardiac Remodeling and Dysfunction at the Chronic Stage, Circulation, 2003, pp. 104-109, vol. 108.
Hao et al., Angiogenic effects of sequential release of VEGF-A165 and PDGF-BB with alginate hydrogels after myocardial infarction, Cardiovascular Research, 2007, pp. 178-185, vol. 75.
Healy et al., Designing Biomaterials to Direct Biological Responses, Annals of the New York Academy of Sciences, 1999, pp. 24-35, vol. 875.
Holmes et al., Structure and Mechanics of Healing Myocardial Infarcts, Annu. Rev. Biomed. Eng., 2005, pp. 223-253, vol. 7.
Hsieh et al., Controlled delivery of PDGF-BB for myocardial protection using injectable self-assembling peptide nanofibers, The Journal of Clinical Investigation, Jan. 2006, pp. 237-248, vol. 116, No. 1.
Huang et al., Injectable Biopolymers Enhance Angiogenesis after Myocardial Infarction, Tissue Engineering, 2005, pp. 1860-1866, vol. 11, No. 11/12.
Iwakura et al., Intramyocardial sustained delivery of basic fibroblast growth factor improves angiogenesis and ventricular function in a rat infarct model, Heart Vessels, 2003, pp. 93-99, vol. 18.
Jeong et al., Thermosensitive sol-gel reversible hydrogels, Advanced Drug Delivery Reviews, 2002, pp. 37-51, vol. 54.
Jiang et al., Injection of a novel synthetic hydrogel preserves left ventricle function after myocardial infarction, Journal of Biomedical Materials Research Part A, 2009, pp. 472-477, vol. 90.
Kanemitsu et al., Insulin-like Growth Factor-1 Enhances the Efficacy of Myoblast Transplantation With Its Multiple Functions in the Chronic Myocardial Infarction Rat Model, Journal of Heart and Lung Transplantation, 2006, pp. 1253-1262, vol. 25.
Kawaguchi et al., Left Ventricular Volume Reduction Surgery: The 4th International Registry Report 2004, J Card Surg, 2005, pp. S5-S11, vol. 20.
Klouda et al., Thermoresponsive hydrogels in biomedical applications—a review, Eur J Pharm Biopharm., Jan. 2008, pp. 34-45, vol. 68, No. 1.
Kobsa et al., Bioengineering Approaches to Controlled Protein Delivery, Pediatric Research, 2008, pp. 513-519, vol. 63, No. 5.
Landa et al., Effect of Injectable Alginate Implant on Cardiac Remodeling and Function After Recent and Old Infarcts in Rat, Circulation, 2008, pp. 1388-1396, vol. 117.
Lee et al., In Situ-Gelling, Erodible N-Isopropylacrylamide Copolymers, Macromolecular Bioscience, 2005, pp. 629-635, vol. 5.
Lee et al., ph-Thermoreversible Hydrogels. I. Synthesis and Swelling Behaviors of the (N-isopropylacrylamide-co-acrylamide-co-2-hydroxyethyl methacrylate) Copolymeric Hydrogels, Journal of Applied Polymer Science, 1999, pp. 221-231, vol. 71.
Liu et al., Thermoresponsive copolymers: from fundamental studies to applications, Colloid Polym Sci, Apr. 18, 2009, p. 627-643, vol. 287.
Lu et al., Functional Improvement of Infarcted Heart by Co-Injection of Embryonic Stem Cells with Temperature-Responsive Chitosan Hydrogel, Tissue Engineering: Part A, 2009, pp. 1437-1447, vol. 15, No. 6.
Magovern, Experimental and Clinical Studies with the Paracor Cardiac Restraint Device, Thoracic and Cardiovascular Surgery, 2005, pp. 364-368, vol. 17.
Matsubayashi et al., Improved Left Ventricular Aneurysm Repair With Bioengineered Vascular Smooth Muscle Grafts, Circulation, 2003, pp. II-219-II-225, vol. 108.
Matsusaki et al., Novel Functional Biodegradable Polymer IV: ph-Sensitive Controlled Release of Fibroblast Growth Factor-2 from a Poly (gamma-glutamic acid)-Sulfonate Matrix for Tissue Engineering, Biomacromolecules, 2005, pp. 3351-3356, vol. 6, No. 6.
Mukherjee et al., Targeted Myocardial Microinjections of a Biocomposite Material Reduces Infarct Expansion in Pigs, Ann Thorac Surg, 2008, pp. 1268-1277, vol. 86.
Oshima et al., Differential Myocardial Infarct Repair with Muscle Stem Cells Compared to Myoblasts, Molecular Therapy, Dec. 2005, pp. 1130-1141, vol. 12, No. 6.
Ota et al., Minimally Invasive Epicardial Injections Using a Novel Semiautonomous Robotic Device, Circulation, 2008, pp. S115-S120, vol. 118.
Patronik et al., A Miniature Mobile Robot for Navigation and Positioning on the Beating Heart, IEEE Trans Robot., 2009, pp. 1109-1124, vol. 25, No. 5.
Peppas et al., Stimuli-sensitive protein delivery systems, J. Drug Del. Sci. Tech., 2006, pp. 11-18, vol. 16, No. 1.
Post et al., Therapeutic angiogenesis in cardiology using protein formulations, Cardiovascular Research, 2001, pp. 522-531, vol. 49.
Qiu et al., Environment-sensitive hydrogels for drug delivery, Advanced Drug Delivery Reviews, 2001, pp. 321-339, vol. 53.
Ray et al., Isolation of vascular smooth muscle cells from a single murine aorta, Methods in Cell Science, 2002, pp. 185-188, vol. 23.
Ruel-Gariepy et al., In situ-forming hydrogels—review of temperature-sensitive systems, European Journal of Pharmaceutics and Biopharmaceutics, 2004, pp. 409-426, vol. 58.
Rzaev et al., Functional copolymers of N-isopropylacrylamide for bioengineering applications, Progress in Polymer Science, 2007, pp. 534-595, vol. 32.

(56) References Cited

OTHER PUBLICATIONS

Sakakibara et al., Toward surgical angiogenesis using slow-released basic fibroblast growth factor, European Journal of Cardio-thoracic Surgery, 2003, pp. 105-112, vol. 24.

Segal et al., Stroke as a complication of cardiac catheterization: Risk factors and clinical features, Neurology, 2001, pp. 975-977, vol. 56.

Shao et al., Effects of Intramyocardial Administration of Slow-Release Basic Fibroblast Growth Factor on Angiogenesis and Ventricular Remodeling in a Rat Infarct Model, Circulation Journal, 2006, pp. 471-477, vol. 70.

Singh et al., Controlled release of recombinant insulin-like growth factor from a novel formulation of polylactide-co-glycolide microparticles, Journal of Controlled Release, 2001, pp. 21-28, vol. 70.

Stile et al., Synthesis and Characterization of Injectable Poly (N-isopropylacrylamide)-Based Hydrogels That Support Tissue Formation in Vitro, Macromolecules, 1999, pp. 7370-7379, vol. 32.

Suleiman et al., Apoptosis and the cardiac action of insulin-like growth factor I, Pharmacology & Therapeutics, 2007, pp. 278-294, vol. 114.

Tabata, Tissue Regeneration Based on Growth Factor Release, Tissue Engineering, 2003, pg. s-5-s-14, vol. 9.

Tabata et al., In vitro sorption and desorption of basic fibroblast growth factor from biodegradable hydrogels, Biomaterials, 1998, pp. 1781-1789, vol. 19.

Takehara et al., Controlled Delivery of Basic Fibroblast Growth Factor Promotes Human Cardiosphere-Derived Cell Engraftment to Enhance Cardiac Repair for Chronic Myocardial Infarction, Journal of American College of Cardiology, 2008, pp. 1858-1865, vol. 52, No. 23.

Tian et al., Physically Cross-Linked Alkylacrylamide Hydrogels: Phase Behavior and Microstructure, Macromolecules, 2004, pp. 9994-10000, vol. 37.

Tsur-Gang et al., The effects of peptide-based modification of alginate on left ventricular remodeling and function after myocardial infarction, Biomaterials, 2009, pp. 189-195, vol. 30.

Vakkalanka et al., Swelling behavior of temperature- and pH-sensitive block terpolymers for drug delivery, Polymer Bulletin, 1996, pp. 221-225, vol. 36.

Vernengo et al., Evaluation of Novel Injectable Hydrogels for Nucleus Pulposus Replacement, Journal of Biomedical Materials Research Part B: Applied Biomaterials, 2008, pp. 64-69, vol. 84.

Vihola et al., Cytotoxicity of thermosensitive polymers poly(N-isopropylacrylamide), poly(N-vinylcaprolactam) and amphiphilically modified poly(N-vinylcaprolactam), Biomaterials, 2005, pp. 3055-3064, vol. 26.

Volklein et al., Modelling of a microelectromechanical thermoelectric cooler, Sensors and Actuators, 1999, pp. 95-101, vol. 75.

Wall et al., Theoretical Impact of the Injection of Material Into the Myocardium: A Finite Element Model Simulation, Circulation, 2006, pp. 2627-2635, vol. 114.

Wang et al., Injectable, rapid gelling and highly flexible hydrogel composites as growth factor and cell carriers, Acta Biomaterialia, 2010, pp. 1978-1991, vol. 6.

Wang et al., Synthesis, characterization and surface modification of low moduli poly(ether carbonate urethane)ureas for soft tissue engineering, Acta Biomaterialia, 2009, pp. 2901-2912, vol. 5.

Wang et al., Novel thermosensitive hydrogel injection inhibits post-infarct ventricle remodelling, European Journal of Heart Failure, 2009, pp. 14-19, vol. 11.

Wu et al., Toward the Development of Partially Biodegradable and Injectable Thermoresponsive Hydrogels for Potential Biomedical Applications, ACS Applied Materials & Interfaces, 2009, pp. 319-327, vol. 1, No. 2.

Yamashita et al., Reperfusion-Activated Akt Kinase Prevents Apoptosis in Transgenic Mouse Hearts Overexpressing Insulin-Like Growth Factor-1, Circulation Research, 2001, pp. 609-614, vol. 88.

Yu et al., Restoration of left ventricular geometry and improvement of left ventricular function in a rodent model of chronic ischemic cardiomyopathy, The Journal of Thoracic and Cardiovascular Surgery, 2009, pp. 180-187, vol. 137, No. 1.

Yu et al., The effect of injected RGD modified alginate on angiogenesis and left ventricular function in a chronic rat infarct model, Biomaterials, 2009, pp. 751-756, vol. 30.

* cited by examiner

THERMORESPONSIVE, BIODEGRADABLE, ELASTOMERIC MATERIAL AND USES THEREFOR

CROSS-REFERENCE TO RELATED APPLICATIONS

This application claims the benefit of U.S. patent application Ser. No. 13/265,067, filed Mar. 1, 2012, which is a U.S. National Stage of International Patent Application No. PCT/US2010/033181, filed Apr. 30, 2010, which claims the benefit of U.S. Provisional Patent Application No. 61/174,088, filed Apr. 30, 2009, each of which is incorporated herein by reference in its entirety.

This invention was made with government support under Grant No. HL069368 awarded by the National Institutes of Health. The government has certain rights in the invention.

BACKGROUND

A thermoresponsive, biodegradable elastomeric material is described herein, along with methods of making the material and uses for the material.

Injectable thermally responsive hydrogels with a lower critical solution temperature (LCST) below body temperature represent promising biomaterials for a variety of biomedical applications, including regional tissue mechanical support as well as drug and cell delivery applications. Generally, the LCST-based phase transition occurs upon warming in situ as a result of entropically-driven dehydration of polymer components, leading to polymer collapse. Various naturally derived and synthetic polymers exhibiting this behavior have been utilized. Natural polymers include elastin-like peptides and polysaccharides derivatives, while notable synthetic polymers include those based on poly(n-isopropyl acrylamide) (PNIPAAm), and amphiphilic block copolymers, often containing poly(ethylene glycol). The structure of PNIPAAm, containing both hydrophilic amide bonds and hydrophobic isopropyl groups, leads to a sharp phase transition at the LCST. Studies suggest that the average number of hydrating water molecules per NIPAAm group falls from 11 to ~2 upon the hydrophobic collapse above the LCST (32° C.)

PNIPAAm based polymers have been extensively studied as injectable biomaterials for tissue regeneration and drug delivery, yet PNIPAAm itself is a non-biodegradable polymer with a constant LCST of approximately 32° C., which prevents ready clearance from the body at physiologic temperature. This limitation of PNIPAAm has provided the motivation for developing biodegradable NIPAAm-based polymers by conjugating the PNIPAAm with natural biodegradable segments such as MMP-susceptible peptide, gelatin, collagen, hyaluronic acid and dextran. However, these may be only partially bioabsorbable since sufficiently long PNIPAAm segments would remain non-soluble following removal of the natural segments.

Copolymers formed from NIPAAm and monomers with degradable side chains comprise another category of NIPAAm-based bioabsorbable, thermally responsive hydrogels. Hydrolytic removal of hydrophobic side chains increases the hydrophilicity of the copolymer, raising the LCST above body temperature and making the polymer backbone soluble. Due to the relative simplicity of the synthetic process, the most investigated biodegradable monomers have been HEMA-based monomers, such as 2-hydroxyethyl methacrylate-polylactide (HEMA-PLA)(Lee, B. H.; et al. *Macromol. Biosci.* 2005, 5, 629-635; and Guan, J., et al. *Biomacromolecules* 2008, 9, 1283-92), 2-hydroxyethyl methacrylate-polycaprolactone (HEMA-PCL) (Wang, T., et al. *Eur. J. Heart Fail* 2009, 11, 14-19 and Wu, D., et al. *ACS Appl. Mater. Interf.* 2009, 2, 312-327) and 2-hydroxyethyl methacrylate-polytrimethylene carbonate (HEMA-PTMC) (Fujimoto, K. L., et al. *Biomaterials* 2009, 30, 4357-4368 and Wang, F., et al. *Acta Biomater.* 2009, 5, 2901). However, the backbone remnant following hydrolysis, HEMA, presents hydroxyethyl side groups ($-CH_2CH_2-OH$), which have a relatively limited effect on remnant polymer hydrophilicity (Cui, Z., et al. *Biomacromolecules* 2007, 8, 1280-1286). In previous studies, such hydrogels have been found to be either partially bioabsorbable (Wu, D., et al. *ACS Appl. Mater. Interf.* 2009, 2, 312-327) or completely bioabsorbable, but have required the inclusion of considerably hydrophilic co-monomers such as acrylic acid (AAc) in the hydrogel synthesis (Fujimoto, K. L.; et al. *Biomaterials* 2009, 30, 4357-4368; Wang, F., et al. *Acta Biomater.* 2009, 5, 2901; and Guan, J., et al. *Biomacromolecules* 2008, 9, 1283-92).

Progressive remodeling of the left ventricular (LV) architecture occurs after myocardial infarction (MI). While initially required for maintenance of cardiac output, this response ultimately leads to LV dysfunction and heart failure in the absence of a recurrent ischemic event. Even with current optimal therapy, mortality in end-stage-heart-failure amounts to 20-50% per year. Heart transplantation is applied as the last therapeutic option for patients with terminal heart-failure, but requests for organ transplantation far outstrip the number of donor organs. Therefore, new therapeutic strategies are urgently needed in order to ameliorate both patient prognosis and quality of life.

Following MI, dilatation of the LV cavity has the effect of increasing LV wall tension, which triggers further dilatation of the LV cavity, and progression down a spiral of adverse cardiac remodeling towards the advanced stages of cardiac failure. To restore wall tension, the endoventricular circular patch plasty technique (the Dor procedure, Dor V, et al. J Thorac Cardiovasc Surg 1998; 116: 50-9 and Kawaguchi A T, et al. J Card Surg 2005; 20: S5-11) and partial left ventriculectomy (the Batista procedure, Batista R J, et al. Ann Thorac Surg 1997; 64: 634-8) have been clinically implemented for severe cardiac dilation and dysfunction many years after an infarction. Employing a similar strategy to limit the remodeling pathway at an earlier stage, epicardial restraint therapies, such as the Acorn Cardiac Support Device (Chaudhry P A, et al. Ann Thorac Surg 2000; 70: 1275-80), and the Paracor device (Magovern J A. Semin Thorac Cardiovasc Surg 2005; 17: 364-8) have been investigated. However, these both apply materials that are non-biodegradable and result in a permanent foreign body encapsulating the epicardium. Using biodegradable and elastic polyester urethane urea, we recently reported that cardiac patch implantation onto a chronic myocardial infarct prevented further cardiac dilatation and improved contraction, while altering LV wall thickness and compliance (Fujimoto K L, et al. J Am Coll Cardiol 2007; 49: 2292-300). Supported by a finite element model simulation (Wall S T, et al. Circulation 2006; 114: 2627-35), another concept in locally treating the failing cardiac wall was proposed where a bulking material is injected into the infarcted left ventricular wall to positively alter cardiac mechanics and result in a potentially beneficial reduction of elevated stresses in the infarcted wall. In this numerical model the local systolic fiber stress distribution was determined in an infarcted LV wall injected with a mechanically passive material. The simulation showed that injection of a volume 4.5% that of the total LV wall volume and with a stiffness (elastic modulus) 20% of the natural LV tissue into the infarct border zone could decrease the fiber stress in the border zone of the infarct by 20% compared to a control simulation in which there was no injection. The mechanical simulation also showed that this attenuation effect on LV wall stress increased with the injection volume and the modulus of the injected material.

Thermally responsive hydrogels are particularly attractive materials for injection therapy following MI since it is possible to inject the necessary fluid volumes from a syringe maintained below body temperature. Upon injection and warming hydrogel mechanical properties are increased, the "holding" of the material at the injection site is facilitated and the mechanical benefit of the injected volume on the cardiac wall is increased.

A need exists for versatile biocompatible polymer compounds that can serve as cell growth substrates, for drug delivery purposes and generally for use in patients, for example for cardiac remodeling.

SUMMARY

Provided herein are compositions comprising thermoresponsive and biodegradable elastomeric materials; namely copolymers and compositions and structures, such as hydrogels, comprising the copolymers. The copolymers remain fluid below physiological temperature (e.g., 37° C. for humans) or at or below room temperature (e.g., 25° C.), solidify (into a hydrogel) at physiological temperature, and degrade and dissolve at physiological conditions in a time-dependent manner, which is important for removal of the hydrogel after an applied surgical or medical procedure. The copolymer and its degradation products typically are biocompatible. According to one embodiment, the copolymer consists essentially of N-isopropylacrylamide (NIPAAm) residues (a residue is a monomer incorporated into a polymer), hydroxyethyl methacrylate (HEMA) residues and methacrylate-polylactide (MAPLA) macromer residues. Alternately, the copolymer consists essentially of N-isopropylacrylamide residues, acrylic acid (AAc) residues, and hydroxyethyl methacrylate-poly(trimethylene carbonate) (HEMAPTMC) macromer residues. Although the size of the copolymers can vary, on one example, the copolymer has an $M_n$ of between 20 kD and 35 kD. In another example, the copolymer has a polydispersity index (PDI, Mw/Mn) of between 1 and 2.

In each copolymer, the ratio of the constituents of the macromer may be varied. For example and without limitation, the polyester macromer is a poly(trimethylene carbonate (TMC)-containing macromer), consisting essentially of or consisting of hydroxyethyl methacrylate residues and varying numbers of trimethylene carbonate units/residues. In another embodiment, the polyester macromer is a methacrylate-polylactide macromer comprising methacrylate residues and varying numbers of lactide residues. Each component contributes to the desired physical properties of the hydrogel to enable an injectable material for delivering drugs or chemicals, encapsulating and transplanting cells, and injecting into empty cavities for wounds or tissue repair. An optional amine-reactive component may be included in the copolymer. The amine-reactive group can be a succinimide group, an oxysuccinimide group or an isocyanate group, such as is produced by incorporation of N-hydroxysuccinimide methacrylate (MANHS) or N-acryloxy succinimide (NAS) monomers into the copolymer. The amine-reactive groups bind to amine-containing compounds including biomolecules such as collagen and/or other bioactive or biocompatible materials or factors. The composition of each component in the hydrogel determines the lower critical solution temperature (LCST) of the hydrogel. At a temperature less than the LCST, the hydrogel flows easily and can be injected into the desired shape. When the temperature is increased above the LCST, the hydrogel solidifies and retains the shape. Once solidified, the hydrogel is highly flexible and relatively strong at physiological temperature.

The polyester component within the macromer introduces the degradability of the copolymer. For complete removal of the copolymer, the copolymer includes hydrolytically-cleavable bonds that results in soluble, non-toxic by-products, even above the LCST of the non-degraded copolymer. Once the copolymer is degraded, the LCST is above physiological temperature, which results in dissolution of the degraded hydrogel and clearance of the degraded components.

In one embodiment, the copolymer has a lower critical solution temperature below 37° C., in another between 10° C. and 34° C. and in another, less than 20° C. According to one embodiment, the copolymer has a lower critical solution temperature above 37° C. after its ester bonds are hydrolyzed.

The polymer may comprise a polyester macromer, for example and without limitation, a polyester macromer comprising methacrylate-polylactide residues. In one embodiment, the ratio of methacrylate and lactide residues in the polyester macromer is from 1:2 (methacrylate:lactide) to 1:8, in another, from 1:1 to 1:10, such as 1:1, 1:2, 1:3, 1:4, 1:5, 1:6, 1:7, 1:8, 1:9, and 1:10. In another non-limiting example, the polyester macromer comprises hydroxyethyl methacrylate and trimethylene carbonate residues. In one embodiment, the ratio of hydroxyethyl methacrylate and trimethylene carbonate residues in the polyester macromer ranges from 1:1 to 1:10, 1:2 to 1:5 or any increment within those ranges, including 1:1, 1:2, 1:3, 1:4, 1:4.2, 1:5, 1:6, 1:7, 1:8, 1:9, and 1:10. Amine-containing biomolecules or other compounds, such as proteins, carbohydrates, glycoproteins, etc. can be conjugated to the copolymer through amine-reactive group, when incorporated into the copolymer. In certain embodiments, collagen, heparin or gelatin are suitable compounds, for instance and without limitation, between 1% wt and 10% wt collagen.

A composition comprising the copolymer described herein also may comprise an aqueous solvent, for example and without limitation, water, saline and phosphate-buffered saline. The composition also can include an active agent, such as, without limitation, one or more of an antiseptic, an antibiotic, an analgesic, an anesthetic, a chemotherapeutic agent, a clotting agent, an anti-inflammatory agent, a metabolite, a cytokine, a chemoattractant, a hormone, a steroid, a protein and a nucleic acid. In one embodiment, where the composition comprises a clotting agent, one example of a clotting agent is desmopressin. In another embodiment, for use (e.g.) in repair of cardiac tissue, the active agents are one or both of bFGF and IGF-1. A biological material, such as a cell or a virus particle may also be incorporated into the composition.

A method is provided of making a thermosensitive copolymer, for example and without limitation, a co-polymer described herein, the method comprising co-polymerizing N-isopropylacrylamide; hydroxyethyl methacrylate; and methacrylate-polylactide (MAPLA) macromer monomers to make a copolymer. In another embodiment, the method comprises co-polymerizing N-isopropylacrylamide, acrylic acid, and hydroxyethyl methacrylate-poly(trimethylene carbonate) macromer monomers. The monomers can be co-polymerized by any useful polymerization method, for example and without limitation by free-radical polymerization or living polymerization methods, such as atom transfer radical polymerization.

According to another embodiment a method of growing cells is provided, comprising introducing cells into any copolymer composition described herein to produce a cell construct and incubating the cell construct under conditions suitable for growth of the cells. The composition can comprise cell growth media to facilitate cell growth within the composition. The cell construct can be administered to a patient (placed in a patient's body at a desired location), such as a human patient. In another embodiment, the composition is administered to a patient without cells, but so that the patient's cells migrate into the composition. The composition can be administered by a injection into the desired site, such as cardiac tissue within the patient. The composition may be injected in or around necrotic tissue in the heart. In one embodiment, the composition is injected approximately 2 weeks after the patient has a myocardial infarction. The composition also may include one or more active agents, such as, without limitation, an antiseptic, an analgesic, an anesthetic and an antibiotic. To facilitate heart repair, or repair of any tissue, or cell growth in general, the composition may comprise, with or without other active agents, one or more of a cytokine, a cell growth or differentiation agent and a metabolite, such as one or both of bFGF and IGF-1.

BRIEF DESCRIPTION OF THE DRAWINGS

FIG. 6.

FIG. 28. (FIG. 28A) Yellow dots outline hydrogel covering the infarct area.

DETAILED DESCRIPTION

Figure 1:
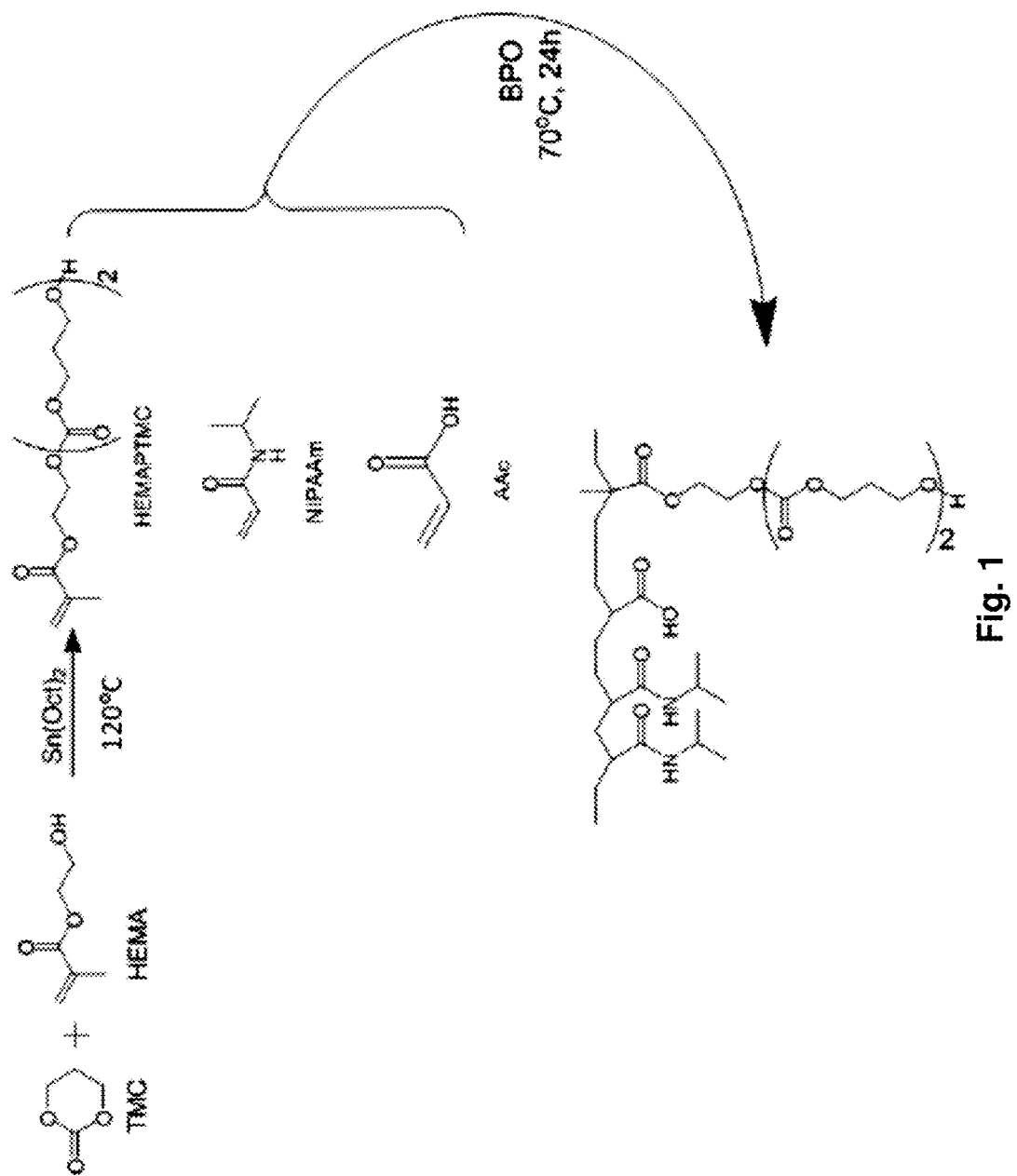
FIG. 1. Synthetic scheme for HEMAPTMC and the copolymer poly(NIPAAm-co-AAc-co-HEMAPTMC)

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases.

As used herein, the terms "comprising," "comprise" or "comprised," and variations thereof, are open ended and do not exclude the presence of other elements not identified. In contrast, the term "consisting of" and variations thereof is intended to be closed, and excludes additional elements in anything but trace amounts. A "copolymer consisting essentially of" two or more monomers or residues means that the copolymer is produced from the stated two or more monomers or contains the stated two or more monomers and is prepared from no other monomers or contains no other residues in any quantity sufficient to substantially affect the LCST properties, the degradation rate in vivo, and tensile strength of the copolymer. Thus, as an example, addition of insignificant or trace amounts of acrylic acid or other monomers to the feed during polymerization, or inclusion of insignificant amounts of acrylic acid or other residues in the copolymer is considered to be within the scope of a copolymer consisting essentially of an N-alkyl acrylamide residue in which the alkyl is one of methyl, ethyl, propyl, isopropyl and cyclopropyl; hydroxyethylmethacrylate; and one or both of a polylactide-methacrylate MAPLA macromer and a HEMA-poly(trimethylene carbonate) macromer), so long as the LCST, degradation rate and tensile strength of the resultant copolymer are not significantly different than that of the same copolymer omitting the acrylic acid residues. The significance of each value is determined independently and in relation to the intended use of the copolymer.

According to embodiments of the compounds and compositions described herein, provided herein are injectable hydrogels that are biodegradable, elastomeric and thermoresponsive and which can easily take the shape of a cavity into which they are injected in advance of phase transition to a solid hydrogel. The copolymers are injectable as a liquid at or below body temperature (about 37° C.) or room temperature (about 25° C.) and are solid at body temperature. These materials are useful for a number of purposes. For example, in treatment of patients, they may be used as an injectable stem cell niche for bone marrow transplants or for other transplantation settings; delivery vehicles for chemotherapy to tissue, such as, for example and without limitation, gut following tumor resections; sealants for pulmonary and neural applications as well as for emergency treatment of wounds. The materials also can find use as bulking agents for cosmetic applications or, even more generally, rheology modifiers. In one embodiment, the compositions are injected in a heart for repair or regeneration of cardiac tissue.

According to certain embodiments, copolymers consist essentially of three types of subunits/residues: 1) N-alkyl acrylamide in which the alkyl is methyl, ethyl, propyl, isopropyl or cyclopropyl, for example N-isopropylacrylamide; 2) HEMA; and 3) a methacrylate-polylactide (MAPLA) macromer. In non-limiting examples, the polylactide-methacrylate macromer has a lactide:methacrylate ratio of at least 1:1 (that is, in reference to FIG. 14, n is 2 or greater), or in the range of 2-3:1. In other non-limiting examples, the feed ratio (the molar ratio of monomers in the polymerization reaction used to prepare the copolymer) of NIPAAm:MAPLA is 80-84:6-10, in one example, the feed ratio of HEMA is 10, such that the feed ratio of NIPAAm:HEMA:MAPLA is 80-84:10:6-10, e.g., the feed ratio of NIPAAm:HEMA:MAPLA is one of 84:10:6, 82:10:8 and 80:10:10.

According to another embodiment, copolymers consist essentially of three types of subunits/residues: 1) N-alkyl acrylamide in which the alkyl is methyl, ethyl, propyl, isopropyl or cyclopropyl, for example N-isopropylacrylamide; 2) acrylic acid; and 3) a hydroxyethyl methacrylate-poly(trimethylene carbonate) (HEMAPTMC) macromer. In non-limiting examples, the HEMA-poly(trimethylene carbonate) macromer has a TMC:HEMA ratio of at least 1:1, or in the range of 2-3:1. In other non-limiting examples, the feed ratio of NIMAAm:AAc:HEMAPTMC is 85-87:3-5:10, for example, 86-87:3-4:10.

The copolymers, compositions and components thereof are preferably biocompatible. By "biocompatible," it is meant that a polymer composition and its normal in vivo degradation products are cytocompatible and are substantially non-toxic and non-carcinogenic in a patient within useful, practical and/or acceptable tolerances. By "cytocompatible," it is meant that the copolymers or compositions are substantially non-toxic to cells and typically and most desirably can sustain a population of cells and/or the polymer compositions, devices, copolymers, and degradation products thereof are not cytotoxic and/or carcinogenic within useful, practical and/or acceptable tolerances. For example, a copolymer composition when placed in a human epithelial cell culture does not adversely affect the viability, growth, adhesion, and number of cells. In one non-limiting example, the co-polymers, compositions, and/or devices are "biocompatible" to the extent they are acceptable for use in a human or veterinary patient according to applicable regulatory standards in a given legal jurisdiction. In another example the biocompatible polymer, when implanted in a patient, does not cause a substantial adverse reaction or substantial harm to cells and tissues in the body, for instance, the polymer composition or device does not cause necrosis or an infection resulting in harm to tissues organs or the organism from the implanted compositions.

As used herein, a "polymer" is a compound formed by the covalent joining of smaller molecules, which are referred to herein as monomers before incorporation into the polymer and residues, or polymer subunits, after incorporated into a polymer. A "copolymer" is a polymer comprising two or more different residues. Non-limiting examples of monomers, in the context of the copolymers described herein, include: acrylic or acrylamide monomers, acrylic N-hydroxysuccinimide ester monomers, N-hydroxysuccinimide methacrylate monomers, N-acryloxy succinimide (NAS) monomers, hydroxyethyl methacrylate, methacrylate, lactide, and trimethylene carbonate. A monomer may be a macromer prepared from smaller monomers, such as a hydroxyethyl methacrylate-polylactide (HEMAPLA) macromer, a hydroxyethyl methacrylate-poly(trimethylene carbonate) (HEMAPTMC) macromer or a methacrylate-polylactide (MAPLA) macromer as described herein.

Monomers (including as a group macromers) can be introduced into the copolymer by radical polymerization or other polymerization methods, such as living polymerization (e.g., atom transfer radical polymerization), or in any useful manner using any suitable initiator, such as benzoyl peroxide. These polymerization processes are well-known in the polymer chemistry field. Radical polymerization is one of the most widely used methods for preparing high polymer from a wide range of vinyl monomers. Although radical polymerization of vinyl monomers is very effective, it does not allow for the direct control of molecular weight, control of chain end functionalities or for the control of the chain architecture, e.g., linear vs. branched or graft polymers. Living polymerization systems have been developed which allow for the control of molecular weight, end group functionality, and architecture. ATRP is a type of controlled radical polymerization or living radical polymerization. (see, e.g., U.S. Pat. Nos. 5,763,548, 5,807,937, 5,789,487, 6,541,580, and 7,678, 869). Controlled radical polymerization methods facilitate production of precise polymer, copolymer and block copolymer structures, such as the A-B-A structures described below.

As used herein, an acrylic monomer has the general structure (CH2=CH—C(O)—R), and, when polymerized, forms the general polymer structure having an alkylene backbone (C—C—C—C—C) and the overall structure: C—(—C(C(O)R)—C—)$_n$—C(C(O)R)—C in which each instance of R can be the same, or in the case of a copolymer, independently different:

Polyester polymer backbones are polymer backbones containing two or more ester groups. A polyester linkage has an average of more than one ester units (—C(O)O—), as opposed to an ester linkage that has one ester unit. An example is a methacrylate-polylactide macromer as described herein. Another example is a HEMA-poly(trimethylene carbonate) macromer. Other examples of residues that comprise ester linkages include, without limitation, caprolactones, glycolides and a trimethylene carbonate residues.

Polyester macromers are compounds containing on the average one or more, and preferably two or more ester linkages. In the context of macromer and polymer preparations, unless otherwise indicated, the number of residues indicated as being present in a given polymer or macromer is an average number and is not to be construed as an absolute number. Thus, as a non-limiting example, in the context of HEMA-PLA macromers, the numbers 2.1, 3.9 and 7.0 refer to an estimated average number of —C(O)—C(CH$_3$)—O— residues present in the macromers in the macromer composition, and, when incorporated into a copolymer, the average number of —C(O)—C(CH$_3$)—O— residues present in the incorporated polyester macromer residues. The average number of residues may be determined by any method, for example and without limitation, by 1H-NMR, as in the examples, below.

In describing ratios of respective monomers for any given copolymer, it is convenient to refer to feed ratios of the monomers in respect to the polymerization method used to produce the copolymer, for example and as used herein, in reference to the radical polymerization methods used to prepare the copolymers. This is especially so when considering that the products of the polymerization process are polydisperse and are often random in their composition. The feed ratios typically closely represent the ratios of monomer residues in the copolymer, but typically do not exactly match because certain monomers incorporate more efficiently than others in any given copolymer composition. The actual ratios of monomer residues typically vary less than 10%, and often less than 5% of the feed ratios. As an example, in Table 1, the feed ratio of 86/4/10 results in an actual composition of 88.3/3.3/8.4, a less than 3% difference in composition.

In another embodiment of the copolymer compositions described herein, the poly(NIPAAm-co-AAc-co-HEMAPTMC) or poly(NIPAAm-co-HEMA-co-MAPLA) copolymers, either optionally comprising an amine-reactive component or group, are incorporated into a block copolymer with a hydrophilic polymer, such as a polyether, which is exemplified by polyethylene glycol (PEG). In one example, the block copolymer compositions have the structure A-B-A where A is poly(NIPAAm-co-AAc-co-HEMAPTMC) or poly(NIPAAm-co-HEMA-co-MAPLA) and B is a polyethylene glycol block having, for example, an average molecular weight of from between 500D and 25 kD, for instance between 1 kD and 20 l(D. The "A" blocks can be added by any useful method, for instance, they can be synthesized by any method and attached to the B block by any useful chemistry. In one embodiment, the A blocks are polymerized from the B block. The terminal portions of the B block can be modified to act as intitiators for a polymerization reaction. As described in the Examples below, the ends of a PEG block can be modified to act as an ATRP initiator, by addition of a suitable halide-containing group, for example by reacting PEG with a-bromoisobutyryl bromide. By using controlled radfical polymerization processes, precise block copolymers can be prepared with low polydispersity indices (PDI), such as PDI<2.

Lower critical solution temperature (LCST) refers to the temperature below which the constituents of the hydrogel are soluble in water and above which the constituents are insoluble. When the LCST is reached, the polymer constituents in an aqueous solution will aggregate to form hydrogel (a solid, for purposes herein). The LCST can be determined by measuring the change in transmittance with a UV-Vis spectrometer as a function of temperature (Advanced Drug Delivery Reviews (1998), 31: 197-221 and Annals N.Y. of Science, 1999, 875(1):24-35). LCST also can be determined by any other useful method—for example and without limitation by Differential Scanning calorimetry (DSC). DSC is used to measure LCST in the examples below.

One unique aspect of the polymers described herein is that the LCST of these polymers is preferably less than 37° C., and may be less than 20° C., for example, between 10° C. and about 37° C., for instance between 10° C. and 25° C., so that the polymer can be distributed through the marketplace, stored and administered to a patient as a liquid at ambient temperatures (or, if necessary, maintained at a cool temperature with an ice-pack, refrigerator or other cooling device), and the polymer gels as it warms past its LCST. Many polymers suitable for administration to patients require mixing of monomers immediately prior to use, which is undesirable for many reasons. For instance, it is impractical to ask doctors, nurses or technicians to mix monomers as they need the polymer. Further, monomers can have varying degrees of toxicity. The copolymers described herein do not require conducting a chemical reaction at the site of use and the copolymers can be washed free of monomer contamination prior to distribution in the marketplace. Lastly, the release of a portion of the aqueous phase during phase transition can facilitate local drug delivery in the excluded aqueous phase.

Another desirable physical quality of the polymers described herein is that, when ester linkages in the backbone are hydrolyzed (for instance over time in situ in a living system, such as a human patient), the released copolymer fragments have an LCST above 37° C., so that they are soluble (and as an additional benefit, non-toxic), facilitating safe degradation and clearance of the polymer over time in a living system such as a human body.

In one embodiment, the copolymer comprises an acrylic residue having an amine-reactive group. The copolymer may be reacted with amine-containing compositions, such as compositions or molecules comprising amine groups, for example and without limitation, collagen; fibrin, gelatin and heparin.

In one non-limiting example in which the copolymer comprises a macromer comprising methacrylate and lactide residues, the ratio of methacrylate and lactide residues in the polyester macromer is from 1:1 to 1:10, such as 1:1, 1:2, 1:3, 1:4, 1:5, 1:6, 1:7, 1:8, 1:9, and 1:10. In another non-limiting embodiment, the ratio of methacrylate to lactide residues in the polyester macromer is from 1:2 to 1:8. In another non-limiting example in which the copolymer comprises a macromer comprising hydroxyethyl methacrylate and trimethylene carbonate residues, the ratio of hydroxyethyl methacrylate to trimethylene carbonate residues in the polyester macromer ranges from 1:1 to 1:10, 1:2 to 1:5 or any increment within those ranges, including 1:1, 1:2, 1:3, 1:4, 1:4.2, 1:5, 1:6, 1:7, 1:8, 1:9, and 1:10. In one embodiment of the copolymer useful in humans or animals, the copolymer has a lower critical solution temperature below 37° C. For veterinary applications, the LCST can be slightly higher as the core body temperature of certain animals (e.g., cats, dogs, horses, cows, sheep and goats) is in the range of 38° C.-39° C. In another embodiment, the copolymer has a lower critical solution temperature above 37° C. after its backbone ester linkages are hydrolyzed (substantially hydrolyzed, as with treatment of the polymer with NaOH, as described herein).

Amine-reactive groups are groups that react with amine residues, such as Lys residues of proteins, to form a covalent linkage. Non-limiting examples of amine-reactive groups are succinimide, oxysuccinimide or isocyanate groups. Non-limiting examples of useful acrylic monomers include, NHS, N-acryloxysuccinimide ester, and N-hydroxysuccinimide methacrylate (MANHS).

In medical or veterinary uses, the copolymers and compositions comprising the copolymers may serve as adhesives or fillers. They may be applied to wounds or into body cavities or used as a tissue packing to apply compression. As such, embodiments of the copolymer solutions described herein may be applied to wounds and, in one embodiment covered, optionally with a warming compress or "heat pack" as are available commercially to ensure that the copolymer is maintained at a temperature above its LCST and thus remains gelled when in contact with any cooler areas of the body, typically the skin. As a hydrogel, embodiments of the copolymers disclosed herein may be contained in a composition comprising the copolymer and an aqueous solution that does not interfere substantially with the LCST and polymer structure in its intended use. For instance, the composition may comprise any aqueous solvent, optionally pharmaceutically acceptable, including, without limitation, water, PBS, Saline, etc. As used herein, and "aqueous solvent", is an aqueous solution compatible with the copolymer which can be absorbed into the copolymer matrix. The composition also may comprise an active agent, biological or drug, such as, without limitation: antibiotics, clotting agents (without limitation, an antifibrinolytic, such as desmopressin/DDVAP), analgesics, anesthetics, antiseptics, anti-inflammatory agents, chemotherapeutic agents, metabolites, rheology modifiers, cytokines, chemoattractants, hormones, steroids, proteins (including enzymes), nucleic acids, cells, virus particles, nucleic acids, biomatrices or precursors thereof, or a foaming agent. In one embodiment, the composition comprises stem cells (such as adipose-derived stem cells) or other progenitor cells so that the composition is useful as a biodegradable tissue engineering scaffold. The composition, even without cells, is useful as a cell growth niche or scaffolding into which cells such as native stem/progenitor cells can migrate in situ. In such an embodiment, chemokines, cellular growth agents and cellular differentiation agents can be included within the composition to attract cells into the composition and promote cellular growth and differentiation when placed in situ.

According to one embodiment, in its application to wound treatment, a clotting agent such as desmopressin may be included in a polymer composition. An appropriate, e.g., pharmaceutically acceptable, foaming agent as are well-known in the relevant arts also may be included for the purpose of creating compression in a wound, whether exposed to a body surface in the case of (for example) puncture wounds or bullet wounds, or internal wounds, in which case, the polymer can be injected into or near a site of internal bleeding. As such, the composition can find use in many situations, ranging from home use to stabilization of bleeding or massively bleeding patients in emergency and battlefield situations. The copolymer also can be used during surgical procedures to apply compression and otherwise secure a site of injury, such as a portion of a patient's intestine, nasal passage or sinus cavity where a tumor or polyp has been removed or after other surgeries. The benefits of such a reversibly-gelling copolymer composition is that the composition can be removed simply by cooling, for example and without limitation, by flushing with cool (lower than the copolymer's LCST) flushing solution, such as water, saline or phosphate-buffered saline. Thus, while a wound and bleeding in a patient can be stabilized by application of the polymer, the polymer can be selectively eroded in an emergency room or during surgery simply by flushing with a cool (for example and without limitation, 0° C. to 30° C.) saline solution.

In a further embodiment, the composition serves as a cell growth medium. According to one embodiment, cells are introduced into a composition comprising a copolymer as described herein to produce a cell construct. The cell construct is incubated under conditions suitable for growth of the cells. That is, the cell construct can be placed in an incubator or into a patient so that the cells are maintained under adequate environmental conditions to permit the cells to survive, proliferate, differentiate and/or express certain products. "Cell growth" means that the cells survive and preferably, though not exclusively, divide and multiply. The composition may comprise cell growth media, which typically provides necessary nutrients and environmental conditions for cell growth. The cells may be introduced and incubated under conditions suitable for cell growth by introducing the composition into a patient and allowing native cells, such as stem cells to migrate into the composition. The composition can be administered by injecting the composition into the region requiring cellular growth or remodeling, such as a region of damaged tissue.

In one non-limiting example, the damaged tissue is within the cardiac wall caused by a myocardial infarction and the composition is injected into the cardiac wall. In one variation of that embodiment, cytokines, chemoattractants, nutrients and/or cell differentiation factors, such as one or both of bFGF and IGF-1, are included in the composition. The composition may also contain one or more of an antiseptic, an analgesic, an anesthetic and an antibiotic (for example, for selection of the cells or to prevent bacterial growth in the composition). To facilitate cell growth, in one non-limiting embodiment, the copolymer is conjugated with collagen, for example between 0% and 10% by weight of the copolymer of collagen.

A current broadly pursued approach to treating ischemic cardiomyopathy is cellular transplantation into the infarct or border zone region to improve regional and global pump function. Cells such as skeletal myoblasts, bone marrow stromal cells, endothelial precursor cells and embryonic stem cells have been injected into injured myocardium. These studies report mixed results, with modest attenuation of progressive loss of ventricular function primarily observed in terms of maintaining or increasing LV wall thickness and fractional shortening. The mechanism behind these beneficial results is controversial, although several have suggested that the transplanted cells led to regeneration of contractile myocardial tissue. Increasingly, however, it is believed that the positive results are derived from cell-associated angiogenic effects or cytokine-mediated reduction in apoptosis rather than myocardial regeneration by the transplanted cells. In 2006, a report by Wall et al. argued that the positive results of these cell therapy studies might simply be attributable to the mechanical effects associated with the injection of fluid volume (cells and delivery vehicle) into the LV wall (Wall S T, et al. Circulation 2006; 114: 2627-35. PMID: 17130342). The injected volume would change the LV geometry and thus modify the mechanics inside the LV wall, leading to a reduction of elevated local wall stresses in the infarct border zone and preventing the pathological remodeling in the post-infarct heart. This hypothesis was supported with a finite element analysis that modeled the local systolic fiber stress distribution in an infarcted LV wall injected with a mechanically passive material. The simulation showed that injection of a volume 4.5% that of the total LV wall volume and a stiffness (elastic modulus) 20% of the natural LV tissue into the infarct border zone could decrease the fiber stress by 20% compared to a control simulation in which there was no injection. The mechanical simulation also showed that this attenuating effect on LV wall stress increased with the injection volume and modulus of the injected material. This report thus provides the basis for the local treatment of the failing cardiac wall with biomaterial-based injection therapy. The stress reduction potential of the injected material is of great relevance since in a dyskinetic transmural infarct, the elevated stresses in the infarct border zone region are thought to contribute to pathological remodeling in the post-infarct heart (Wall S T, et al. Circulation 2006; 114: 2627-35. PMID: 17130342). Reducing these stresses may in turn minimize stress-induced apoptosis and border zone expansion, reducing further remodeling and preventing progression to congestive heart failure.

Both naturally derived and synthetic materials, including alginate, fibrin, alginate-fibrin composites, collagen, chitosan, self-assembling peptides, self-assembling polymers, and thermoresponsive dextran-poly(N-isopropylacrylamide) (PNIPAAm) composites, have recently been utilized for cardiac wall injection therapy in animal models with reported benefits in terms of attenuated decrease in wall thickness and infarct expansion in most cases, and in a few cases improved LV functions (Landa N, et al. Circulation 2008; 117:1388-96. PMID: 18316487 and Lu W N, et al. Tissue Eng 2009; 15:1437-47. PMID: 19061432). Alginate has been shown to have a beneficial effect in terms of attenuating the decrease in wall thickness and infarct expansion, but recent reports injecting adhesion peptide modified alginate demonstrate no clear benefit of such modification (Tsur-Gang O, et al. Biomaterials 2009; 30:189-95. PMID: 18849071 and Yu J, et al. Biomaterials 2009; 30:751-6. PMID: 19010528). Self-assembling peptides carrying specific growth factors have been reported to have positive effects on the cardiac wall remodeling process and have also been reported as vehicles for the transplantation of cardiomyocytes into the cardiac wall (Davis M E, et al. Proc Natl Acad Sci 2006; 103:8155-60. PMCID: PMC1472445). Regarding thermoresponsive polymers, a recent report showed that injection of a dextran-poly (NIPAAm) composite 4 days following MI in a rabbit model prevented adverse cardiac remodeling and dysfunction 30 days following treatment (Wang T, et al. Eur J Heart Fail 2009; 11:14-9. PMID: 19147452).

In considering all of the biomaterials that have been utilized in these early investigations of cardiac injection therapy, it is encouraging that some positive benefits have been observed in the animal models studied. However, the materials investigated to date have not been optimal for the cardiac injection application and that most investigators have utilized "off the shelf" materials (alginate, fibrin, collagen, chitosan) or synthetic hydrogels that do not display the degradation or mechanical profile that would be most desirable for this setting. Only short term effects have been reported in the literature, perhaps since the injected materials are rarely detectable in vivo after 6 wk. Although mechanical properties of the injection material have been shown to be important in mechanical modeling (Wall S T, et al. Circulation 2006; 114: 2627-35. PMID: 17130342), these properties have notably not been characterized and discussed in the early reports where cardiac injection therapy has been investigated. In terms of the animal models that have been evaluated, in most reports LV injections were made within 1 wk of infarction, in the acute, necrotic phase. Waiting longer, even to the point of 2 wk post-MI would have greater relevance, since this time would more closely correspond to the beginning of the fibrotic phase of remodeling, after the necrotic phase (Holmes J W, et al. Annu Rev Biomed Eng 2005; 7: 223-53. PMID: 16004571). Such a time lag may better represent infarcts that would be encountered in patients with sub-acute MI, where the patient may not present clinically until substantial wall remodeling has already occurred (Goldstein S, et al. Cardiol Clin 1998; 16: 623-32. PMID: 9891592).

In the example of infarcted myocardium, in addition to the mechanical benefits associated with injections of the copolymer compositions described herein into the infarcted myocardium, the inclusion of bioactive growth factors in the delivered material for controlled temporal release offers another mechanism by which injection therapy might lead to more functional LV remodeling. Many growth factors such as basic fibroblast growth factor (bFGF), platelet derived growth factor (PDGF), hepatocyte growth factor (HGF), vascular endothelial growth factor (VEGF) and others have been injected into the myocardium following infarction and have elicited improvements in cardiac angiogenesis, ejection fraction, and cellular activity in the form of mitogenesis and motogenesis (Post M J, et al. Cardiol Res 2001; 49:522-531. PMID: 11166265; Aoki M, et al. Gene Therapy 2000; 7:417-27. PMID: 10694824; and Hao X, et al. Cardiovasc Res 2007; 75:178-85. PMID: 17481597). Injection of fluid concentrated with growth factors has been shown to have the same capacity to significantly improve cardiac function as injection of stem cells (Gnecchi M, et al. FASEB J 2006; 20:661-9. PMID: 16581974). Delivering multiple growth factors has also been shown to have advantages over the presentation of a single factor. For example, cardiac injection of an alginate material designed to release VEGF followed by PDGF showed increased alpha smooth muscle cell vessel density than the delivery of either growth factor alone (Hao X, et al. Cardiovasc Res 2007; 75:178-85. PMID: 17481597). Bimodal delivery systems may seek to mimic the native kinetics of growth factor delivery wherein the stimulation and development of one system prior to another may be beneficial—in the example mentioned the development first of a primary vascular network from endothelial cells provided a foundation for recruiting smooth muscle cells to mature and stabilize that network.

Two particularly important growth factors studied in the context of cardiac remodeling have been bFGF and insulin-like growth factor-1 (IGF-1). IGF-1 has been shown to have significant cardioprotective, inotropic, and regenerative capabilities and to be a potent recruiting factor for stem cells (Suleiman M S, et al. Pharmacol Ther 2007; 114:278-94. PMID: 17499363). IGF-1 also leads to increased Akt signaling in cells which can lead to production of other growth factors including VEGF and angiopoietin-2 (Yamashita K, et al. Circ Res 2001; 88:609-14. PMID: 11282895). Local IGF-1 delivery to injured myocardium has been linked to decreased apoptosis, increased cell growth, and improved systolic function (Davis M E, et al. Proc Natl Acad Sci 2006; 103:8155-60. PMCID: PMC1472445). As such, controlled IGF-1 delivery may be useful to improve heart function simultaneously with injected material. A growth factor with effects complementing IGF-1 is bFGF. This potent angiogenic factor strongly increases both endothelial and smooth muscle cell proliferation, and has been linked to increased cardiomyocyte mitotic activity (Post M J, et al. Cardiol Res 2001; 49:522-531. PMID: 11166265). Increased regional blood flow in the infarcted heart has been shown as long as 6 months after a single intramyocardial injection of bFGF. Importantly, from a functional standpoint, left ventricular ejection fraction has been increased in infarcted hearts supplied with bFGF (Takehara N, et al. J Am Coll Cardiol 2008; 52:1858-65. PMID: 19038683). Due to the short half life of bFGF in vivo, controlled release from biomaterial carriers has been shown to be an appropriate delivery method to increase cardiac regeneration (Shao Z Q, et al. Circ J 2006; 70:471-7. PMID: 16565567 and Sakakibara Y, et al. Eur J Cardiothorac Surg 2003; 24:105-11. PMID: 12853053). Using a bimodal delivery system of bFGF followed by IGF-1 may provide a vascular network to which stem cells can be recruited followed by increased proliferation with an improved local vascular network.

Compositions comprising a copolymer described herein can be distributed for use in any suitable vessel. In one instance, the composition is packaged in a sealed container, from which the composition can be poured, squeezed or otherwise decanted, for example and without limitation, by use of a syringe. The vessel can be a bag, such as an IV bag. In another embodiment, the composition can be distributed in a syringe for immediate dispensation into a wound or body cavity/location. A syringe can be fitted with any type of needle, tip, tube, balloon device or other useful fitting for facilitating accurate placement of the solution in or around a desired delivery site, for example and without limitation, for delivery into the large intestine of a patient after removal of a tumor. In another embodiment, the composition and a pharmaceutically acceptable solvent is stored within a syringe at or below 4° C. and the syringe is fitted with a needle gauge sufficient to allow for injection without increased pressure but also prohibit back flow of the solution into the syringe after injection, such as, without limitation, a 16 through 23 G (gauge) needle, and in certain embodiments an 18G or 20G needle. As described below and in the Examples, a robotic injection device can be used to deliver any of the compositions described herein to the heart or other organs or tissue. Thus, methods of use embodying the above-described uses for a copolymer described herein and compositions comprising the copolymer are contemplated and embraced as part of the present invention.

In the context of myocardial infarction, although myocardial injection therapy is currently dominated by transcatheter endocardial approaches, direct epicardial injection offers potential advantages such as easy detection of target myocardial infarct lesions, decreased likelihood of cerebrovascular complications (Segal A Z, et al. Neurology 2001; 56:975-977. PMID: 11294941), and superior site specific efficacy (Freyman T, et al. Eur Heart J 2006; 27:1114-1122. PMID: 16510464). Particularly with gel materials, the risk of backflow and embolization from an endocardial injection site is a serious concern. To date, a major limitation of direct epicardial injection is the lack of dedicated minimally invasive access technology, generally causing it to be performed only in conjunction with other procedures using sternotomy or thoracotomy, both of which have high associated morbidity. In addition, the instrumentation used in most reported applications does not readily accommodate the motion of the beating heart, and therefore does not facilitate precise placement and depth of injections. A dedicated technology for precise interaction with the heart from within the intrapericardial space that balances treatment efficacy and minimal invasiveness is likely to provide a future clinical benefit for the hydrogel injection therapy proposed here and for myocardial injection-based therapies in general. To address this need, we have developed a novel miniature robotic device (HeartLander, see, e.g., US Patent Publication No. 20050154376, incorporated herein by reference in its entirety) that navigates over the epicardial surface to perform minimally invasive myocardial injections on the beating heart through a subxiphoid approach. We have achieved such injections in vivo in a porcine model (Ota T, et al. Circulation 2008; 118:S115-S120. doi:10.1161/CIRCULATIONAHA.107.756049), demonstrating positioning accuracy of 1.7±1.0 mm in applying multi-target injection patterns (Patronik N A, et al. IEEE Transactions on Robotics 2009; 25(5):1109-1124. doi: 10.1109/TRO.2009.2027375).

In another use, a composition described herein can be used for cosmetic purposes, such as for a rheology modifier. Ingredients, including without limitation colorants, fragrances, flavors, and other ingredients listed herein, including active agents, may be included in the composition.

The following examples are provided for illustration purposes and are not intended to limit the scope of the present invention.

EXAMPLES

A hydrogel possessing thermoresponsive behavior coupled with robust mechanical properties suitable for soft tissue engineering is of great interest. Such a thermoresponsive scaffold could readily encapsulate and deliver cells for subsequent mechanical training in vivo or in vitro. Described herein and in the examples below is a family of injectable and flexible hydrogel composites based on thermosensitive copolymers, optionally conjugated with collagen. The compositions find use in, for example cardiac remodeling after myocardial infarction. These novel thermosensitive, biodegradable and flexible hydrogels have properties attractive for future application in soft tissue engineering.

Example 1

A Thermally Responsive Injectable Hydrogel Incorporating Hydroxyethyl Methacrylate-polylactide for Hydrolytic Lability Novel thermally responsive injectable and bioabsorbable hydrogel by copolymerization of N-isopropylacrylamide (NIPAAm), acrylic acid (AAc), and biodegradable monomer hydroxyethyl methacrylate-poly(trimethylene carbonate) (HEMAPTMC) is synthesized and evaluated. We sought to investigate and tune the molecular design by altering the relative amount of AAc so that a thermoresponsive hydrogel would be achieved with an LCST below body temperature prior to hydrolysis of the poly(trimethylene carbonate) (PTMC) branches, but with an LCST that rose above body temperature with PTMC cleavage. The HEMAPTMC component was selected and synthesized for use since the carbonate bond in PTMC should have a hydrolysis rate that would allow retention of the gel over the several week period that we hypothesize would be necessary for the cardiac application in vivo. After characterizing and optimizing the copolymer structure, the optimized hydrogel was evaluated by injection into chronic rat myocardial infarctions two weeks following coronary ligation, and the resulting cardiac performance and ventricular remodeling were assessed over an 8 week period. Our hypothesis was that injection of the designed thermoreponsive hydrogel would alter the progression of ventricular remodeling, preserving ventricular wall thickness and maintaining contractile function.

Chemicals were purchased from Sigma-Aldrich unless otherwise stated. NIPAAm was purified by recrystallization from hexane and vacuum dried. NIPPAm (50 g) was dissolved into 150 mL hexane at 80° C. and then recrystallized at room temperature. AAc and 2-hydroxyethyl methacrylate (HEMA) were purified by vacuum distillation at 70° C. and 100° C., respectively. Benzoyl peroxide (BPO), stannous 2-ethylhexanoate [$Sn(OCt)_2$], trimethylene carbonate (TMC, Boehringer Ingelheim Chemicals Inc.) were used as received.

Synthesis of HEMA-polyTMC (HEMAPTMC)

HEMAPTMC was synthesized by ring-opening polymerization of TMC initiated by HEMA with $Sn(OCt)_2$ as a catalyst (FIG. 1). Stoichiometric amounts of HEMA and TMC (molar ratio 1:2) were mixed in a flask to which was added anhydrous toluene of equal mass to the TMC/HEMA mixture. $Sn(OCt)_2$ (1 mol % with respect to HEMA) in 1 mL toluene was subsequently added. The reaction was conducted at 120° C. for 1.5 h. The mixture was then dissolved in THF and precipitated in water. This precipitation process was repeated twice and the liquid precipitate was then isolated by centrifugation, dissolved in THF, and dried over anhydrous $MgSO_4$. THF was removed by rotary evaporation.

Synthesis of poly(NIPAAm-co-AAc-co-HEMAPTMC)

Poly(NIPAAm-co-AAc-co-HEMAPTMC) copolymers were synthesized by free radical polymerization (FIG. 1). Monomers (NIPAAm, AAc, HEMAPTMC) were dissolved in 1,4-dioxane to form a 5 wt % solution containing BPO ($7.2 \times 10^{-3}$ mol/mol monomer). The polymerization was carried out at 70° C. for 24 h under argon atmosphere. The copolymer was precipitated in hexane and further purified by precipitation from THF into diethyl ether. The purified copolymer was vacuum dried.

Material Characterization $^1$H-NMR and $^{13}$C-NMR spectra of HEMAPTMC and the poly(NIPAAm-co-AAc-co-HEMAPTMC) copolymers were recorded with a 300 MHz BRUKER spectrometer using $CD_3Cl$ or DMSO-$d_6$ as a solvent. AAc content in the copolymers was determined by titration, in which copolymers were dissolved into deionized water with a concentration of 16.7 wt % at 4° C. and titrated with NaOH (0.1M) with phenolphthalein as a pH indicator. Molecular weight of the various polymers was determined by gel permeation chromatography (GPC, Waters Breeze System, Waters 1515 HPLC Pump, Waters 2414 differential refractometer). The copolymers were dissolved in THF with a concentration of 1 mg/mL and the GPC tests were made at 35° C. with THF as a solvent. A poly(methyl methacrylate) standard kit (Fluka, ReadyCal Set Mp 500-2,700,000) was used for molecular weight-elution volume calibration. LCSTs of the copolymer solutions in PBS (16.7 wt %, pH 7) were studied by measuring UV-optical absorption at 500 nm over a temperature range of 0 to 45° C. The LCST of each copolymer was determined (n=4) by determining the temperature at which the absorbance of the copolymer solution reached half of its maximal value, during the phase transition.

Gelation properties of the copolymer solutions (PBS, 16.7 wt %) were studied by incubating glass vials (3 mL) containing 1 mL solution in a 37° C. water bath. The water content of the hydrogel at body temperature and mechanical properties were measured after 24 h incubation. Water content was defined as $(w_2-w_1)/w_2 \times 100\%$, where $w_2$ and $w_1$ are wet mass and dry mass of the hydrogel, respectively. To measure hydrogel mechanical (tensile) properties, the hydrogel was cut into rectangular strips 1 mm thick, 4 mm wide and 25 mm long. Samples (n=4) were loaded in a water bath test cell equilibrated to 37±2° C. and attaching preheated grips to each end. An ATS 1101 Universal Testing Machine equipped with a 101b load cell was utilized with a cross-head speed of 6 cm/min.

Hydrogel degradation rate was quantified by mass loss measurement. Hydrogels with known initial dry masses (~60 mg) were immersed into 7 mL PBS (pH 7, replaced weekly) at 37° C. At pre-defined time points over a 20 week period the hydrogels (n=4) were lyophilized and the relative mass loss recorded.

Cytotoxicity Assay

The cytotoxicity of the polymer degradation products was assessed by measuring the metabolic viability of cells cultured with medium supplemented with degradation products (Guan J, et al. Biomacromolecules 2008; 9: 1283-92). To verify this result cells were also observed under fluorescence microscopy after live/dead staining with a Promokine® Live/Dead Cell Staining Kit. Live/dead cells were observed with green/red fluorescence respectively using excitation at 480 nm or 540 nm.

The polymer degradation solution was prepared by hydrolysis of the copolymer in a 1.0 M NaOH solution at 4° C. for 5 d to cleave the PTMC side chains, followed by removal of NaOH from the solution using an Amberlite® IR-120H ion-exchange resin (Aldrich). The solution was then mixed with 10×EMEM culture medium (BioWhittaker®, Lonza) at a volume ratio of 9:1.

Rat vascular smooth muscle cells (RSMCs) were isolated according to the method of Ray et al. from recently deceased animals that had been utilized in other protocols (Ray J L, et al. Methods Cell Sci 2001; 23: 185-8). Cells were cultured in Dulbecco's modified Eagle medium (DMEM) supplemented with 10% fetal bovine serum (FBS) to the fifth passage and seeded into a 24-well tissue culture plate at a seeding density of 15,000/well. The copolymer degradation solution with EMEM was added into each well to obtain a final concentration of 5 mg/mL. For control purposes, culture medium without added degradation solution was used. Cell metabolic viability was measured (n=4) using an MTS assay kit (Promega CellTiter 96® Cell Proliferation Assay) to quantify mitochondrial activity.

Experimental Animals

Adult female Lewis rats (Harlan Sprague Dawley, Indianapolis, Ind.) weighing 200-250 g were used. The protocol followed National Institutes of Health (NIH) guidelines for animal care and was approved by the University of Pittsburgh's Institutional Animal Care and Use Committee and Children's Hospital of Pittsburgh Animal Research Care Committee.

Chronic Left Ventricular Infarction Model

Anesthesia was induced with 3.0% isoflurane inhalation followed by intubation and respiratory support with a rodent volume-controlled mechanical ventilator. While monitoring with an electrocardiogram and tail cuff blood pressure measurement, a left thoracotomy was performed to expose the heart and the proximal left anterior descending coronary artery was ligated with 7-0 polypropylene. The creation of myocardial ischemia was verified by regional cyanosis and ST segment elevation and the incision was closed in layers with 4-0 continuous silk sutures.

Poly(NIPAAm-co-AAc-co-HEMAPTMC) (86/4/10) Hydrogel Injection

Two weeks after induction of myocardial infarction, the rats were anesthetized and evaluated with echocardiography to measure infarct size in terms of the percentage of scar area (akinetic or dyskinetic regions) to LV free wall area (Matsubayashi K, Fedak P W, Mickle D A, Weisel R D, Ozawa T, Li R K. Improved left ventricular aneurysm repair with bioengineered vascular smooth muscle grafts. Circulation 2003; 108: 219-25). A total of 17 rats with infarcts greater than 25% of the LV free wall were randomly divided into two groups: those that would receive hydrogel injections (hydrogel group n=9), and those that would receive the control PBS injections (PBS group; n=8). The infarcted anterior surface of the rat heart was exposed through a left thoracotomy. For a rat in the hydrogel group a total of 500 μL of poly(NIPAAm-co-AAc-co-HEMAPTMC) (86/4/10) solution in PBS (16.7 wt %) was injected into the apical, proximal, lateral, and septal wall regions bordering the infarct as well as into the center of the infarct (5 injections, 100 μL per region). For a rat in the PBS group, 500 μL PBS was injected into the same locations with the same volumes. The incision was closed in layers with 4-0 silk continuous sutures for both groups.

Histology

Eight weeks after injection (10 weeks after myocardial infarction), rats in both surgical groups were anesthetized, and the heart was exposed and arrested by apical injection of 2 mL of a hypothermic arresting solution (68 mM NaCl, 60 mM KCl, 36 mM NaHCO$_3$, 2.0 mM MgCl$_2$, 1.4 mM Na$_2$SO$_4$, 11 mM dextrose, 30 mM butanedione monoxime, and 10,000 U/L of heparin). The heart was explanted and fixed in 2% paraformaldehyde for 2 h and then embedded with optimal cutting temperature compound (Tissue-Tek, Torrance, Calif.) followed by freezing at −80° C. Embedded, frozen LV tissues were serially sectioned at 8 μm in the LV transverse direction. Hematoxylin and eosin (H&E) staining and immunohistochemical staining were performed as previously described (Fujimoto K L, et al. Ann Thorac Surg 2007; 83: 648-54) with antibodies against alpha-smooth muscle actin (α-SMA, Sigma, St Louis, Mo.), CD 31 (Serotec, Raleigh, N.C.), caldesmon (Abcam, Cambridge, Mass.), calponin (Abcam), smooth muscle myosin heavy chain 2 (SMMHC-2, Abeam), SM-22α (Abeam). Nuclei were stained with 4',6-diamidino-2-phenylIndole (DAPI, Sigma).

LV Wall Thickness and Capillary Density.

For each LV sample 5 different microscopic fields at 100× magnification for the wall thickness measurement and 10 different fields at 200× magnification for the capillary density measurement were photographed for 5 rats in each group 8 weeks after the injection procedure. The wall thickness of the infarcted anterior wall where the injections were performed was analyzed using NIH Image software. Capillaries were recognized as tubular structures positively stained for CD31 as previously described (Oshima H, et al. Mol Ther 2005; 12: 1130-41).

Echocardiography

Echocardiography was performed immediately prior to injection (pre-injection time point, which was 2 weeks post-infarction), as well as 4 and 8 weeks after hydrogel or PBS injection. Rats were anesthetized with isoflurane inhalation. Standard transthoracic echocardiography was performed using the Acuson *Sequoia* C256 system with 13-MHz linear ultrasonic transducer (15L8; Acuson Corporation, Mountain View, Calif.) in a phased array format. B-mode measurements on the LV short axis view (papillary muscle level) were performed. The end-diastolic (EDA) and end-systolic (ESA) LV internal cavity areas were measured by tracing the endocardial border. The LV fractional area change (% FAC) was estimated as, % FAC=[(LVEDA-LVESA)/LVEDA]×100%. All measurements were performed using Scion Image software (Scion Image, Frederick, Md.).

Statistics

All data are expressed as means with the standard deviation. Analyses utilized SPSS software (SPSS Inc, Chicago Ill.). Statistical analyses were performed by ANOVA or 2-way repeated measures ANOVA with Tukey's test applied to investigate specific differences. Statistical significance was defined at p<0.05. The wall thickness and capillary density in each group was compared by Student's t-test.

Results

Synthesis of HEMAPTMC and Copolymer

Figure 2A:
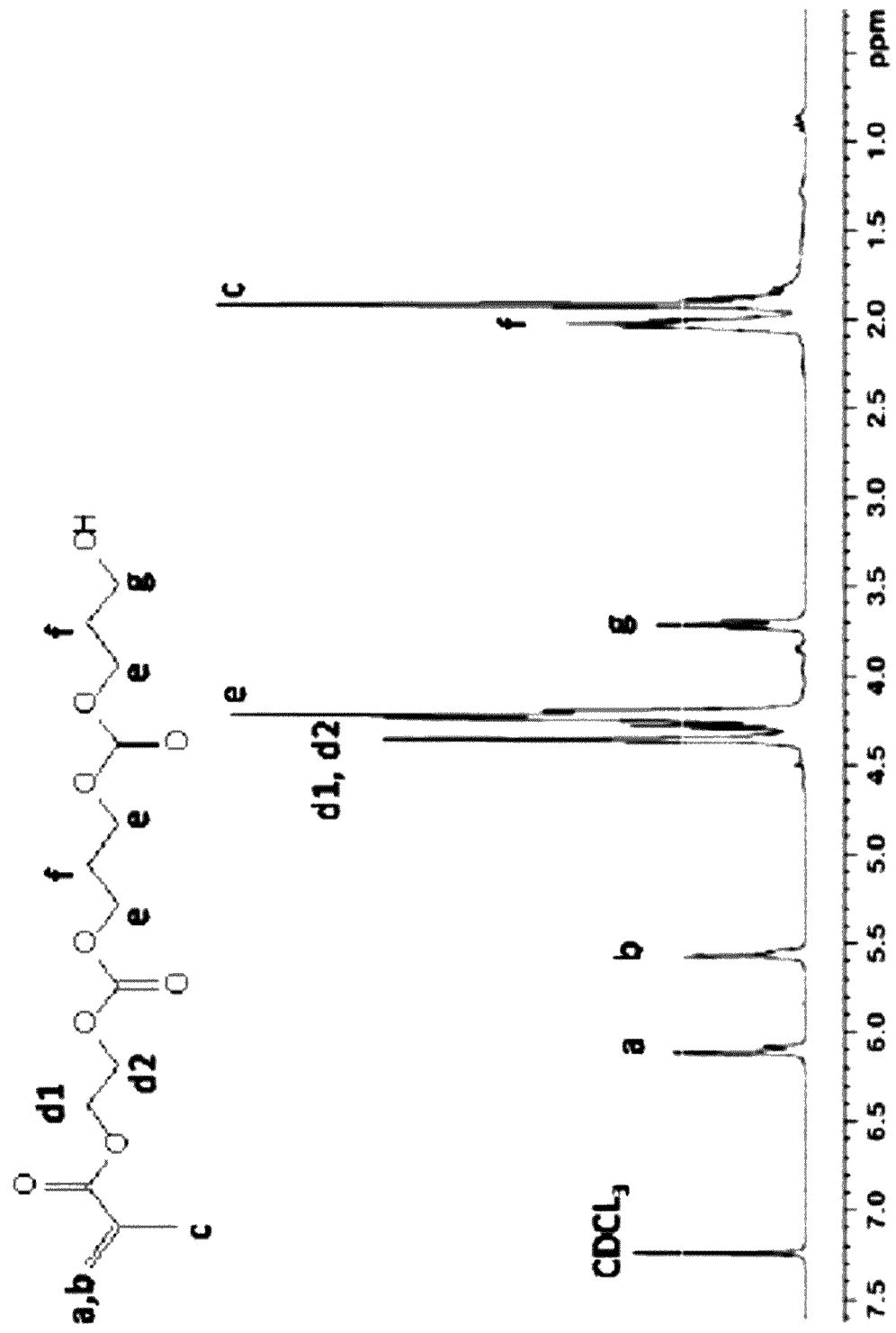
(FIG. 2A) $^1$H-NMR and (FIG. 2B) $^{13}$C-NMR spectra for HEMAPTMC.
Figure 2B:
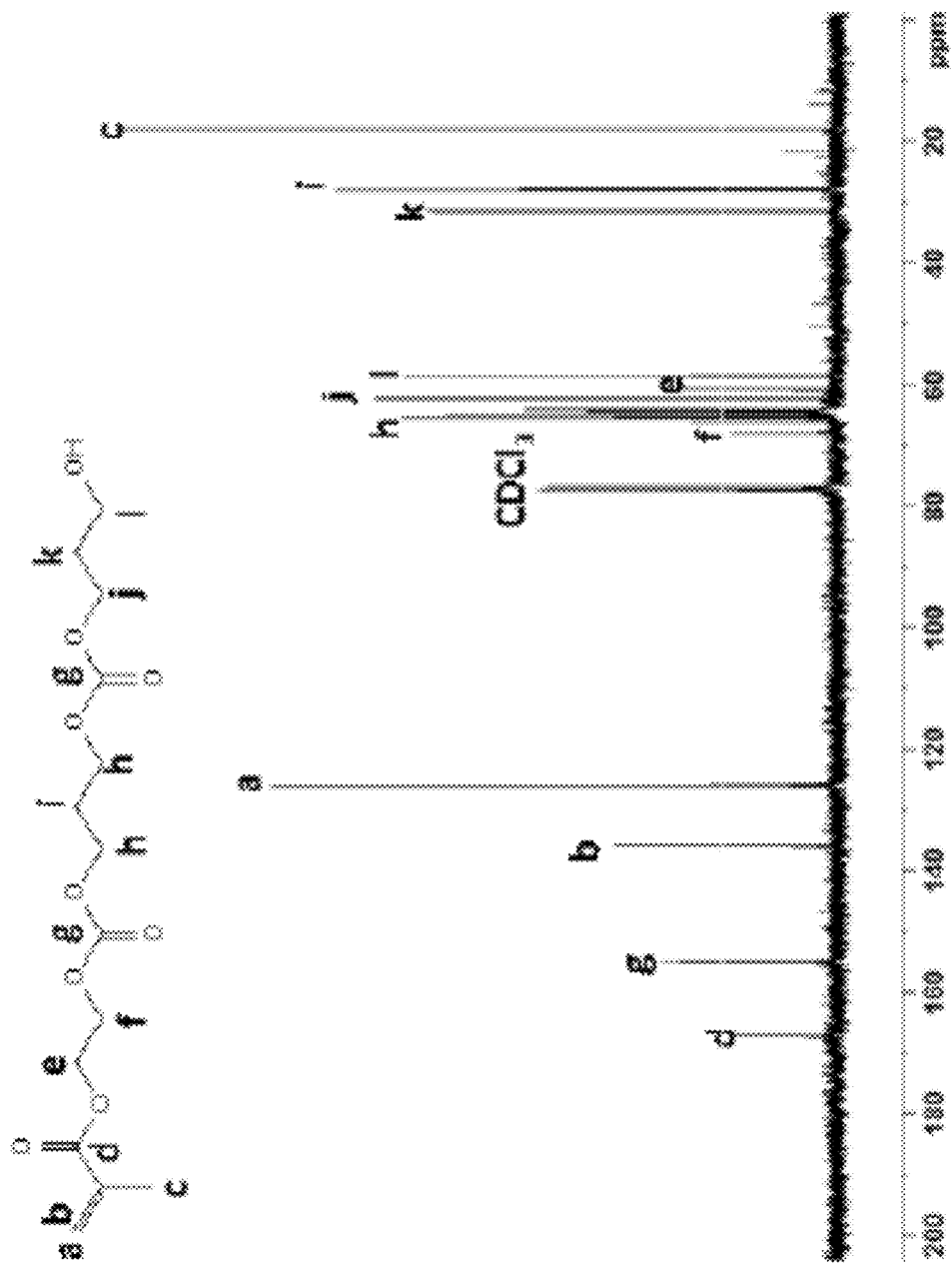
FIG. 2.

The synthesis of HEMAPTMC was confirmed by the 1H-NMR spectrum of the product (FIG. 2a) and the $^{13}$C-NMR spectrum (FIG. 2b) containing proton peaks and carbon peaks in agreement with the molecular structure of HEMAPTMC. In the $^1$H-NMR spectrum, HEMA alone would be expected to have two characteristic triple peaks centered at 4.4 ppm and 3.9 ppm for d protons, while for HEMAPTMC the combination of the two d peaks into a single peak at 4.4 ppm provides confirmation of the formation of HEMAPTMC. The chemical structure of HEMAPTMC was further confirmed by the mass spectrum (API-ES positive). Peaks at 254.8 (HEMAPTMC1+Na$^+$), 357.0 (HEMAPTMC2+Na$^+$), 459.0 (HEMAPTMC3+Na$^+$), 561.0 (HEMAPTMC4+Na$^+$) and 663.0 (HEMAPTMC5+Na$^+$) were observed, indicating that the product was a mixture of molecules containing different PTMC lengths. The number average length of PTMC units per monomer was determined from $^1$H-NMR spectrum (FIG. 2a) as 2 by calculation from the ratio of the integrals of hydrogen peaks from PTMC (peak e, f and g) and the double bond hydrogen (CH2=) peak (peak a and b at 5.6 and 6.1 ppm). This PTMC unit number for HEMAPTMC was in agreement with the molar feed ratio of HEMA to TMC (1:2) in the synthesis of HEMAPTMC.

Figure 3A:
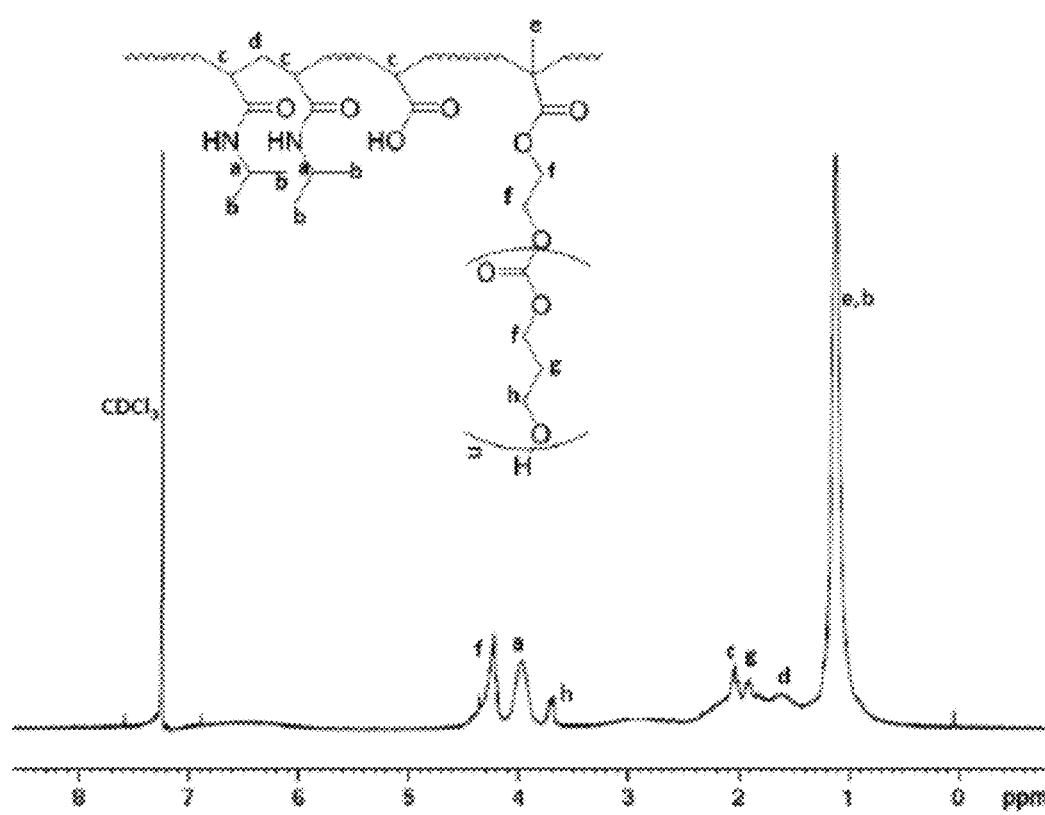
(FIG. 3A) $^1$H-NMR and (FIG. 3B) $^{13}$C-NMR spectra for poly(NIPAAm-co-AAc-co-HEMAPTMC) (86/4/10).
Figure 3B:
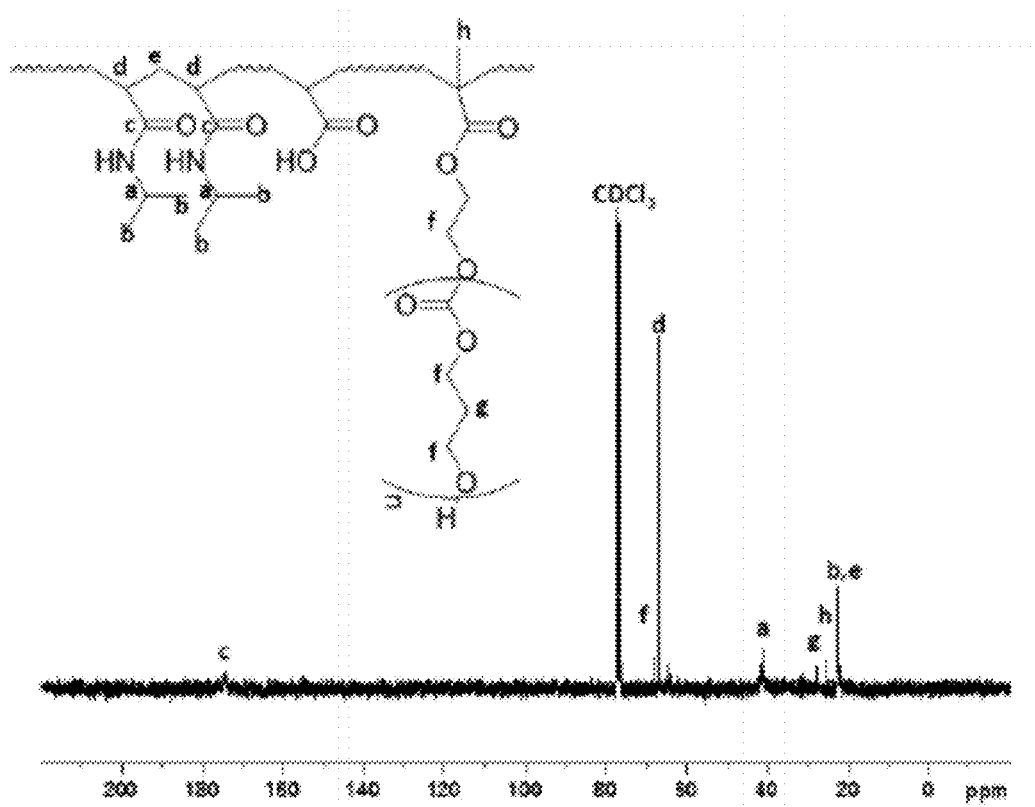
FIG. 3.

Copolymers with different monomer ratios were prepared by free radical polymerization (FIG. 1). Table 1 summarizes poly(NIPAAm-co-AAc-co-HEMAPTMC) copolymers synthesized with different AAc feed ratios. All of the copolymers have molecular weights between 20 k and 30 k, and a polydispersity index of 1.5~2.0. FIG. 3 shows typical $^1$H-NMR and $^{13}$C-NMR spectra for a synthesized copolymer. Proton and carbon peaks characteristic of NIPAAm and HEMAPTMC are seen in the spectra. The existence of AAc (—COOH) units in the copolymer was verified and quantified by titration of the polymer solution with NaOH solution (0.1 M). The AAc content obtained by the titration method and the integration ratios of characteristic proton peaks in the $^1$H-NMR spectra were used to determine copolymer compositions (Table 1). The monomer compositions in the copolymers were found to be close to the feed ratios, with a consistent slight reduction in the measured AAc content from that expected based on the feed ratio.

temperature at which optical absorption rapidly transitions (the LCST) is seen to increase as the AAc feed ratio of the copolymer is increased. While copolymers with AAc feed ratios of 3, 4 and 5% had LCSTs below 37° C., the copolymer with an AAc feed ratio of 6% had an LCST of 45° C.

Figure 4A:
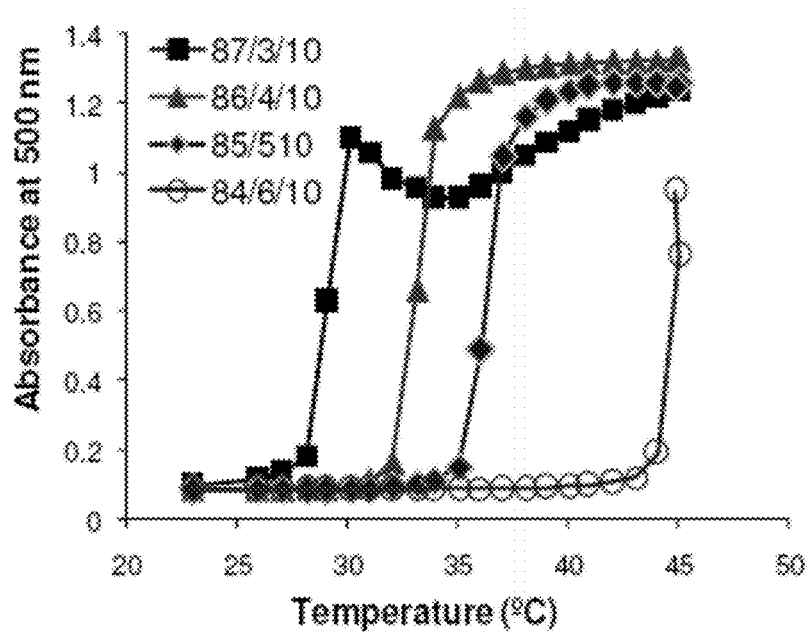
FIG. 4. LCST determination by measurement of copolymer solution optical absorption as a function of temperature. For each copolymer a representative curve is shown. (a) Copolymers poly(NIPAAm-co-AAc-co-HEMAPTMC) with varying AAc feed ratio; (b) copolymers poly(NIPAAm-co-AAc-co-HEMA) with varying AAc feed ratio.
Figure 4B:
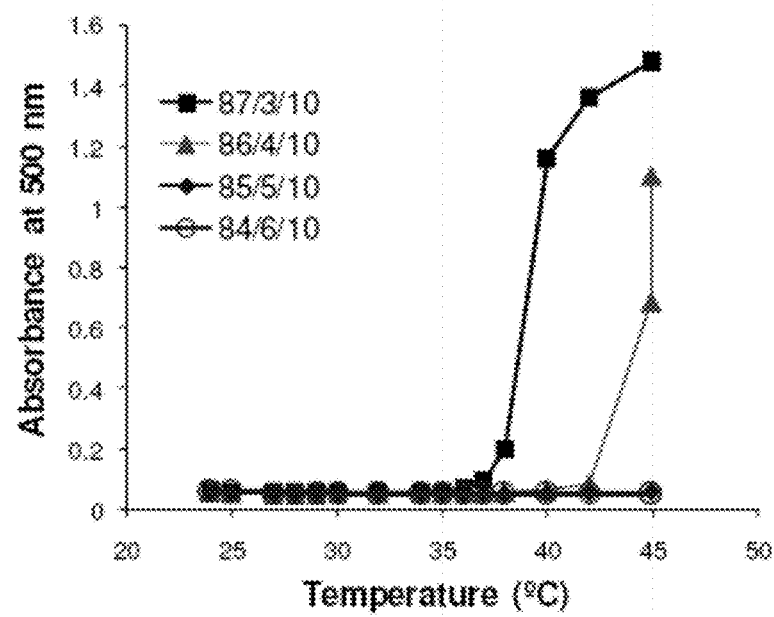

In addition to evaluating copolymers of poly(NIPAAm-co-AAc-co-HEMAPTMC), copolymers of poly(NIPAAm-co-AAc-co-HEMA) were also synthesized with fixed HEMA molar feed ratios of 10% and with different AAc molar feed ratios (3, 4, 5, and 6%). These HEMA containing copolymers were evaluated since cleavage of the PTMC in the poly (NIPAAm-co-AAc-co-HEMAPTMC) would be expected to result in poly(NIPAAm-co-AAc-co-HEMA). The results in Table 2 present the physical state of various poly(NIPAAm-co-AAc-co-HEMA) solutions at 37° C. as well as LCSTs determined from optical absorption measurements (FIG. 4b). These data provide guidance as to whether one would expect the corresponding poly(NIPAAm-co-AAc-co-HEMAPTMC) to be soluble after complete removal of its PTMC residues. For these HEMA containing copolymers, when the AAc feed ratio was 3%, the copolymer solution was a cloudy

TABLE 1

Properties of poly (NIPAAm-co-AAc-co-HEMAPTMC) copolymers with different feed ratios of AAc.

| Feed ratio NIPAAm/AAc/HEMA PTMC | Yield | Mn g/mol | Mw/Mn | -COOH content, $10^{-4}$ mol/g | Polymer composition, NIPAAm/AAc/HEMAPTMC | 37° C., 16.7 wt % in PBS, pH 7 | LCST 16.7 wt % in PBS, pH 7, ° C. |
|---|---|---|---|---|---|---|---|
| 87/3/10 | 86% | 27,000 | 1.8 | 1.6 | 88.5/2.1/9.4 | solid gel | 29.1 ± 0.37* |
| 86/4/10 | 87% | 23,000 | 1.9 | 2.6 | 88.3/3.3/8.4 | solid gel | 33.1 ± 0.43* |
| 85/5/10 | 84% | 34,000 | 1.5 | 2.8 | 87.0/3.6/9.4 | cloudy, weak gel | 36.2 ± 0.38* |
| 84/6/10 | 93% | 21,000 | 2.0 | 3.8 | 86.2/4.8/8.9 | clear solution | 44.5 ± 0.10* | p < 0.001 versus each of other copolymers

Gelation Properties, the LCST and Optimization of Monomer Feed Ratio

The qualitative gelation properties of the poly(NIPAAm-co-AAc-co-HEMAPTMC) copolymers are summarized in Table 1. When the AAc feed ratio was 3% and 4%, a solid gel could be formed at 37° C. When the AAc feed ratio was increased to 5%, a fluid-like hydrogel with negligible strength was formed. When the AAc feed ratio was as high as 6%, the copolymer solution remained a clear solution at 37° C., indicating an LCST above 37° C. The calculated LCSTs were determined from the optical data represented in FIG. 4a. The liquid gel at 37° C., while AAc feed ratios of 4, 5 and 6% resulted in solutions that remained clear. This was further confirmed by LCST values, which showed that the copolymer with an AAc feed ratio of 3% had an LCST close to body temperature, while all other copolymers with higher AAc feed ratios had LCSTs well above 37° C. These results demonstrated that in synthesizing the poly(NIPAAm-co-AAc-co-HEMAPTMC), the AAc feed ratio should be higher than 3% to ensure that the polymer will become completely soluble upon cleavage of the PTMC residues.

TABLE 2

Properties of poly(NIPAAm-co-AAc-co-HEMA) copolymers with different feed ratios of AAc.

| Feed ratio NIPPAm/AAC/HEMA | Yield | Mn | Mw/Mn | -COOH content, $10^{-4}$ mol/g | Polymer composition NIPAAm/AAc/HEMA | 37° C., 16.7 wt % in PBS, pH 7 | LCST 16.7 wt % in PBS, pH 7, ° C. |
|---|---|---|---|---|---|---|---|
| 87/3/10 | 96% | 21,000 | 2.1 | 1.7 | 88.2/1.9/9.9 | cloudy, weak gel | 39.3 ± 0.42* |
| 86/4/10 | 89% | 29,000 | 1.7 | 2.3 | 86.9/2.5/10.6 | clear solution | 43.5 ± 0.84* |
| 85/5/10 | 92% | 21,000 | 1.9 | 2.9 | 87.0/3.2/9.8 | clear solution | >45 |
| 84/6/10 | 96% | 22,000 | 1.9 | 3.6 | 85.6/4.0/10.4 | clear solution | >45 | p < 0.001 between 87/3/10 and 86/4/10

Based on these results, to move forward towards the application of a poly(NIPAAm-co-AAc-co-HEMAPTMC) hydrogel in the treatment of myocardial infarcts, the optimal monomer feed ratio for NIPAAm, AAc and HEMAPTMC was considered to be 86/4/10. The resulting copolymer should provide an initial LCST between room temperature and body temperature, and theoretically be degradable to a soluble polymer with an LCST above body temperature. Further characterization studies utilized this copolymer.

A gross observation of the gelation process for the poly (NIPAAm-co-AAc-co-HEMAPTMC) (86/4/10) hydrogel solution (16.7 wt % in PBS) is shown in FIG. 5a-b. The sol-gel transition occurred immediately when the solution was immersed into the water bath of 37° C. After incubation for 10 min, a highly flexible gum-like material was formed (FIG. 5c-d). Upon continued warming in the water bath, the hydrogel gradually shrank, excluding water from inside, and became completely stable after 24 h. The final equilibrated water content of the hydrogel was measured as 60±5% and the maximum tensile strength of the equilibrated hydrogel was found to be 6.1±2.0 kPa with plastic deformation occurring beyond the maximum tensile strength at approximately 25% strain.

In vitro Degradation

Figure 6A:
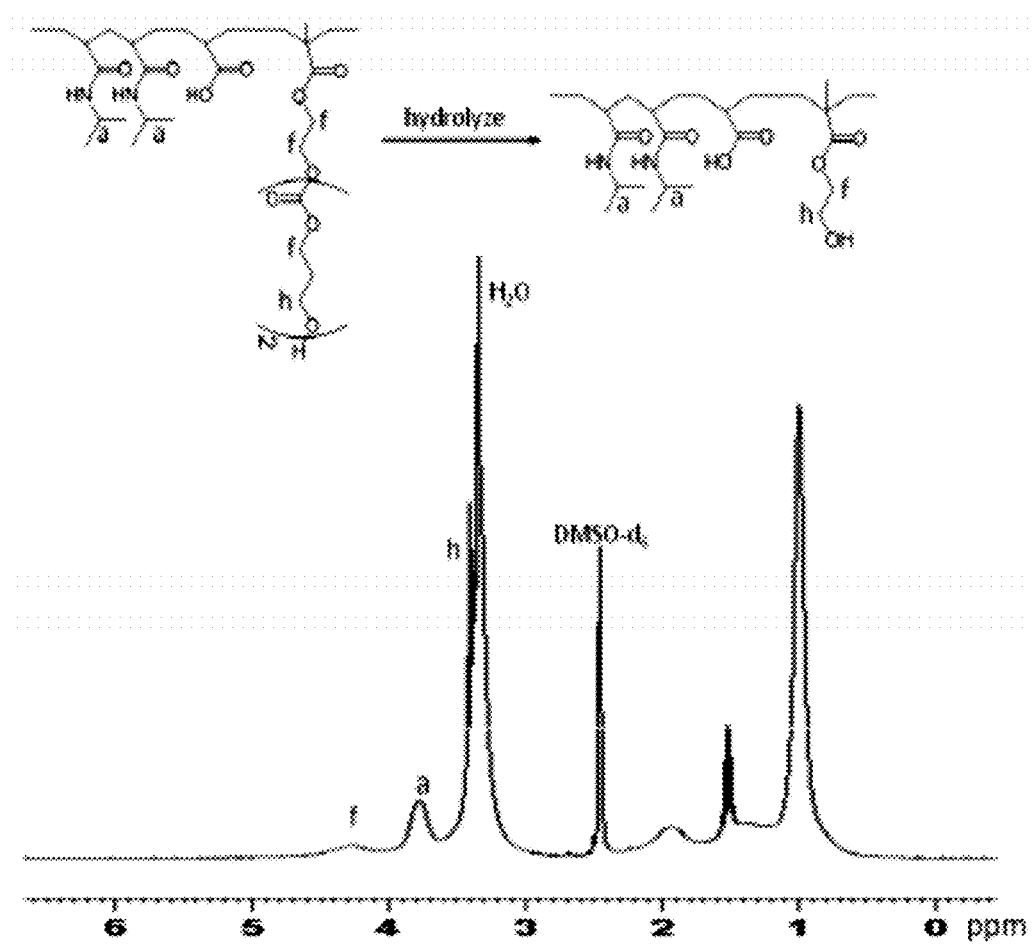
(FIG. 6A) $^1$H-NMR spectrum of degraded poly (NIPAAm-co-AAc-co-HEMAPTMC) (86/4/10)
Figure 6B:
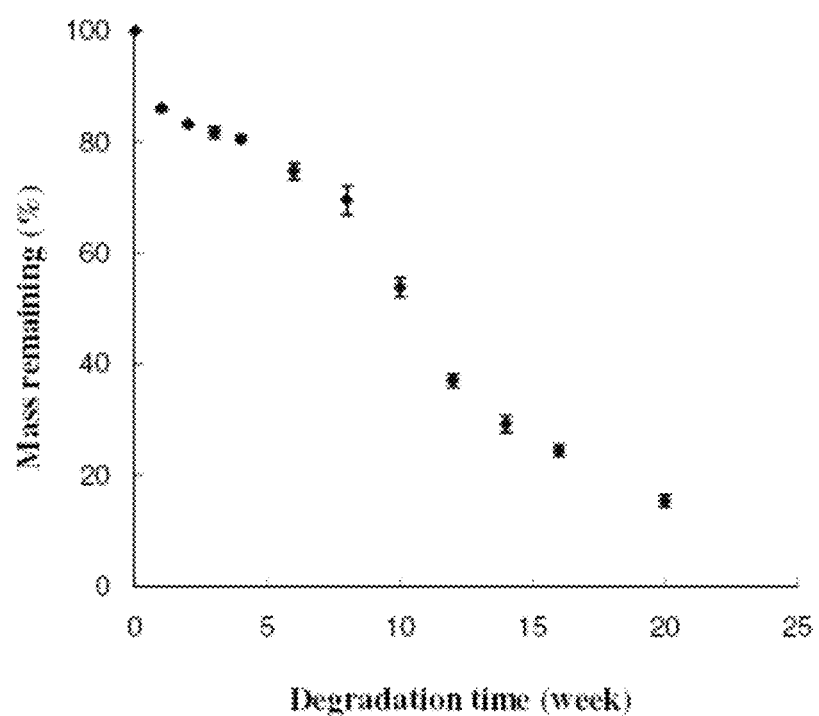
(FIG. 6B) mass loss of poly(NIPAAm-co-AAc-co-HEMAPTMC) (86/4/10) hydrogel in PBS at 37° C.

The in vitro degradation properties of the poly(NIPAAm-co-AAc-co-HEMAPTMC) (86/4/10) hydrogel was first evaluated by hydrolysis in NaOH (1M) at room temperature for 5 days to theoretically cleave the PTMC residues, representing extensive degradation of the copolymer. In FIG. 6a the $H^1$-NMR spectrum of this hydrolyzed copolymer is shown to exhibit a peak characteristic of PTMC at 4.3 ppm that was decreased compared with the NMR spectrum before degradation as shown in FIG. 3a. The hydrolyzed copolymer gave a clear solution at 37° C., demonstrating an LCST well above 37° C. A second evaluation of in vitro degradation of the hydrogel was performed in PBS at 37° C. with the resulting mass loss curve shown in FIG. 6b, the hydrogel was gradually solubilized at a much lower rate than in the NaOH solution, with mass loss of over 85% by 20 weeks.

Degradation Product Cytotoxicity

Figure 7:
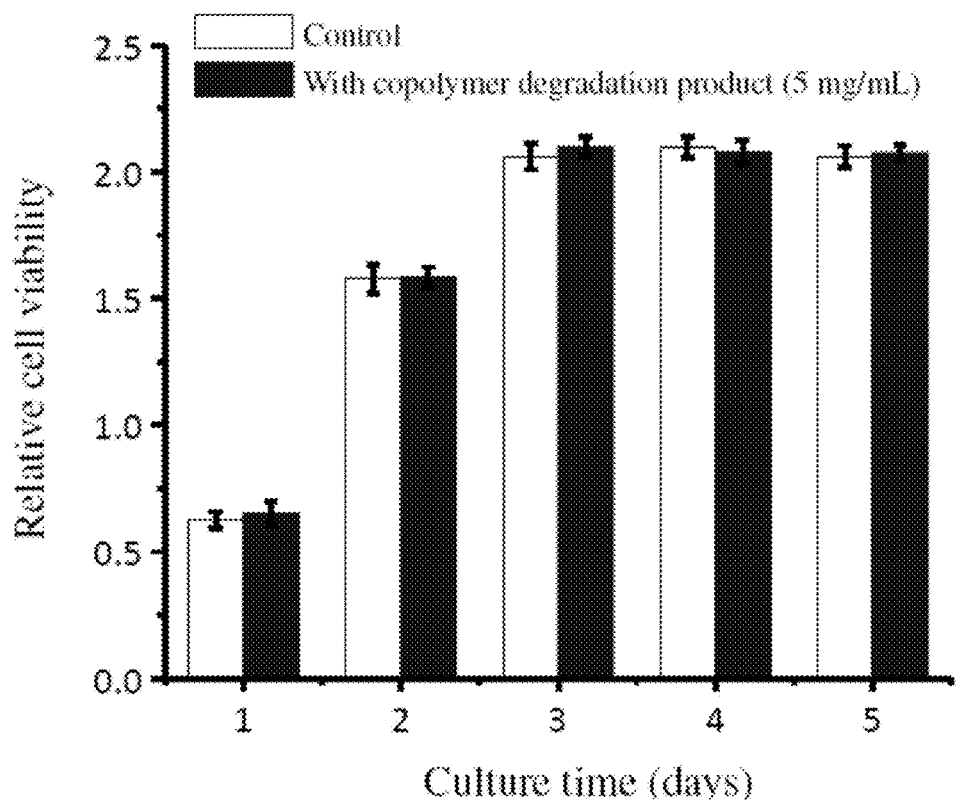
FIG. 7. Cytotoxity assay of poly(NIPAAm-co-AAc-co-HEMAPTMC) (86/4/10) hydrogel degradation products by cell metabolic activity assessment (MTS assay) for RSMCs cultured on TCPS. Hydrolyzed hydrogel solution was supplemented into cell culture medium at a final concentration of 5.0 mg/mL.
Figure 8A:
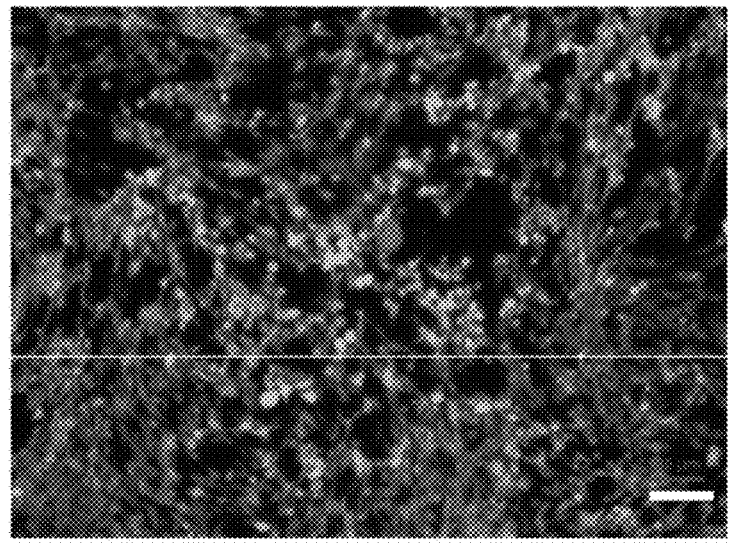
FIG. 8. Live/dead staining of RSMC cultured on TCPS using (FIG. 8A) untreated culture medium and (FIG. 8B) culture medium containing 5.0 mg/mL hydrolyzed poly (NIPAAm-co-AAc-co-HEMAPTMC) (86/4/10). Culture time of 3 days. Scale bar: 100 gam.
Figure 8B:
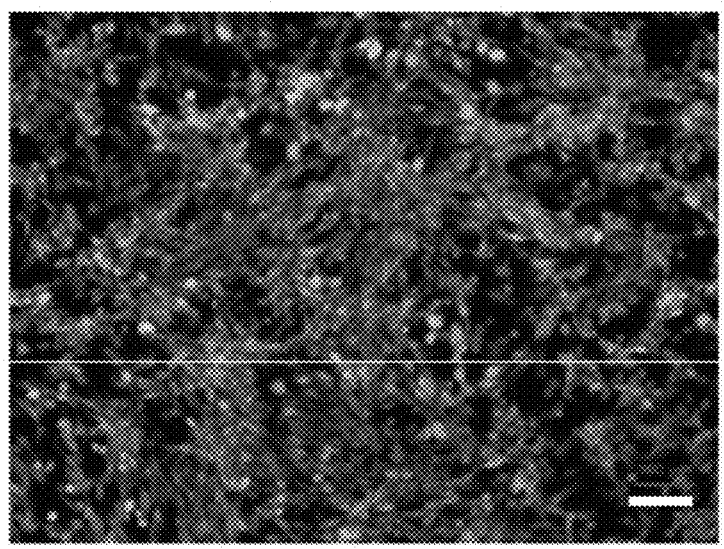

With RSMC mitochondrial activity serving as an index for cell viability, FIG. 7 demonstrates a lack of toxic effect of degradation product containing medium on RSMC culture. This result was further verified by fluorescent live/dead staining of RSMC cultures under control or degradation product containing culture medium (FIG. 8). For both culture media, dead cells marked by the red color were seen in low numbers and no difference was apparent in the relative number of dead cells viewed over several culture wells.

Injection in Chronic Infarction Model: External Morphology and Histology

There were no early or late postoperative deaths in either surgical group. After the 8 week evaluation period 3 of 8 animals in the PBS injection group had obvious ventricular aneurysm formation in the apex area (FIG. 9a). The other rats in this group did not have obvious aneurysms, but did have well defined scar areas. For the hydrogel injection group the treated infarcts were covered with fat connective tissue with no strong adhesions and no aneurysms (FIG. 9b).

In the PBS injected animals, examining H&E stained sections revealed extensive fibrous tissue and decreased tissue thickness in the anterior-lateral wall in all animals and aneurysm formation in the anterior wall in the same animals where this attribute was grossly apparent at the time of explant (FIG. 9c). On the other hand, in the hydrogel injected group, the thickness of the ventricular wall was relatively preserved (FIG. 9d). The remnant injected hydrogel material appeared to be distributed in the anterior wall and infiltrated with macrophages and fibroblasts. In addition, beneath the distributed hydrogel, a muscle-like layer was observed (FIG. 10a). Immunohistochemical staining showed that this muscle-like layer was positive for α-SMA (FIG. 10b). In higher magnification images, cellular ingrowth was found inside the hydrogel area, with some regions of this tissue structure staining positively for α-SMA (FIG. 11a-d). Further immunohistochemical staining demonstrated that caldesmon, calponin, SM 22α, and SMMHC type II (caldesmon images shown in FIG. 12a), all proteins that are associated with contractile function, co-localized with α-SMA positive cells in the hydrogel injected myocardial sections.

Figure 12:
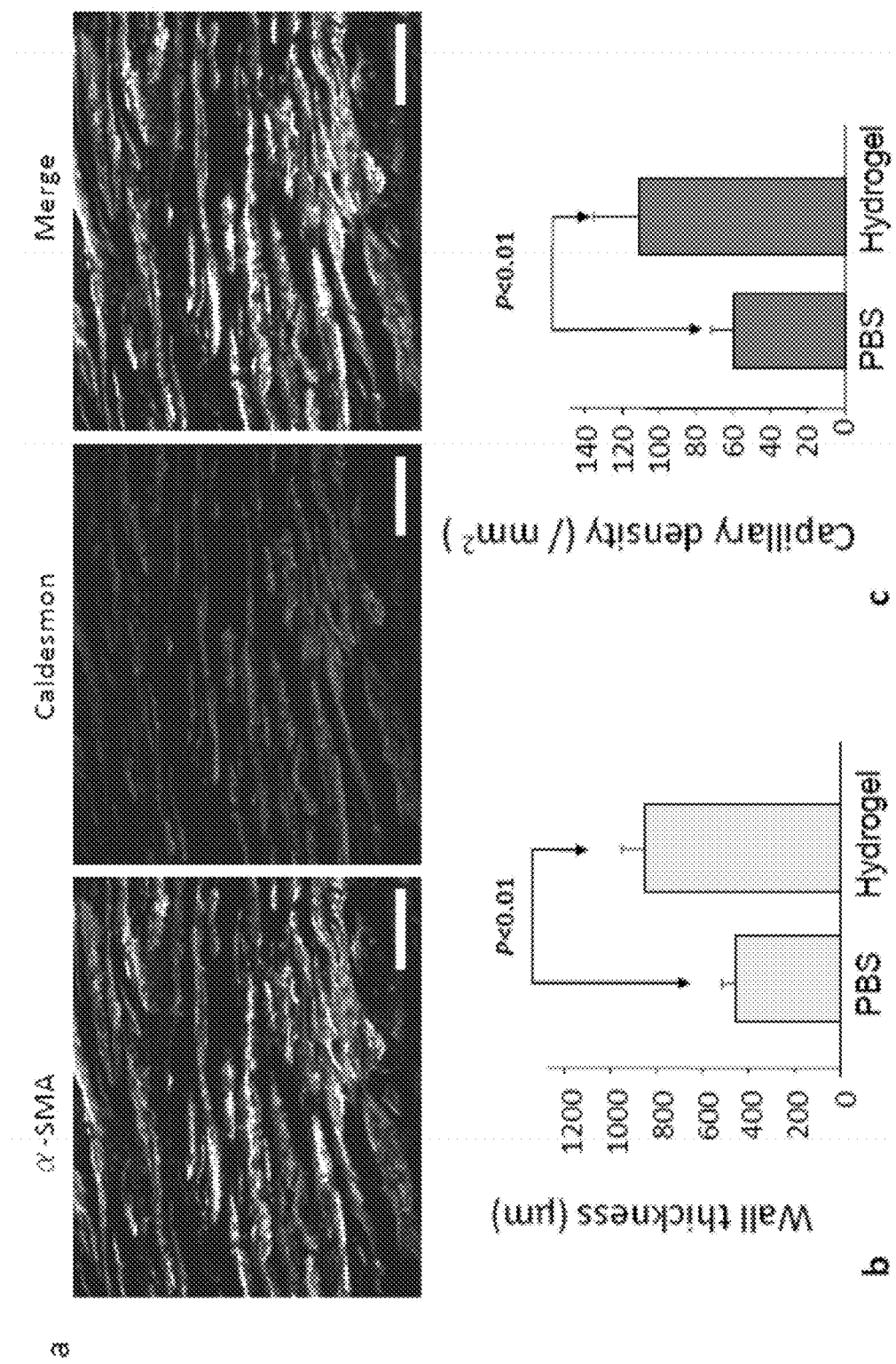
FIG. 12. (a) Co-localization of α-SMA and caldesmon with immunohistochemical staining. Scale bars: 50° μm. (b) The left ventricular myocardial wall thickness and (c) capillary density of comparing the hydrogel and PBS injection groups at 8 weeks following injection.

From histological section image analysis, the LV myocardial wall for the hydrogel injection group was found to be thicker than for the PBS injection control group (825±92 vs. 412±104 μm, p<0.01, FIG. 12b). The capillary density in the hydrogel group was also significantly higher in comparison to the PBS injection group (110±26 vs. 59±17/$mm^2$, p<0.01, FIG. 12c).

Injection in Chronic Infarction Model: Cardiac Function

Figure 13A:
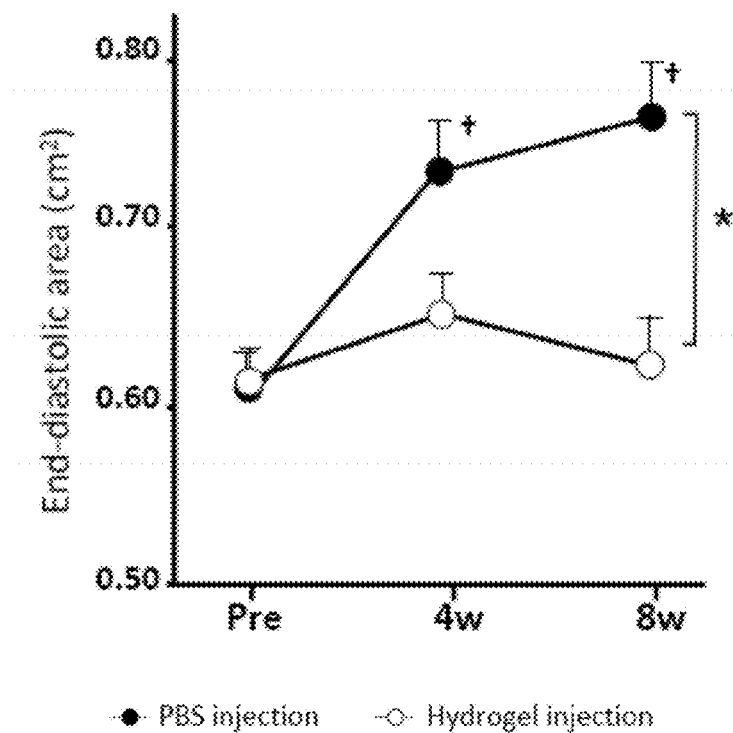
(FIG. 13A) EDA (end-diastolic area), and (FIG. 13B) % fractional area change (% FAC). *; p<0.05 between groups, †; p<0.05 vs. pre-injection time point within group.
Figure 13B:
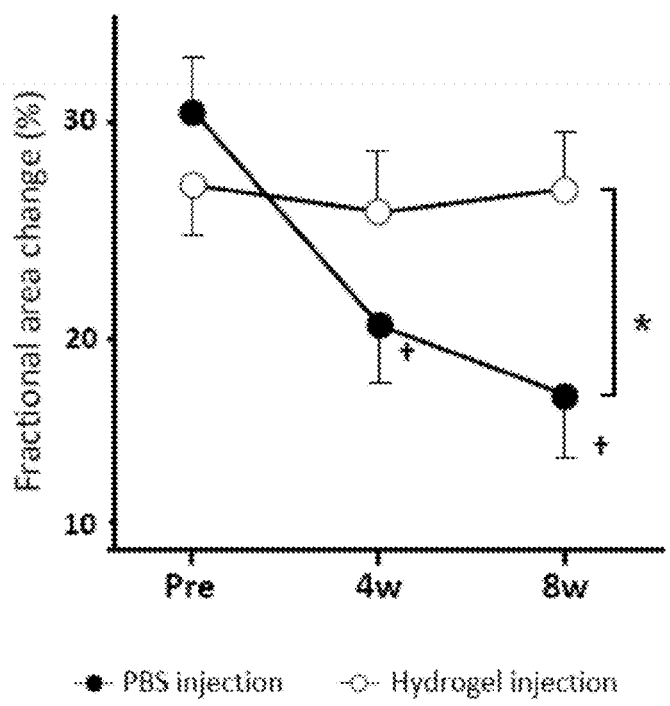
FIG. 13. Echocardiographic assessment of the hydrogel and PBS injection groups during the study period.

Longitudinal echocardiography showed that the LV EDA increased and the % FAC decreased in the period following the injection procedure (at 4 and 8 weeks, each versus the pre-injection period, p<0.05). The hydrogel group did not experience a change in EDA or % FAC following injection at either of the time points relative to the pre-injection time point. At 8 weeks, the EDA in the PBS group had become significantly larger than that of the hydrogel group, and also the % FAC of the PBS group was also significantly smaller than that of the hydrogel group (FIG. 13).

Discussion

We previously reported on the development of a thermoresponsive and biodegradable hydrogel by the copolymerization of NIPAAm, AAc, N-acryloxysuccinimide (NAS) and HEMAPLA (Guan J, et al. Biomacromolecules 2008; 9: 1283-92). However, application of this hydrogel in vivo for cardiac wall injection therapy was considered non-ideal since in pilot studies with subcutaneous tissue injection it was found to be rapidly resorbed within two days (data not shown). The postulated mechanical benefits of gel injection on the cardiac wall might thus be too transient (Wall S T, et al. Circulation 2006; 114: 2627-35). In this example, we considered an alternative molecular structure for a thermoresponsive hydrogel where instead of using HEMAPLA, another biodegradable monomer, HEMAPTMC, was synthesized on the theory that the carbonate bond in PTMC residues would experience hydrolysis at a slower rate than the ester bonds in the PLA residue. The synthesis of the HEMAPTMC and the copolymer poly(NIPAAm-co-AAc-co-HEMAPTMC) were confirmed with NMR spectra (FIGS. 2 and 3). Monomer ratios of copolymers were determined and were found to be similar to the feed ratios (Table 1), with a consistent slight reduction in the AAc content. Previous studies reported that AAc has slightly lower reactivity than NIPAAm in benzene, while HEMA and HEMAPLA, which have similar structures to HEMAPTMC, have close reactivity to NIPAAm (Rzaev Z M O, et al. Prog Polym Sci 2007; 32: 534-95).

One design objective for the HEMAPTMC-containing hydrogel was that it should be capable of gelation at 37° C., and be slowly solubilized at this temperature as the PTMC residues are hydrolytically cleaved. To achieve this, control of the AAc content in the copolymer poly(NIPAAm-co-AAc-co-HEMAPTMC) is of importance. AAc is a highly hydrophilic monomer since its —COOH residues will be deprotonized into highly hydrated —COO— groups at neutral pH. If the AAc content in the copolymer is too high, the copolymer will be too hydrophilic so that the copolymer solution will have an LCST above 37° C. and will not be able to form a hydrogel at 37° C. On the other hand, if the AAc content in the copolymer is too low, the copolymer will be too hydrophobic so that even after removal of the PTMC residues the LCST would remain below 37° C. and the copolymer would not become soluble. By performing a set of experiments to explore the gelation properties and LCSTs of various poly(NIPAAm-co-AAc-co-HEMAPTMC) and poly(NIPAAm-co-AAc-co-HEMA) copolymers with different AAc feed ratios (Tables 1 and 2, FIG. 4), we were able to determine that an appropriate monomer feed ratio for NIPAAm, AAc and HEMAPTMC was approximately 86/4/10, and the resulting copolymer was adopted for the cardiac application studies.

Figure 5:
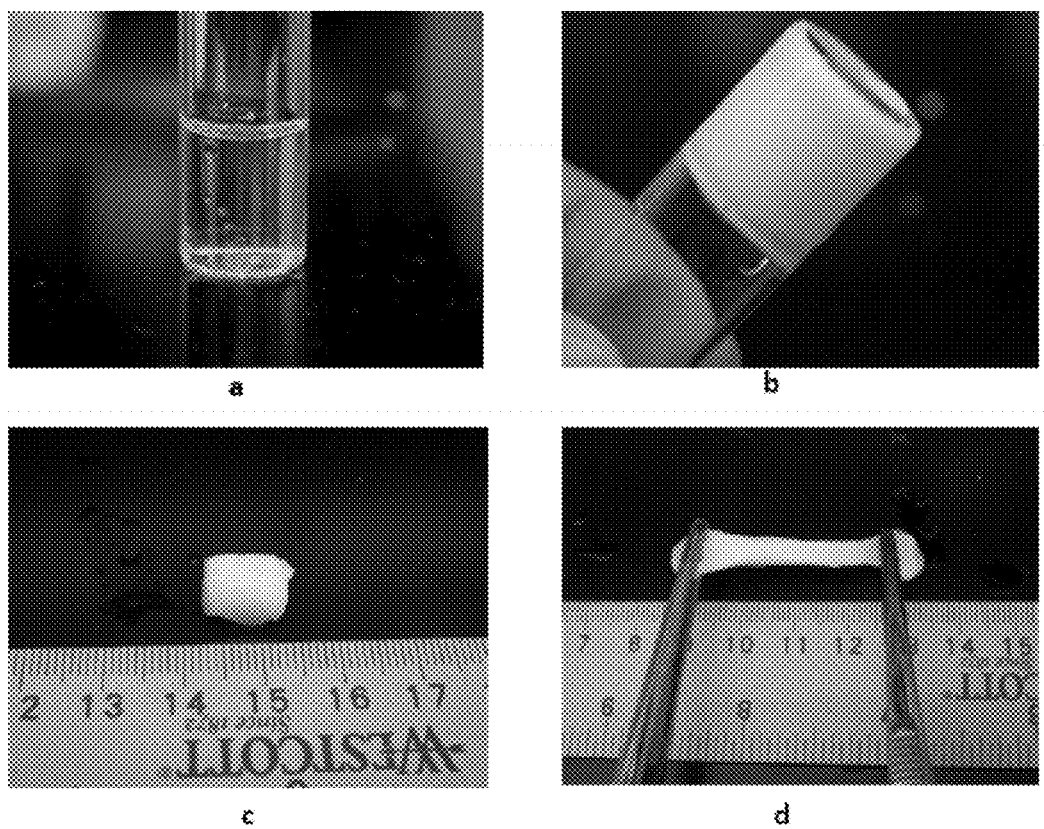
FIG. 5. Gelation properties of the (NIPAAm-co-AAc-co-HEMAPTMC) (86/4/10) hydrogel. (a) Cooled hydrogel solution; (b) after incubation in 37° C. water bath for 30 sec; (c) hydrogel formed after 10 min; (d) stretching of the hydrogel that was formed after 10 min.
Figure 9:
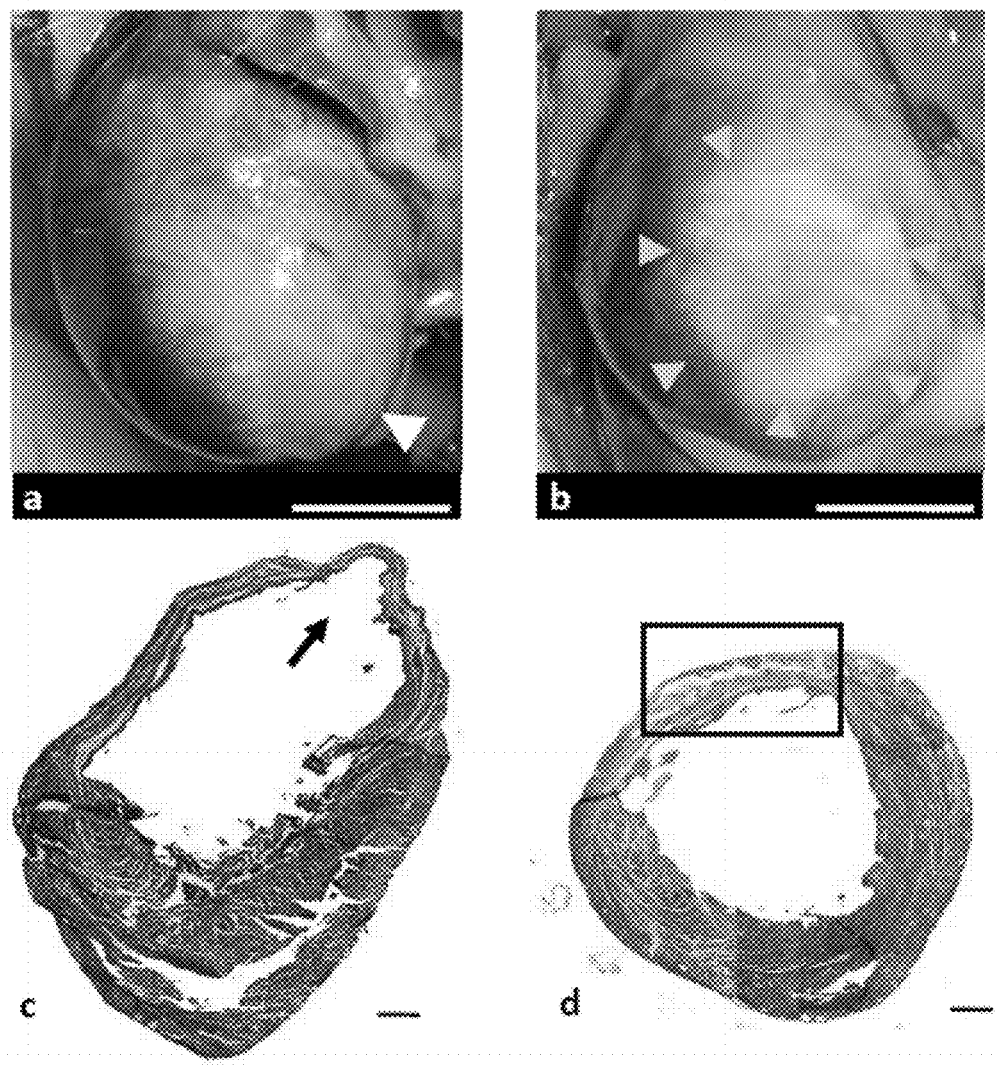
FIG. 9. Representative images at 8 weeks following the injection procedure of the anterior view of (a) PBS injected, and (b) poly(NIPAAm-co-AAc-co-HEMAPTMC) (86/4/10) injected hearts. White arrow shows an aneurysm formation in the apex area (a). Blue arrows indicate the injected hydrogel area (b). The composite histological sections of (c) PBS injected and (d) hydrogel injected myocardial walls 8 weeks after injection stained with H&E. Black arrow shows an aneurysm formation (c). Blue box indicates higher magnification area shown in FIG. 10 (d). Scale bar: 5 mm in (a, b), 500 μm in (c, d).
Figure 10:
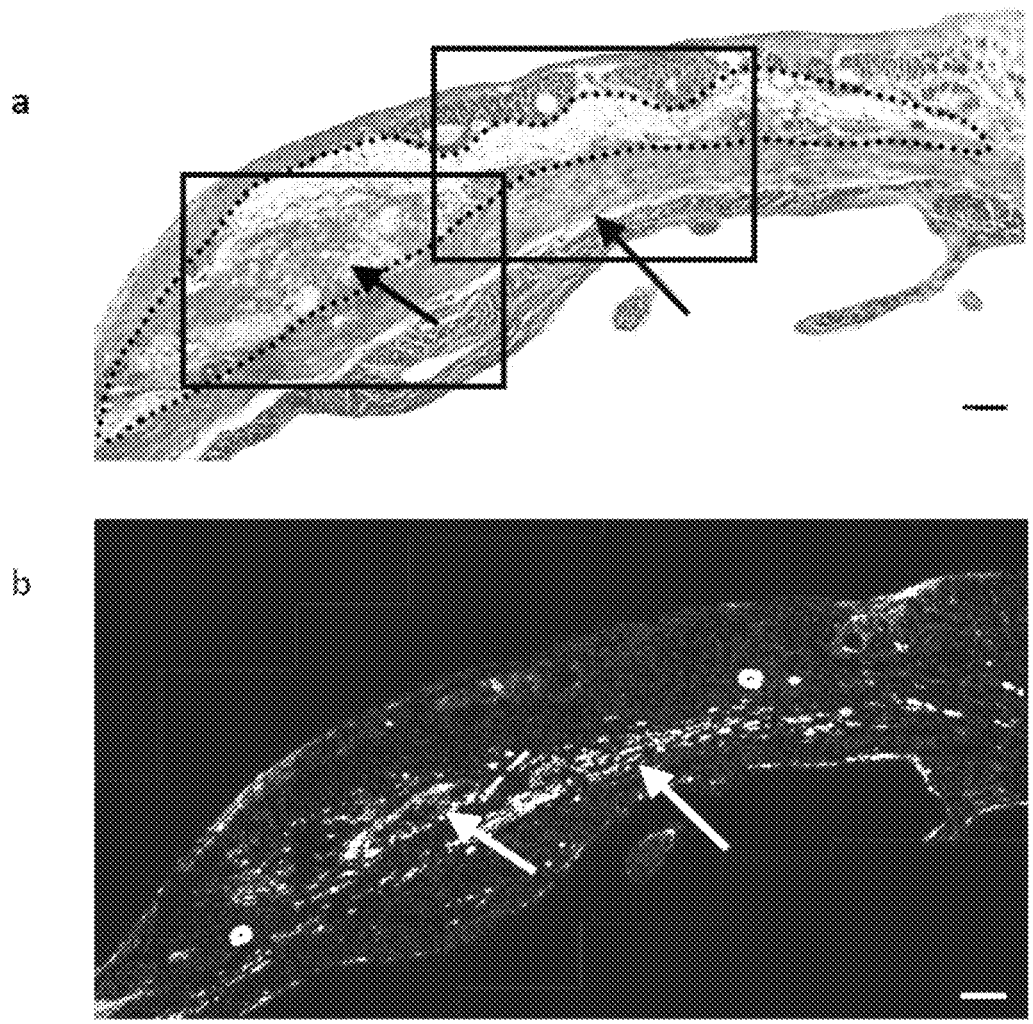
FIG. 10. Higher magnification of (a) H&E staining and (b) immunohistochemical staining in the hydrogel injected ventricular wall of sequential sections. Black dots indicate the injected hydrogel area and blue box indicates higher magnification area shown in FIG. 11 (a). α-SMA staining appears green and nuclear staining appears blue (b). Black and white arrows in (a) and (b) respectively indicate tissue ingrowth in the hydrogel area, while blue arrows in (a) and (b) indicate smooth muscle populated area beneath the hydrogel area. Scale bars: 100 μm.
Figure 11:
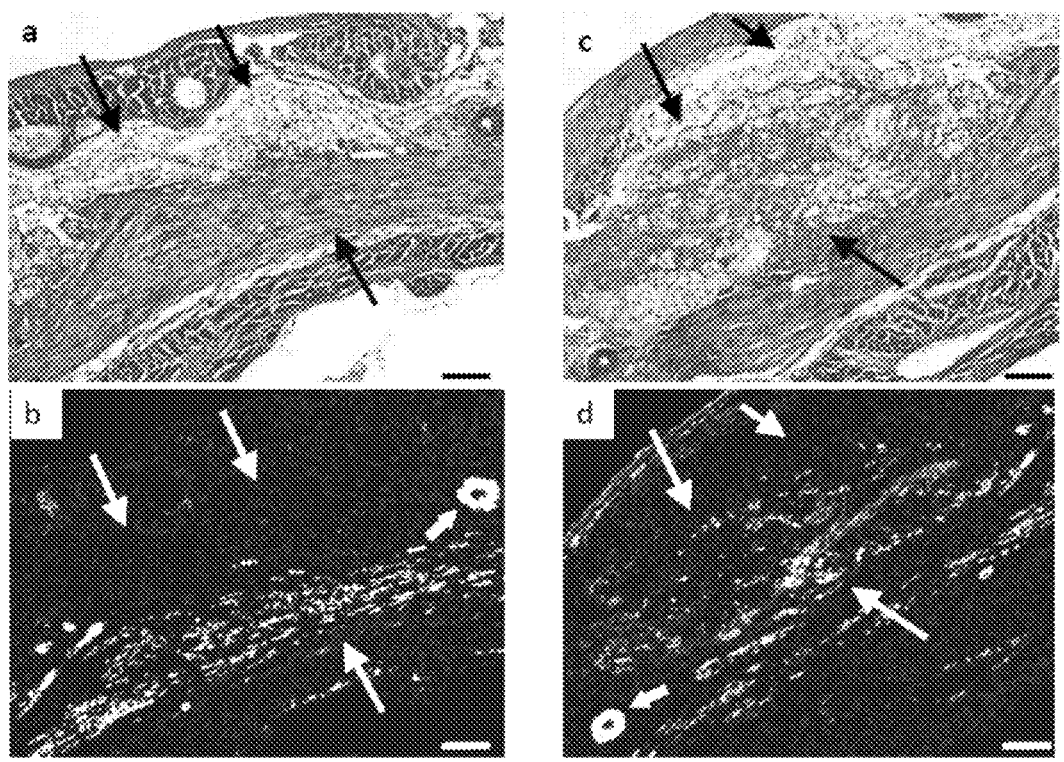
FIG. 11. (a) H&E staining and (b) immunohistochemical staining in the left blue boxed area from FIG. 10. (c) and (d) represent the same staining order for the right blue boxed area from FIG. 10. α-SMA staining appears green and nuclear staining appears blue. Black (a, c) and white (b, d) arrows denote the injected hydrogel area. Blue (a, b, c, d) arrows indicate muscle-like tissue positively staining for α-SMA. Green (a, c) and yellow arrows (b, d) show relatively large arteries with smooth muscle cell walls. Scale bars: 100 μm.

In vitro degradation of the poly(NIPAAm-co-AAc-co-HEMAPTMC) (86/4/10) hydrogel occurred over more than 5 months (FIG. 6b), while in vitro results with the HEMAPLA containing hydrogel occurred in 20 days (Guan J, et al. Biomacromolecules 2008; 9: 1283-92). A specific set of experiments was not performed to determine how fast the PTMC residue was cleaved in PBS solution. Instead, the degradation rate of the hydrogel in PBS, in terms of weight loss, was studied since this is of primary interest with respect to the application. It can be inferred from the degradation test results presented in FIG. 6b that after incubation in PBS for five months, more than 80% of the macromolecules of the hydrogel had their PTMC residues cleaved to an extent that allowed the remaining copolymer to become soluble. The speed of the cleavage of the PTMC residue in PBS would be expected to occur on this same time scale of several months. In vivo, the poly(NIPAAm-co-AAc-co-HEMAPTMC) hydrogel was found to be present in the rat ventricular wall injection region at the 8 week post-injection time point utilized in this study (FIGS. 9 and 10). These experiments showed that the hydrogel had abundant cellular ingrowth in the infarcted myocardial injection site and it is anticipated that the hydrogel in vivo would be degraded faster than in vitro, due to macrophage phagocytic and secretory activity leading to faster hydrolytic cleavage and local removal. The hydrogel showed no in vitro cytotoxicity as evaluated by the cell metabolic viability test, as was the case for the previous hydrogel. As for mechanical properties, the poly(NIPAAm-co-AAc-co-HEMAPTMC) hydrogel was found to be a robust material which could be handled and stretched, as shown in FIG. 5.

For therapeutic cardiac wall injection therapy, it has been reported that injection of a fibrin-alginate biocomposite into damaged myocardium showed an increase in LV wall thickness and prevented infarct expansion (Mukherjee R, et al. Ann Thorac Surg 2008; 86: 1268-77 and Yu J, et al. J Thorac Cardiovasc Surg 2009; 137: 180-7). While alginate alone has been shown to have functional benefit, recent reports of adhesion peptide modified alginate injection do not demonstrate a clear functional benefit of such modification (Tsur-Gang 0, et al. Biomaterials 2009; 30: 189-95 and Yu J, et al. Biomaterials 2009; 30: 751-6). Self-assembling synthetic hydrogels (Jiang X J, et al. J Biomed Mater Res A 2008 (in press, doi 10.1002/jbm.a.32118) as well as self-assembling peptides carrying specific growth factors have been reported to have beneficial effects on the cardiac wall remodeling process (Hsieh P C, et al. J Clin Invest 2006; 116: 237-48). These latter materials have also been reported as vehicles for the transplantation of skeletal myoblasts into the cardiac wall (Dubois G, et al. J Biomed Mater Res B Appl Biomater 2008; 87: 222-8). Regarding thermoresponsive polymers, a recent report showed that injection of a PNIPPAm-based polymer four days following MI in a rabbit model prevented adverse cardiac remodeling and dysfunction at 30 days following treatment (Wang T, et al. Eur J Heart Fail 2009; 11: 14-9). While similar to the current report, some important differences should be noted. The PNIPPAm-based polymer in the study by Wang et al., was injected earlier in the post-infarct period and at the 30 day follow-up time point no materials appeared to be present at the injected positions (Wang T, et al. Eur J Heart Fail 2009; 11: 14-9). Here, poly(NIPAAm-co-AAc-co-HEMAPTMC) (86/4/10) injection was performed two weeks post-MI, corresponding to the beginning of the fibrotic phase of remodeling and after the necrotic phase (Holmes J W, et al. Annu Rev Biomed Eng 2005; 7: 223-53). This time lag may better represent infarcts that would be encountered in patients with sub-acute MI, where the patient may not present clinically until substantial wall remodeling has already occurred (Goldstein S, et al. Cardiol Clin 1998; 16: 623-32). Furthermore, our objective was to have the hydrogel remain over an extended period in the cardiac wall since the remodeling process and the risk for negative remodeling would seem likely to extend beyond the first few weeks. While this has not been demonstrated as beneficial (extended follow up evaluation would be required), we have shown positive effects on function at 8 weeks and the presence of hydrogel remnants at the 8 week time point.

A cellular layer was found at 8 weeks in association with the hydrogel injection area that stained positively for alpha-smooth muscle actin and had co-localized staining for caldesmon, calponin, SM 22α, and SMMHC type II. This staining pattern is consistent with contractile smooth muscle cells. Ultrastructurally mature smooth muscle cells with a contractile phenotype have previously been reported in a rat MI model following treatment with an anti-apoptotic agent (Hayakawa K, et al. Circulation 2003; 108: 104-9). In that study it was hypothesized that apoptosis inhibition would preserve granulation tissue and result in beneficial effects on cardiac remodeling and function. We also previously reported finding smooth muscle cells with a contractile phenotype beneath an elastic, biodegradable poly(ester urethane)urea patch placed onto rat infarcts (Fujimoto K L, et al. J Am Coll Cardiol 2007; 49: 2292-300). These two previous reports may suggest a role for biomaterial-stimulated inflammatory processes in triggering the appearance of these smooth muscle cells, or possibly an effect associated with the alteration of the mechanical environment of the infracted wall. The direct benefit of these smooth muscle cells has not been shown, although their presence contributes to increasing wall thickness.

Conclusions

A biodegradable monomer, HEMAPTMC, was synthesized and used as a labile element within a thermoresponsive hydrogel, poly(NIPAAm-co-AAc-co-HEMAPTMC). Monomer feed ratios were optimized to make the hydrogel both gellable and ultimately bioabsorbable at body temperature (37° C.). The selected poly(NIPAAm-co-AAc-co-HEMAPTMC) (86/4/10) had attractive mechanical properties, exhibited mass loss in vitro over a 20 week period and did not exhibit cytotoxicity. In evaluating this hydrogel in the cardiac injection application for which it was designed, injection of the material prevented ventricular dilation and improved contractile function in a chronic rat infarction model. This composition will be evaluation further as a potential treatment for ischemic cardiomyopathy.

A copolymer comprising an N-alkyl acrylamide residue (e.g., N-isopropylacrylamide), acrylic acid and carbonate bond-containing macromer is provided. The carbonate-bond-containing macromer can be a reaction product of HEMA (hydroxyethyl methacrylate) and an alkyl carbonate (e.g., TMC) with the ratio of alkyl-carbonate to HEMA being greater than 1 (AC:HEMA >1) being preferred in many instances. NIMAAm-co-AAc-co-HEMATMC is shown in the examples to have a structure of about 86/4/10 or 87/3/10, though variations in this ratio are contemplated, such as, for example: approximately 1%, 5%, 10%, 15%, 20% and 25% variations in the NIPAAm:AAc ratio, such as ranging from about 85/5/10 to about 87/3/10 may find use in tissue regeneration applications.

The copolymer preferably has an LCST below 37° C., for example, ranging from between 25° C. or 30° C. to about 35° C., which is readily determined using the methods described herein, e.g., by UV optical absorption at 500 nm.

As shown herein, the copolymer composition finds use in cardiac remodeling, such as in ischemic cardiomyopathy—illustrating excellent results in this application, though other tissue remodeling uses are contemplated. Thus provided are methods of repairing tissue comprising using the copolymer composition as a growth scaffold in vivo or in vitro, to which cells, such as a patient's cells can be added.

Example 2

A Thermally Responsive Injectable Hydrogel Incorporating Methacrylate-polylactide for Hydrolytic Lability To overcome the limitations associated with previous NIPAAm copolymers utilizing HEMA-based co-monomers for hydrolytic lability, our objective was to synthesize a non-HEMA-based biodegradable monomer, methacrylate-polylactide (MAPLA), which would present highly hydrophilic carboxylate groups upon hydrolysis of the PLA segments and does not contain the acrylic acid residues. The MAPLA monomer was then used as the basis for the development of bioabsorbable and thermally responsive NIPAAm-based copolymer hydrogels. Copolymers were synthesized using monomer NIPAAm, HEMA and MAPLA at three different monomer ratios. The resulting hydrogels were characterized in terms of their composition and thermal, mechanical, hydrolytic and cytocompatability properties.

Methacrylate-polylactide (MAPLA), with an average 2.8 lactic acid units, was synthesized and copolymerized with n-isopropylacrylamide (NIPAAm) and 2-hydroxyethyl methacrylate (HEMA) to obtain bioabsorbable thermally responsive hydrogels. Poly(NIPAAm-co-HEMA-co-MAPLA) with three monomer feed ratios (84/10/6, 82/10/8 and 80/10/10) was synthesized and characterized with NMR, FTIR and GPC. The copolymers were soluble in saline at reduced temperature (<10° C.), forming clear solutions that increased in viscosity with the MAPLA feed ratio. The copolymers underwent sol-gel transition at lower critical solution temperatures of 12.4, 14.0 and 16.2° C. respectively and solidified immediately upon being placed in a 37° C. water bath. The warmed hydrogels gradually excluded water to reach final water contents of ~45%. The hydrogels as formed were mechanically strong, with tensile strengths as high as 100 kPa and shear moduli of 60 kPa. All three hydrogels were completely degraded (solubilized) in PBS over a 6-8 month period at 37° C., with a higher MAPLA feed ratio resulting in a faster degradation period. Culture of primary vascular smooth muscle cells with degradation solutions demonstrated a lack of cytotoxicity. The synthesized hydrogels provide new options for biomaterial injection therapy where increased mechanical strength and relatively slow resorption rates would be attractive.

Materials and Methods

All chemicals were purchased from Sigma-Aldrich unless otherwise stated. NIPAAm was purified by recrystallization from hexane and vacuum dried. 2-hydroxyethyl methacrylate (HEMA) was purified by vacuum distillation. Lactide was purified by recrystallization from ethyl acetate. Benzoyl peroxide (BPO), sodium methoxide ($NaOCH_3$) and methacryloyl chloride were used as received.

Synthesis of methacrylate polylactide (MAPLA)

Figure 14:
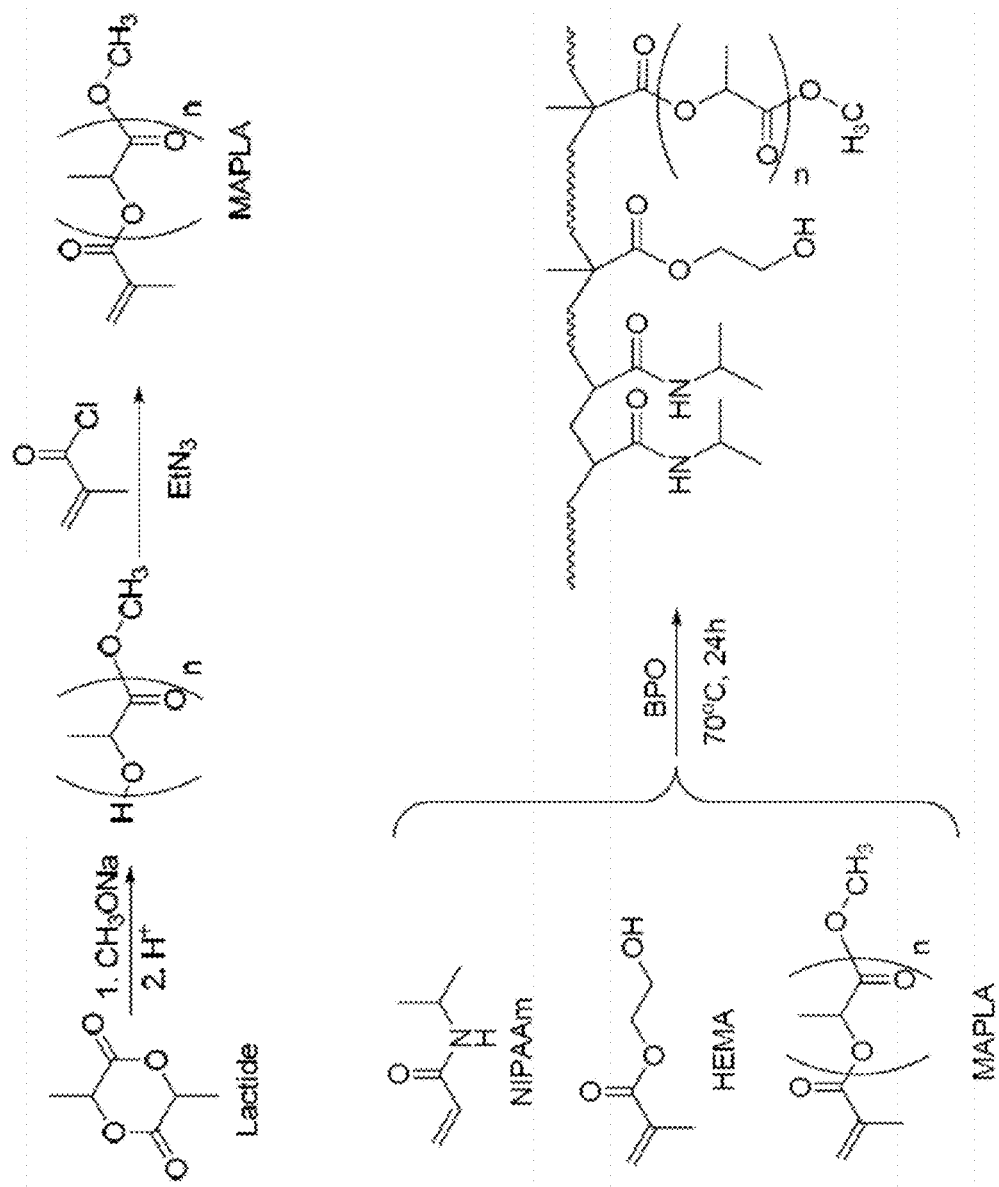
FIG. 14. Synthetic scheme for MAPLA and poly (NIPAAm-co-HEMA-co-MAPLA).

As shown in FIG. 14, polylactide (HO—PLA—$OCH_3$) was synthesized by $NaOCH_3$ initiated ring opening polymerization of lactide. In a lactide solution in dichloromethane a solution of $NaOCH_3$ in methanol (10% wt/v) was added with a molar ratio of ($NaOCH_{3+}HOCH_3$) to lactide of 1:1, under vigorous stirring. The reaction proceeded for 2 h at 0° C. before the solution was rinsed with 0.1M HCl and deionized (DI) water. The organic phase was isolated by centrifugation and dried over anhydrous $MgSO_4$. The solvent (dichloromethane) was removed by rotary evaporation at 60° C. to obtain HO-PLA-$OCH_3$. Biodegradable monomer MAPLA was synthesized by dropping equimolar amounts of methacryloyl chloride into the HO-PLA-$OCH_3$ solution in dichloromethane in the presence of equimolar amounts of triethylamine. After reacting at 0° C. overnight, the solution was filtered to remove precipitants, and was then rinsed sequentially with 0.2M $Na_2CO_3$, 0.1M HCl and DI water. The organic phase was isolated by centrifugation and dried over anhydrous $MgSO_4$. The solvent (dichloromethane) was removed by rotary evaporation at 40° C. to get the raw product of MAPLA, which was finally purified by flash chromatography.

Synthesis of poly(NIPAAm-co-HEMA-co-MAPLA)

Poly(NIPAAm-co-HEMA-co-MAPLA) copolymers were synthesized by free radical polymerization (FIG. 14). Monomers (NIPAAm, HEMA, MAPLA) were dissolved in 1,4-dioxane to form a 5 wt % solution containing BPO ($7.2 \times 10^{-3}$ mol/mol monomer). The polymerization was carried out at 70° C. for 24 h under argon atmosphere. The copolymer was precipitated in hexane and further purified by precipitation from THF into diethyl ether and vacuum dried.

Characterization $^1$H-NMR and $^{13}$C-NMR spectra of MAPLA and the poly (NIPAAm-co-HEMA-co-MAPLA) copolymers were recorded with a 300 MHz BRUKER spectrometer using $CD_3Cl$ or DMSO-$d_6$ as a solvent. The mass spectrum of MAPLA was recorded on an HP 1100 Series LC/MSD instrument with an API-ES positive ionization method. Fourier transform infrared (FTIR) spectra of the copolymers were obtained with a Nicolet FTIR spectrometer, with samples prepared by coating a 1% copolymer solution onto a NaCl window. Molecular weight of the copolymers was determined by gel permeation chromatography (GPC, Waters Breeze System, Waters 1515 HPLC Pump, Waters 2414 differential refractometer). The copolymers were dissolved in THF at a concentration of 1 mg/mL and the GPC analyses were performed at 35° C. A poly(methyl methacrylate) standard kit (Fluka, ReadyCal Set $M_p$ 500-2,700,000) was used for molecular weight-elution volume calibration.

LCSTs of the copolymer solutions in PBS (16.7 wt %, pH 7) were studied by measuring optical absorption at 500 nm over a temperature range of 0 to 25° C. The LCST of each copolymer was determined (n=4) by determining the temperature at which the absorbance of the copolymer solution reached half of its maximal value, during the phase transition. Differential scanning calorimetry (DSC-60; Shimadzu) was also used to characterize the LCST behavior of the copolymer solutions with a scanning rate of 5° C./min over a range of 0 to 40° C. The temperature at the maxima of the endotherm peak was recorded as the LCST (Feil, H.; Bae, Y. H.; Feijen, J.; Kim, S. W. *Macromolecules* 1993, 26, 2496-2500).

Rheology studies were conducted on a TA Instrument rheometer (AR2000). Copolymer solution viscosities at 10° C. were measured with a shear rate sweep (0-10 $sec^{-1}$). To observe the mechanical property change of the hydrogels during the temperature induced sol-gel transition, the polymer solutions (16.7 wt % in PBS) were placed between two parallel plates. With temperature sweep from 10 to 45° C. and a heating rate of 4° C./min, the shear storage modulus G' and the loss modulus G" were collected as a function of temperature at a fixed strain of 2% and a frequency of 1 Hz.

To measure the mechanical properties of the hydrogels, samples were incubated in a 37° C. water bath for 24 h to reach stable water contents, and then the solid hydrogels were placed between two parallel plates and the G' and G" were measured at 37° C. with a fixed strain of 5% and a frequency sweep from 0.1 to 2 rad/s. For tensile testing of the hydrogels, samples (n=4 each) were cut into rectangular strips 1 mm thick, 4 mm wide and 25 mm long, and then loaded in a water bath test cell equilibrated to 37±2° C. with preheated grips attached to each sample end. An ATS 1101 Universal Testing Machine equipped with a 101b load cell was utilized with a cross-head speed of 6 cm/min.

The gelation speed of the copolymer solutions (PBS, 16.7 wt %) was measured by incubating 3 mL glass vials containing ~1 mL hydrogel solution in a 37° C. water bath. The water content of the hydrogel at different incubation time points was measured over 24 h. Water content was defined as $(w_2-w_1)/w_2 \times 100\%$, where $w_2$ and $w_1$ are wet mass and dry mass of the hydrogel, respectively. The microstructures of the (80/10/10) hydrogel at the beginning of the gelation process (30 sec) and after 24 hr incubation at 37° C. were imaged by quenching the hydrogels in liquid nitrogen followed by freeze drying, gold sputtering and scanning electron microscopic observation (SEM JEM-1011, JEOL).

Hydrogel degradation was quantified by mass loss measurements. Hydrogels with known initial dry masses (~60 mg) were immersed into 7 mL PBS (pH 7, replaced weekly) at 37° C. At pre-defined time points over an 8 month period the hydrogels (n=3 each) were lyophilized and the relative mass loss recorded.

Cytotoxicity Assay

The cytotoxicity of the hydrogel degradation products was assessed by measuring the relative metabolic viability of cells cultured with medium supplemented with degradation products, as previously described (Fujimoto, K.L.; Ma, Z.; Nelson, D. M.; Hashizume, R.; Guan, J.; Tobita, K.; Wagner, W. R. *Biomaterials* 2009, 30, 4357-4368; Guan, J.; Hong, Y.; Ma, Z. Wagner W R. *Biomacromolecules* 2008, 9, 1283-92; and Vihola, H.; Laukkanen, A.; Valtola, L.; Tenhu, H.; Hirvonen, J. *Biomaterials* 2005, 26, 3055-3064). The hydrogel degradation solution was prepared by hydrolysis of the hydrogel in 1.0 M NaOH, followed by removal of NaOH using a cationic ion-exchange resin (Amberlite IR-120H, Aldrich) and supplementing with a 10×EMEM culture medium (BioWhittaker, Lonza) at a volume ratio of 1:9 with respect to the hydrogel degradation solution. Rat vascular smooth muscle cells (RSMCs) were isolated according to Ray, J. L.; et al. (*Methods Cell Sci.* 2001, 23, 185-188). Cells were cultured in Dulbecco's modified Eagle medium (DMEM) supplemented with 10% fetal bovine serum (FBS) to the fifth passage and seeded into a 24-well tissue culture plate at a seeding density of 15,000/well. The hydrogel degradation supplemented with EMEM was added into each well to obtain a final concentration of 5 mg/mL. Culture medium without added degradation solution was used as a control. Cell metabolic activity was measured (n=4 each) using an MTS assay kit (Promega Cell-Titer 96® Cell Proliferation Assay) to quantify mitochondrial activity. To qualitatively verify the results of the above test, cells were also observed under fluorescence microscopy after live/dead staining with a Promokine® Live/Dead Cell Staining Kit.

Statistics

Data are expressed as means with the standard deviation. Analyses utilized SPSS software (SPSS Inc, Chicago Ill.). Statistical analyses were performed by one-way ANOVA followed by Tukey's post-hoc testing. Statistical significance was considered to exist at p<0.05.

Results

Synthesis

Figure 15A:
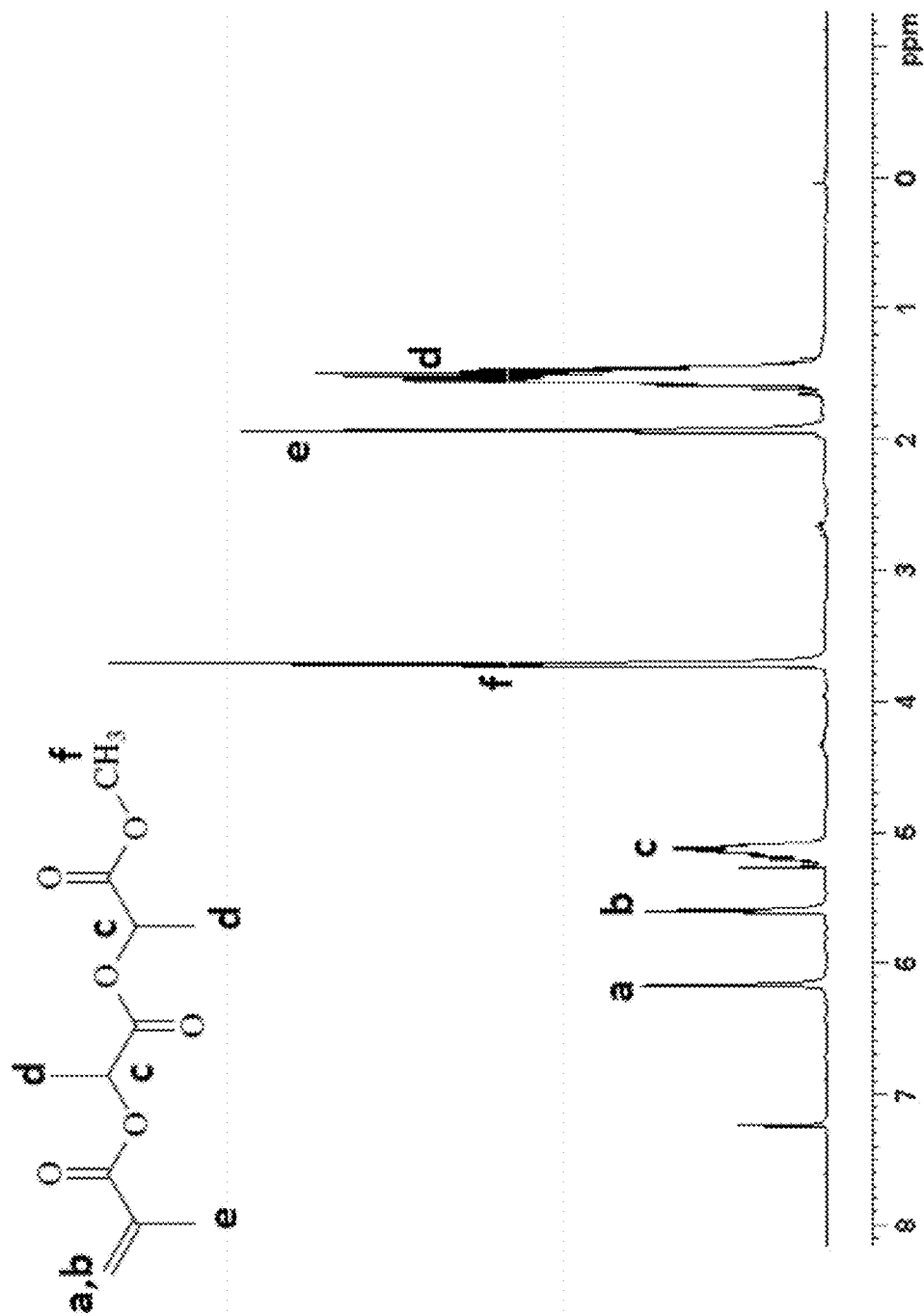
(FIG. 15A) $^1$H-NMR and (FIG. 15B) $^{13}$C-NMR spectra for MAPLA.
Figure 15B:
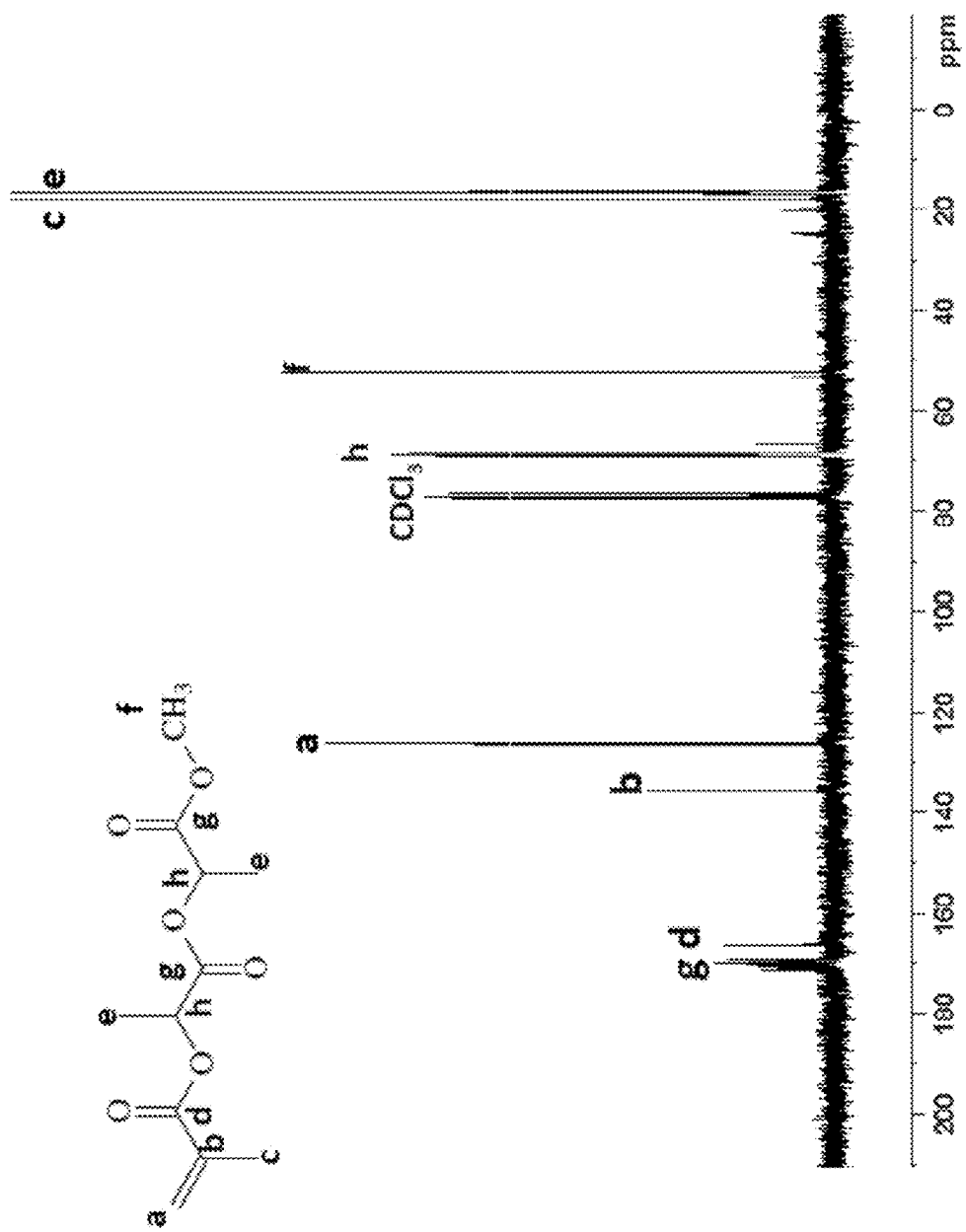
FIG. 15.

The synthesis of MAPLA was confirmed by $^1$H-NMR (FIG. 15a) and $^{13}$C-NMR spectra (FIG. 15b) which contained proton peaks and carbon peaks in agreement with the molecular structure of MAPLA. The chemical structure of MAPLA was also confirmed by the mass spectrum (API-ES positive ionization). Peaks at 267.0 (MAPLA2+Na$^+$), 339.0 ((MAPLA3+Na$^+$), 411.0 (MAPLA4+Na$^+$), 483.0 (MAPLA5+Na$^+$) and 555.2 (MAPLA6+Na$^+$) were observed, indicating that the product was a mixture of molecules containing different PLA lengths. The number average length of PLA units per monomer was determined from $^1$H-NMR spectrum (FIG. 15a) as 2.8 by calculation from the ratio of the integrals of hydrogen peaks from PLA (peaks c) and the peaks from the hydrogens bordering the double bond (CH2=) (peaks a and b).

Figure 16:
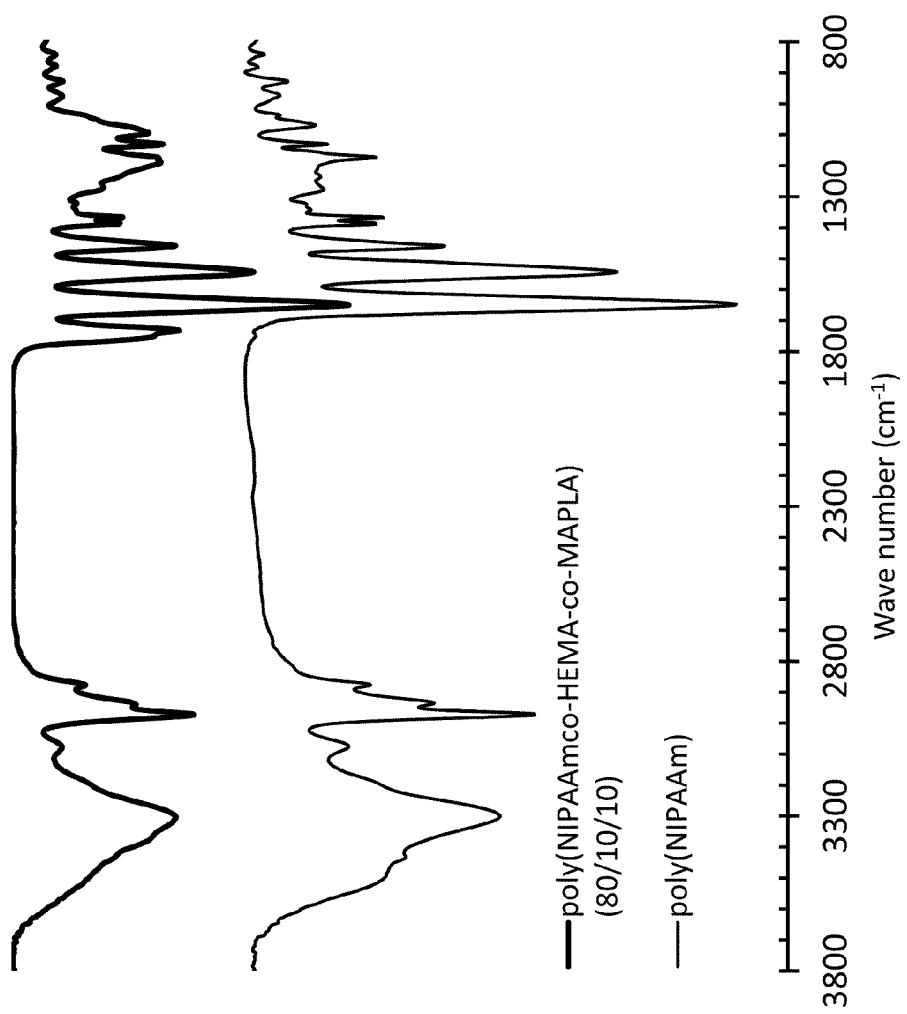
FIG. 16. FTIR spectra of poly(NIPAAm) and poly (NIPAAm-co-HEMA-co-MAPLA).
Figure 17A:
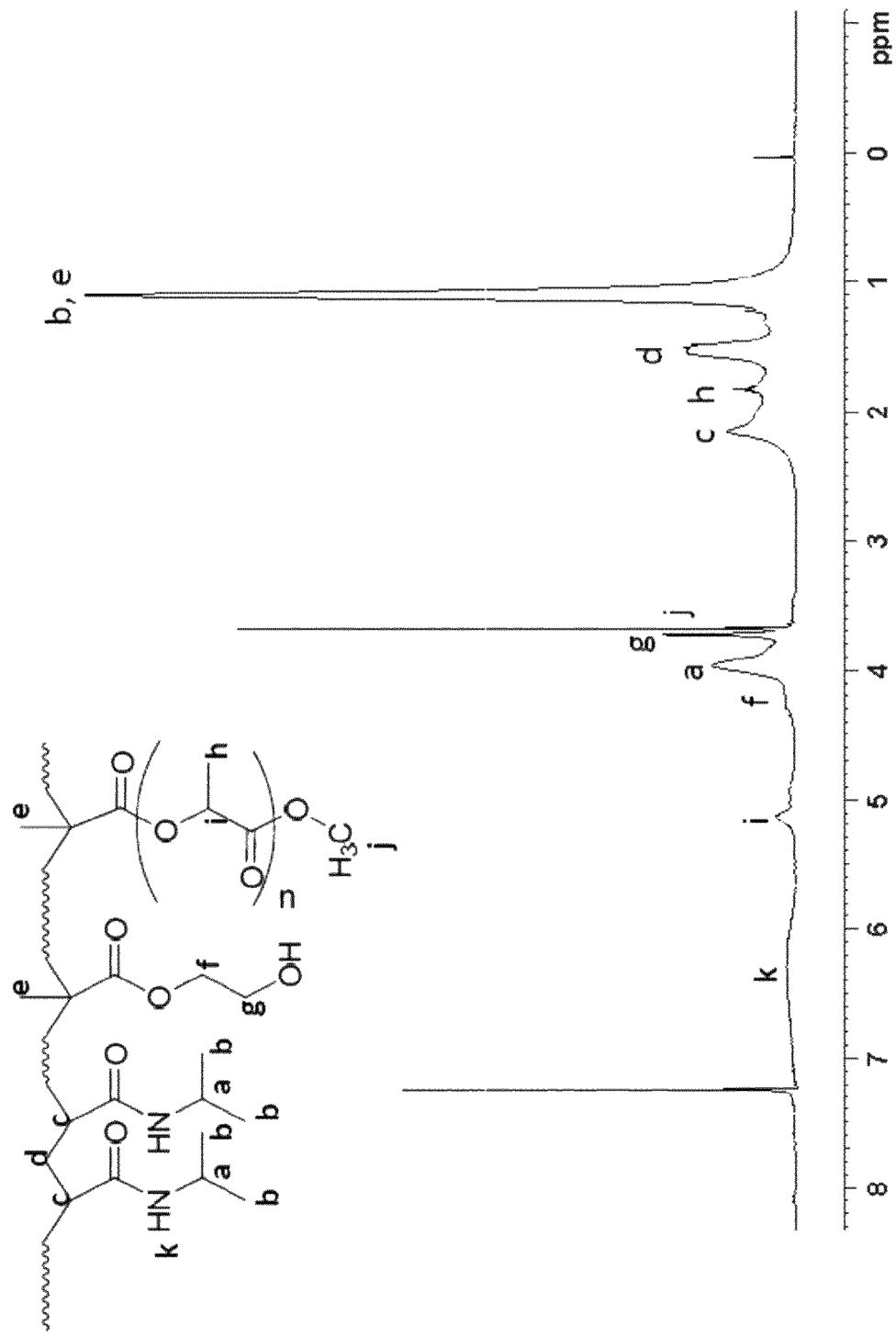
(FIG. 17A) $^1$H-NMR and (FIG. 17B) $^{13}$C-NMR spectra for poly(NIPAAm-co-HEMA-co-MAPLA) (80/10/10)
Figure 17B:
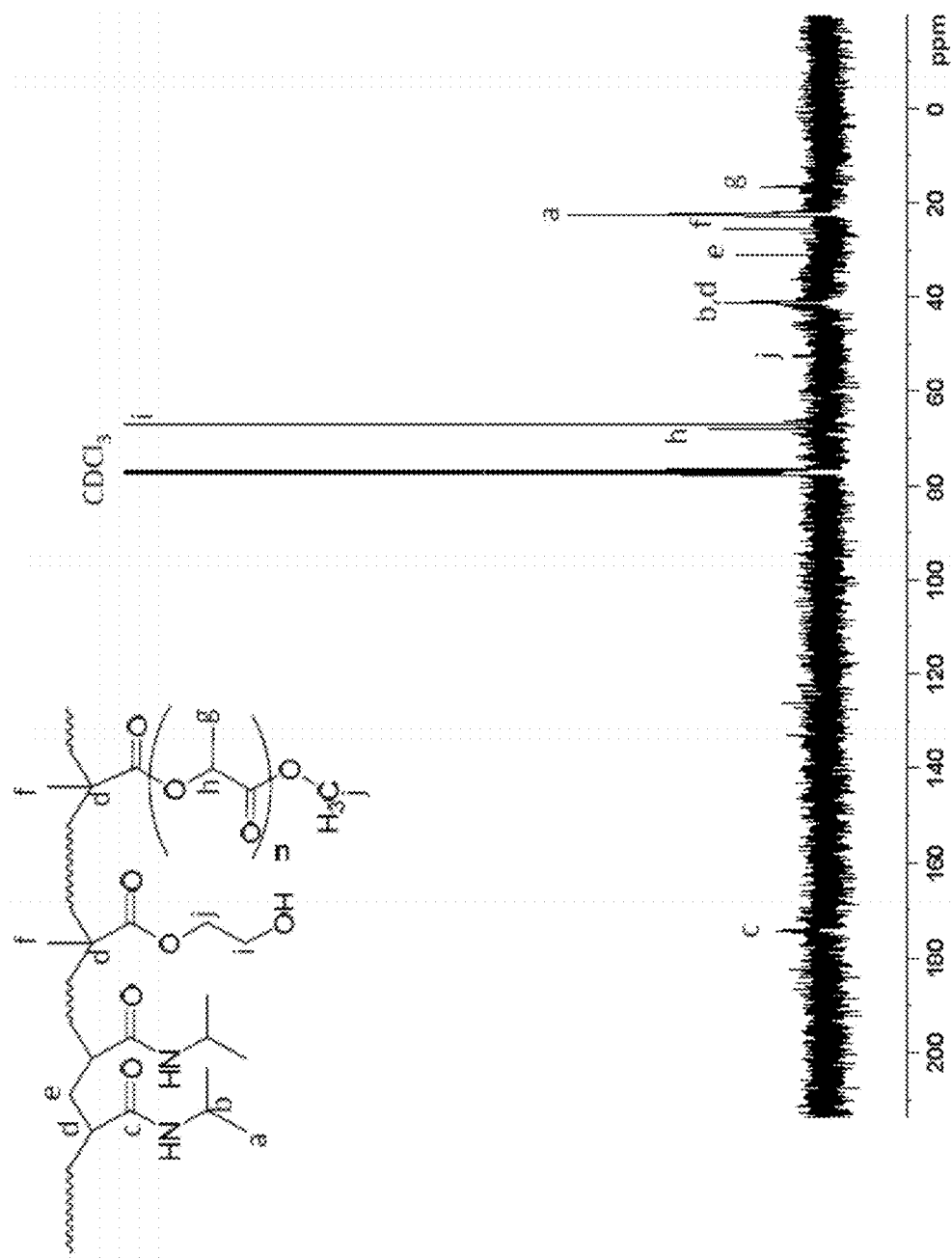
FIG. 17.

Copolymers with different monomer ratios were prepared by free radical polymerization. Table 3 summarizes poly (NIPAAm-co-HEMA-co-MAPLA) copolymers synthesized with three different MAPLA feed ratios. All of the copolymers had molecular weights between 20 and 30 k, and a polydispersity index of 1.5-2.0. FTIR spectra of the copolymer (FIG. 16) exhibited an amide I peak at 1550 and an amide II peak at 1650 $cm^{-1}$ characteristic of NIPAAm and also a strong peak at 1730 $cm^{-1}$ for the —C=O of the ester groups from HEMA and MAPLA. FIG. 17 shows typical $^1$H-NMR and $^{13}$C-NMR spectra for a synthesized copolymer. Proton and carbon peaks characteristic of NIPAAm and MAPLA are seen and the ratio of MAPLA to NIPAAm in the copolymer was obtained by peak area integration of these characteristic peaks at 5.1 ppm and 3.8 ppm, respectively (Table 3). The MAPLA monomer ratios in the copolymers were found to be lower than their feed ratios, indicating that the polymerization rate of MAPLA was lower than that for NIPAAm under the polymerization conditions evaluated.

Gelation Process

Figure 18A:
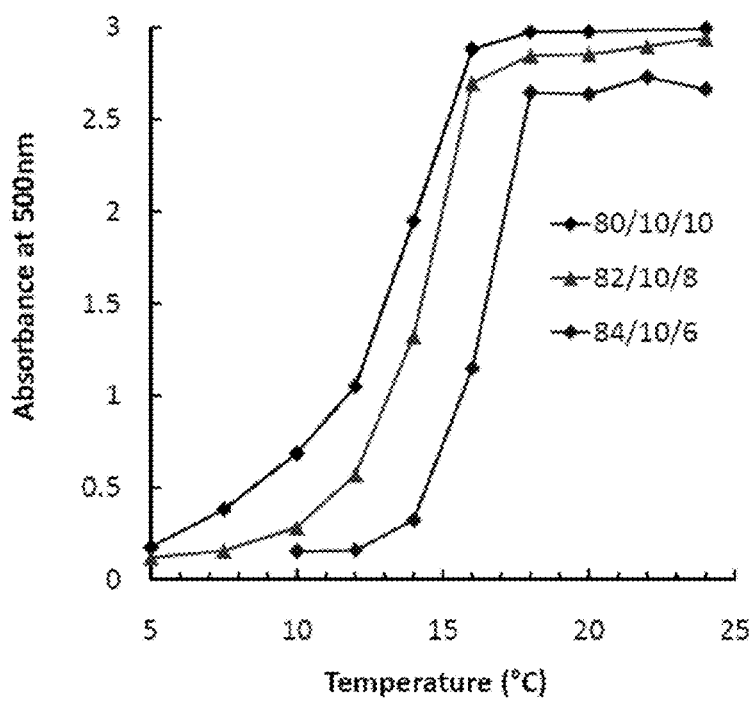
FIG. 18. LCST determination by (FIG. 18A) measurement of copolymer solution optical absorption.
(FIG. 18B) measurement of shear modulus on a rheometer, 1 Hz, 2% strain.
(FIG. 18C) DSC analysis, 5° C./min.

The phase transition behavior at the LCST was examined through real-time screening of the optical, mechanical and thermal properties of the hydrogel solutions (16.7 wt % in PBS) during temperature changes. Representative optical absorption curves of the hydrogel solutions (80/10/10, 82/10/8 and 84/10/6) are shown in FIG. 18A and the calculated LCSTs are summarized in Table 3. Hydrogel LCSTs decreased with increasing MAPLA feed ratios. The same phenomenon and relative order of response was also observed by measuring the mechanical property (G' and G") change of the hydrogels with increasing temperature, with typical curves shown in FIG. 18B. Typical DSC curves (FIG. 18C) showed broad but obvious endothermal peaks at 21-22° C., corresponding to the LCSTs, but the relative order of these curves varied and this technique did not provide consistently different responses between the hydrogels.

TABLE 3

Poly(NIPAAm-co-HEMA-co-MAPLA) copolymers with different monomer molar feed ratios.

| Monomer Feed ratio NIPAAm/HEMA/ MAPLA | yield | Mn | Mw/ Mn | MAPLA/ NIPAAm ratio in Polymer (mole %) | LCST (° C.) by optical method | Hydrogel Water content (%) at 37° C. in PBS |
|---|---|---|---|---|---|---|
| 84/10/6 | 90% | 22K | 1.5 | 4.3 | 16.2 ± 0.2* | 42 ± 0.3 |
| 82/10/8 | 90% | 25K | 1.5 | 5.0 | 14.0 ± 0.2* | 47 ± 0.3 |
| 80/10/10 | 90% | 22K | 1.6 | 6.1 | 12.4 ± 0.4* | 44 ± 0.3 |

*p < 0.001 versus each of other copolymers.

Figure 19:
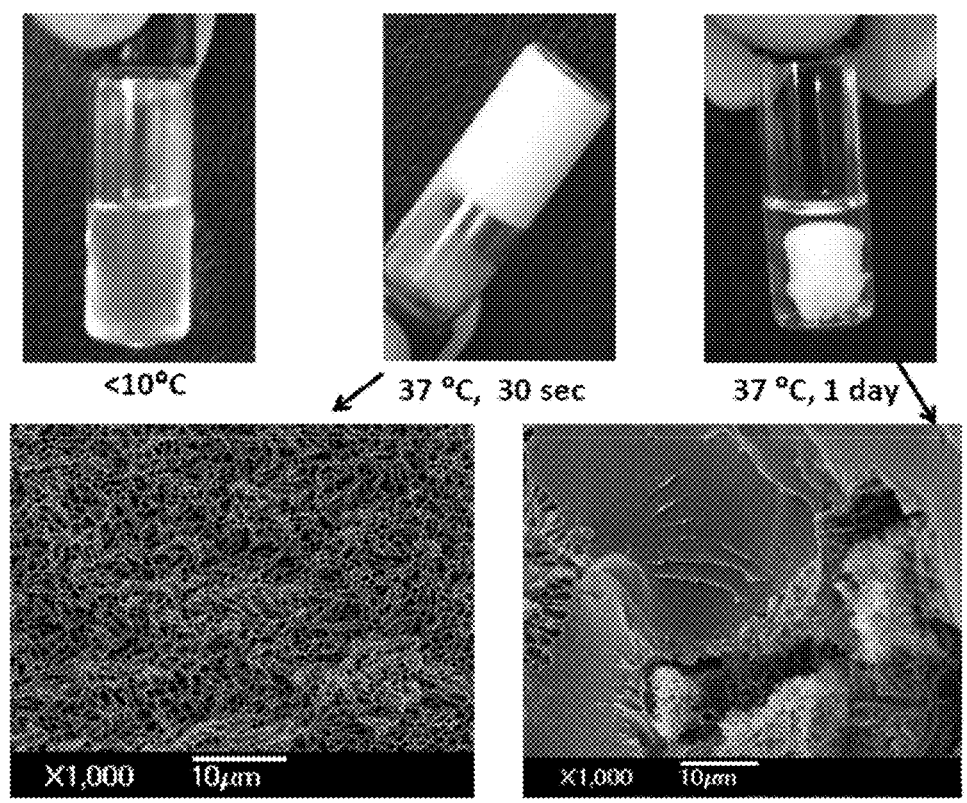
FIG. 19. Gelation process of the poly(NIPAAm-co-HEMA-co-MAPLA) (80/10/10) hydrogel (PBS, 16.7 wt %) and the microstructure of the hydrogel formed at 37° C. after 30 sec and 1 day. Samples were quenched with liquid nitrogen and freeze dried at −40° C.
Figure 20:
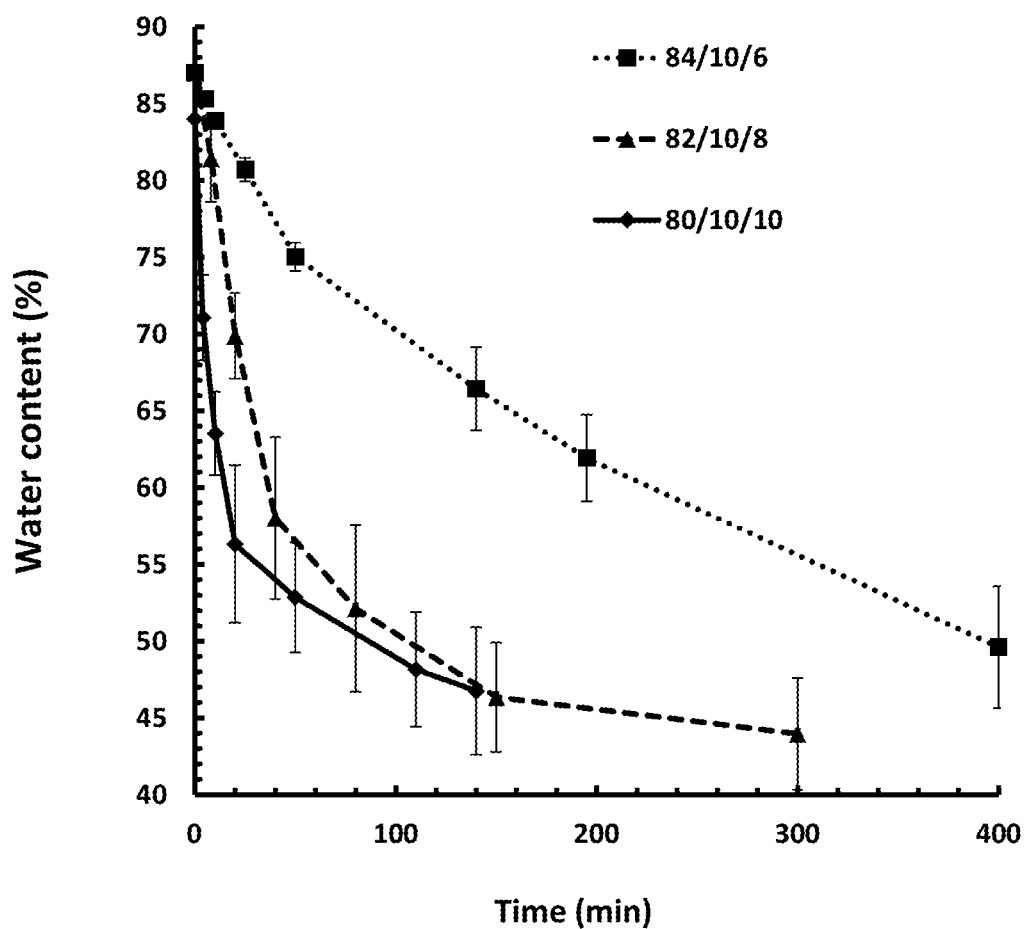
FIG. 20. Gelation of the poly(NIPAAm-co-HEMA-co-MAPLA) hydrogels (PBS, 16.7 wt %). Water contents were plotted against the incubation time of the hydrogels in a 37° C. water bath.

A macroscopic perspective of the poly(NIPAAm-co-HEMA-co-MAPLA) (80/10/10) gelation process is presented in FIG. 19. Immediate sol-gel transition occurred upon the incubation of the solution into a 37° C. water bath within 30 sec (FIG. 19). After that, the hydrogel continued to exclude water gradually to reach a stable size after several hr. The final equilibrated water contents of the hydrogels were measured at ~45% after 24 hr (Table 3). The relative speed of water exclusion during the gelation process is evident by plotting the water content of the hydrogels against the time of the incubation at 37° C., as shown in FIG. 20. Microstructures of the (80/10/10) hydrogel at the beginning of the gelation process (30 sec) and after 24 hr incubation at 37° C. are shown in FIG. 19. The loss of microporosity is evident at the later time point.

Mechanical Properties

Figure 21:
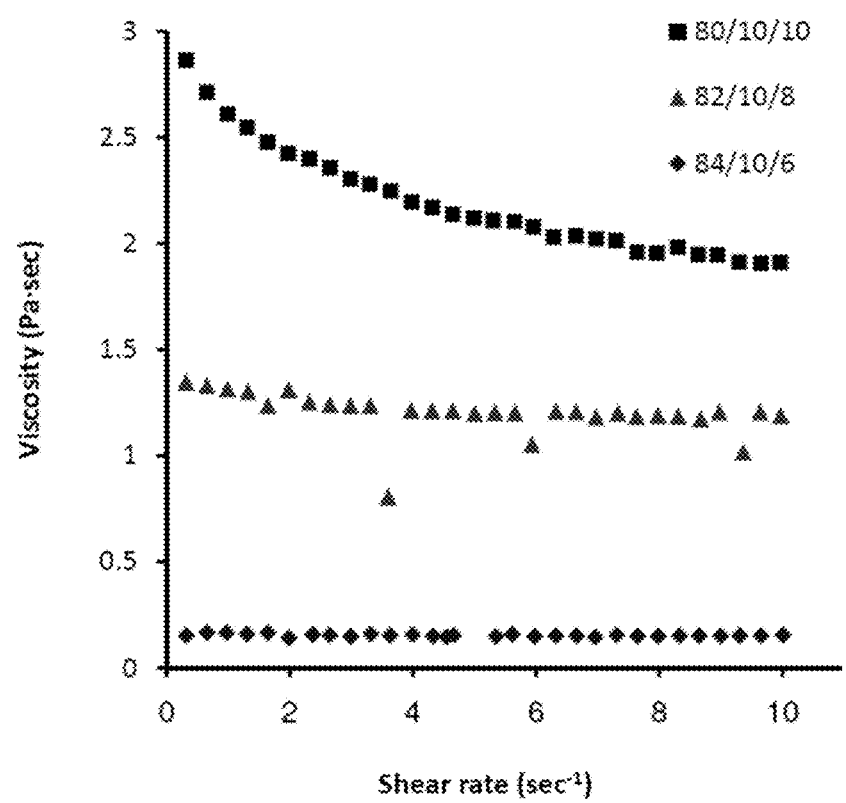
FIG. 21. Viscosity of the poly(NIPAAm-co-HEMA-co-MAPLA) hydrogel solutions (PBS, 16.7 wt %) at 10° C.

At a temperature below the hydrogels' LCST (10° C.), the clear, viscous solutions were observed, with the solution viscosity increasing with the MAPLA feed ratio, as shown in FIG. 21. Since the copolymers all had similar molecular weights (Table 3), the viscosity differences were attributed to the varying hydrophobicity in the different samples, with increased viscosity driven by increased inter-molecular hydrophobic interactions. FIG. 21 also indicates that the viscosities were more shear rate-dependent with increased MAPLA feed ratio.

Figure 22A:
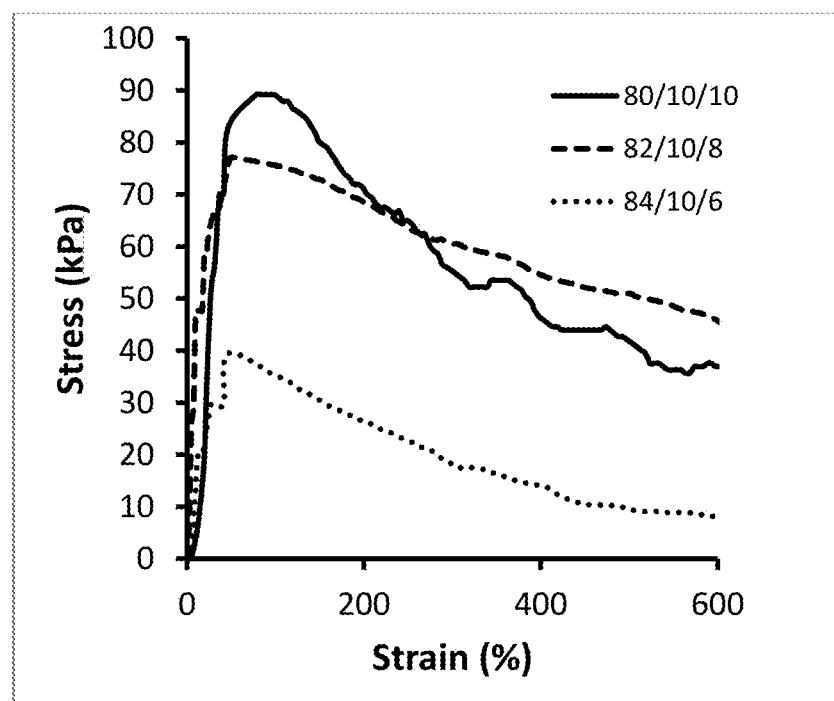
FIG. 22. Tensile curves (FIG. 22A) and maximum tensile strength (FIG. 22B) of the poly(NIPAAm-co-HEMA-co-MAPLA) hydrogels at 37° C. Hydrogels were formed in 37° C. water bath for 24 h.
Figure 22B:
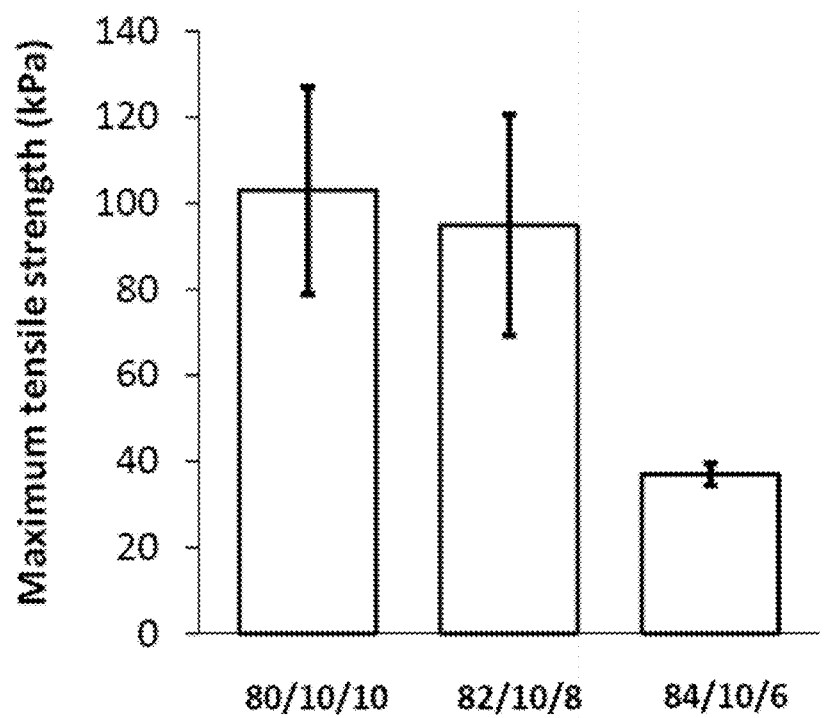
Figure 23:
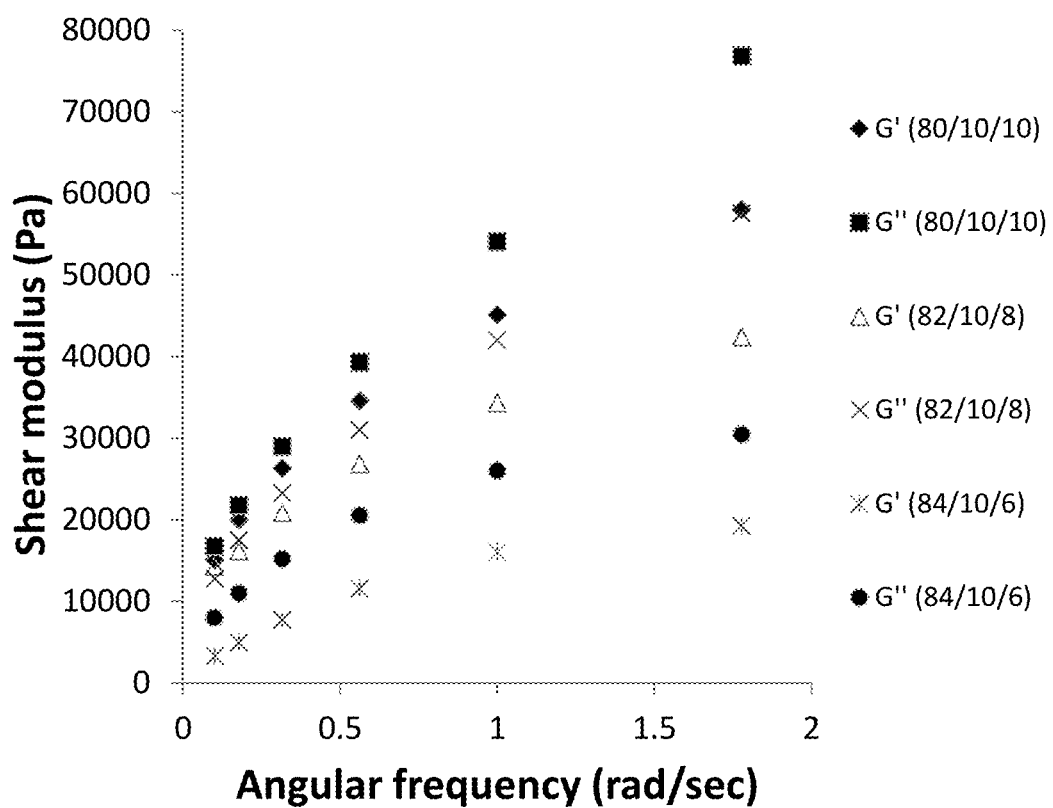
FIG. 23. Dynamic shear modulus of the poly(NIPAAm-co-HEMA-co-MAPLA) hydrogels at 37° C. Strain, 5%. Hydrogels were formed in a 37° C. water bath for 24 hrs.

The final equilibrated hydrogels incubated in PBS at 37° C. after 24 hr were highly flexible gum-like materials with plastic deformation occurring beyond the maximum tensile strength at approximately 60-100% strain, as shown in the tensile curves in FIG. 22. The dynamic shear modulus of the hydrogels at different angular frequencies is shown in FIG. 23. Both the tensile and the shear modulus test showed that the hydrogels' stiffness increased with the MAPLA feed ratio in the copolymer.

Degradation

Figure 24A:
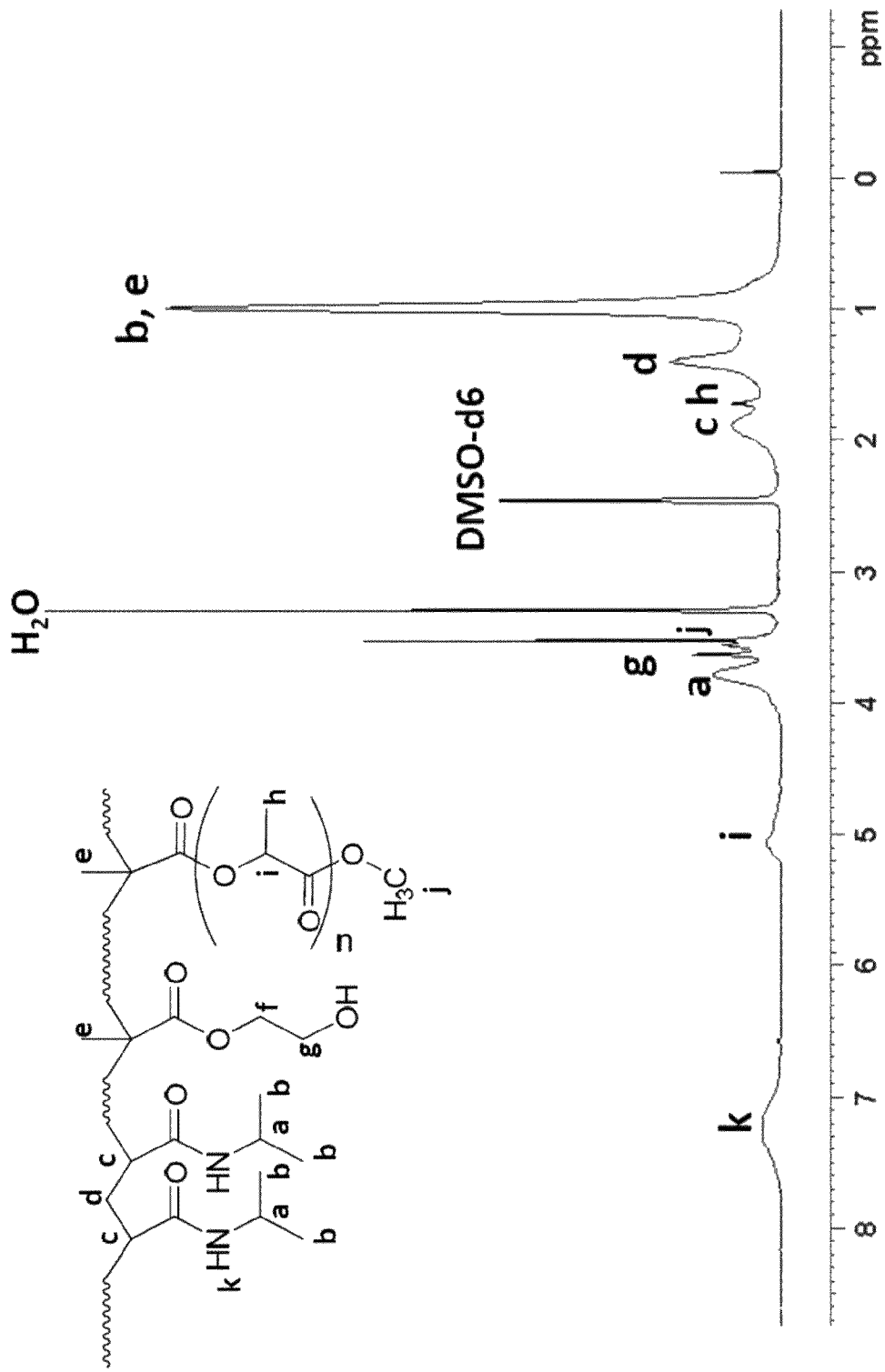
FIG. 24. $^1$H-NMR of poly(NIPAAm-co-HEMA-co-MAPLA) (80/10/10) before (FIG. 24A) and after (FIG. 24B) the removal of PLA by hydrolysis in 1M NaOH.
Figure 24B:
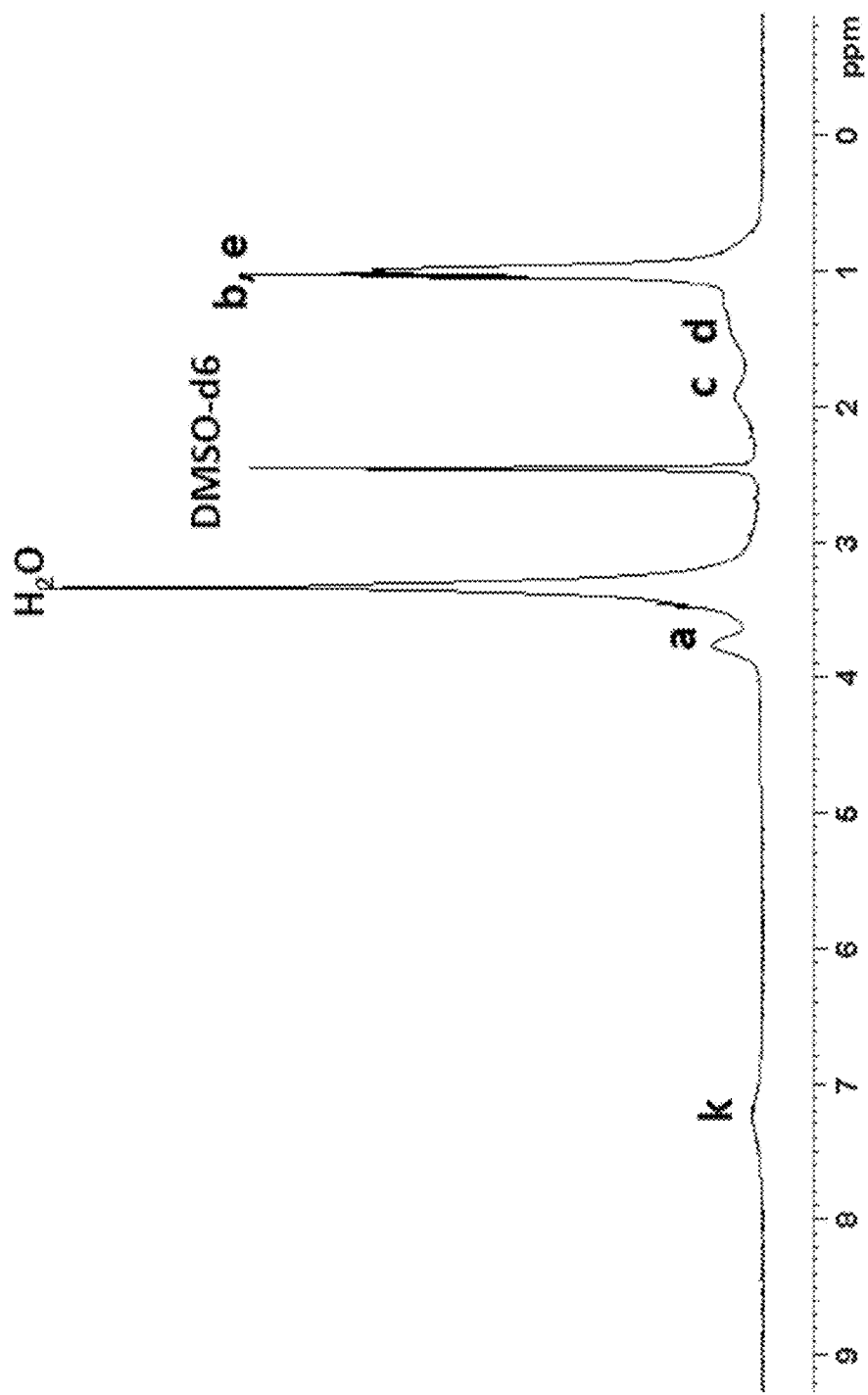

The in vitro degradation properties of the hydrogels with different MAPLA feed ratios were first evaluated by hydrolysis in NaOH (1M) at room temperature for 1 day to theoretically cleave the PLA residues, representing extensive degradation of the copolymer. The $H^1$-NMR spectrum of the hydrolyzed copolymer did not show the peak characteristic of PLA at 5.1 ppm which was found in the NMR spectrum before degradation (FIG. 24). The hydrolyzed copolymers gave clear solutions at 37° C., demonstrating that the LCSTs were well above 37° C. A second evaluation of in vitro degradation of the hydrogel was performed in PBS at 37° C. with the resulting mass loss curve shown in FIG. 25. The hydrogels were gradually solubilized at a much lower rate than in the NaOH solution. For all the three hydrogels, mass loss at 100 days was only about 20%, followed by an accelerated mass reduction during the next 100 days before totally dissolution of the hydrogels in PBS.

Cytotoxicity

Figure 26:
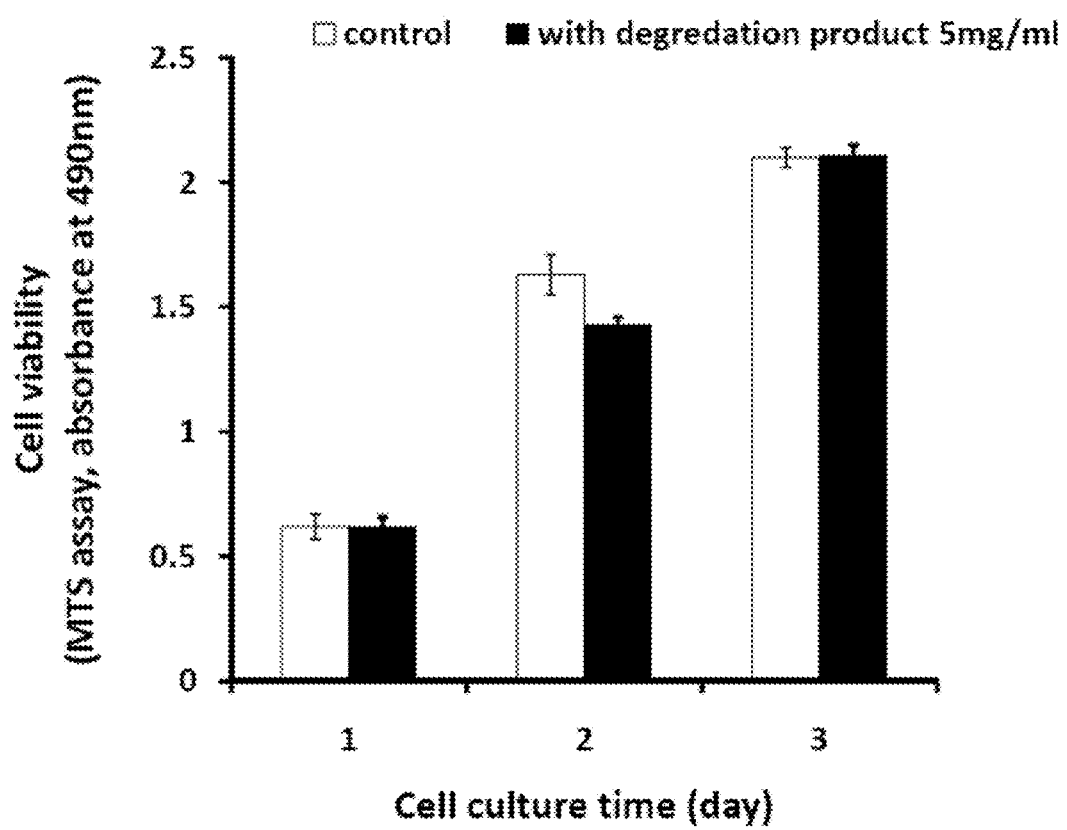
FIG. 26. Cytotoxity assay of poly(NIPAAm-co-HEMA-co-MAPLA) (80/10/10) hydrogel degradation products by cell metabolic activity assessment (MTS assay) for RSMCs cultured on tissue culture polystyrene. Hydrolyzed hydrogel solution was supplemented into cell culture medium at a final concentration of 5.0 mg/mL.
Figure 27A:
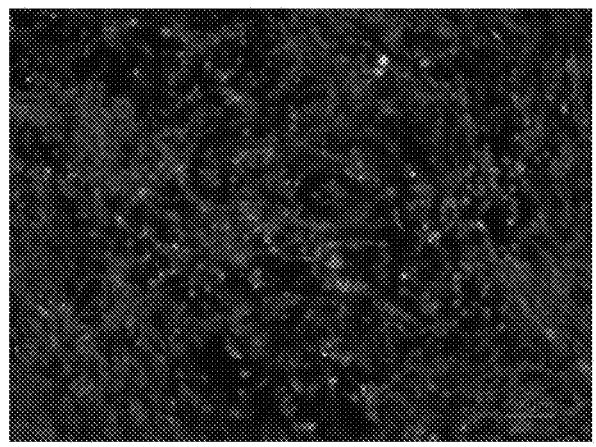
FIG. 27. Live/dead staining of RSMC cultured on tissue culture polystyrene using (FIG. 27A) untreated culture medium and (FIG. 27B) culture medium containing 5.0 mg/mL hydrolyzed poly(NIPAAm-co-HEMA-co-MAPLA) (80/10/10). Observations were recorded at a culture time of 3 days. Scale bar: 100 µm.
Figure 27B:
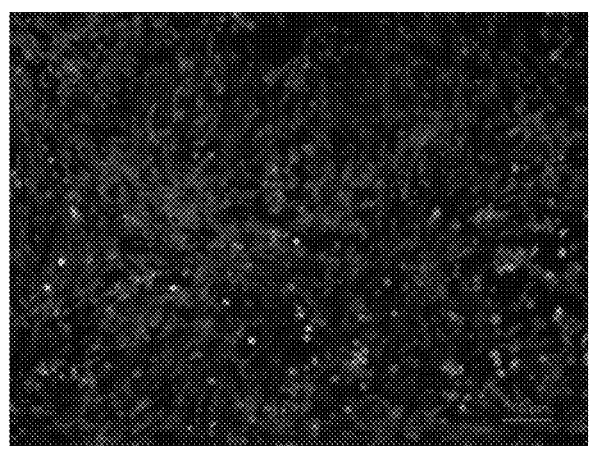

With RSMC mitochondrial activity serving as an indirect index for cell viability, FIG. 26 demonstrates a lack of toxic effect of medium containing degradation and solubilized products on RSMC culture. This result was further verified by fluorescent live/dead staining of RSMC cultured under control or degradation product-containing culture medium (FIG. 27). For both culture media, dead cells (stained red) were seen in low numbers and no difference was found in the relative number of dead cells viewed over several culture wells.

Figure 28A:
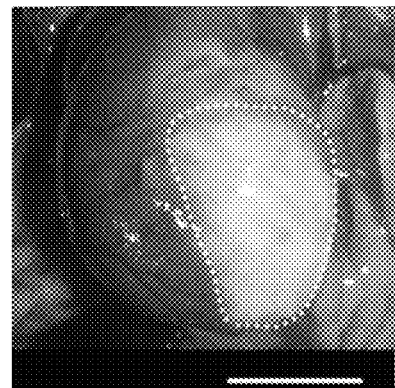
(FIG. 28A) Macroscopic and (FIG. 28B) histologic images 8 wk following hydrogel injection.
Figure 28B:
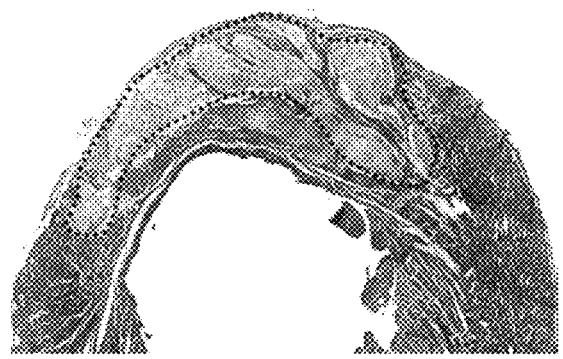
(FIG. 28B) Black dots trace the remnant hydrogel in the LV wall stained with H&E. Scale bar: 5 mm in (FIG. 28A), 500 um in (FIG. 28B).

Of particular note, the (80/10/10) had a tensile strength of 90 kPa, approximately 14× higher than poly(NIPAAm-co-AAc-co-HEMAPTMC), a 20% modulus of 100 kPa, and elongations at break >1000%. In vitro degradation in aqueous buffer required 6 months. This hydrogel was injected in the rat chronic infarction model in a pilot study. After 8 weeks, the hydrogel completely covered the infarcted myocardium (FIG. 28A), and was observed histologically with substantial cellular infiltration. The wall thickness of the injected area approximated residual healthy myocardium (FIG. 28B).

Discussion

NIPAAm based thermally responsive and bioabsorbable hydrogels have been extensively investigated as injectable materials for applications in regenerative medicine including as temporary matrices to facilitate localized cell and drug delivery (Ruel-Gariepy, E.; Leroux, J. C. Eur. J. Pharm. Biopharm. 2004, 58, 409-426; Jeong, B.; Kim, S. W.; Ba, Y. H. Adv. Drug. Deliv. Rev. 2002, 54, 37-51; Klouda, L.; Mikos, A. G. Eur. J. Pharm. Biopharm. 2008, 68, 34-45; Stile, R. A.; Burghardt, W. R.; Healy, K. E. Macromolecules 1999, 32, 7370-7379; Qiu, Y.; Park, K. Adv. Drug. Deliv. Rev. 2001, 53, 321-339; Gil, E. S.; Hudson, S. M. Prog. Polym. Sci. 2004, 29, 1173-1222; and Peppas, N. A.; Kim, B. J. Drug Del. Sci. Tech. 2006, 16, 11-18). Injectable biomaterials are also increasingly of interest as bulking agents to provide mechanical support in failing, traumatized and diseased tissues, such as urinary sphincters for urinary incontinence (Appell, R. A. Urol. Clin. North. Am. 1994, 21, 177-82 and Ghoniem, G. M.; Elsergany, R.; Lewis, V. Urol. Nurs. 1998, 18, 125-128), nucleus pulposus for degenerative disc disease (Vernengo, J.; Fussell, G. W.; Smith, N. G.; Lowman, A. M. J. Biomed. Mater. Res. B 2008, 84, 64-69 and Cloyd, J. M.; Malhotra, N. R.; Weng, L.; Chen, W.; Mauck, R. L.; Elliott, D. M. Eur. Spine. 12007, 16, 1892-1898), and the cardiac wall for ischemic cardiomyopathy (Wall, S. T.; Walker, J. C.; Healy, K. E.; Ratcliffe, M. B.; Guccione, J. M. Circulation 2006, 114, 2627-2635). For mechanical support applications, fewer investigations have been performed evaluating NIPAAm-based materials. One area where there has been notable recent interest has been in cardiac wall injection therapy (Fujimoto, K. L.; Ma, Z.; Nelson, D. M.; Hashizume, R.; Guan, J.; Tobita, K.; Wagner, W. R. *Biomaterials* 2009, 30, 4357-4368 and Wang, T.; Wu, D.; Jiang, X.; Zhang, X.; Li, X.; Zhang, J.; Zheng, Z.; Zhuo, R.; Jiang, H.; Huang, C. *Eur. J. Heart Fail* 2009, 11, 14-19).

Although naturally derived materials including alginate (Landa, N.; Miller, L.; Feinberg, M. S.; Holbova, R.; Shachar, M.; Freeman, I.; Cohen, S.; Leor, J. *Circulation* 2008, 117, 1388-1396), fibrin (Christman, K. L.; Fok, H. H.; Sievers, R. E.; Fang, Q. H.; Lee, R. J. *Tissue Eng.* 2004, 10, 403-409 and Huang, N. F.; Yu, J.; Sievers, R.; Li, S.; Lee, R. J. *Tissue Eng.* 2005, 11, 1860-1866), alginate-fibrin composites (Mukherjee, R.; Zavadzkas, J. A.; Saunders, S. M.; McLean, J. E.; Jeffords, L. B.; Beck, C.; Stroud, R. E.; Leone, A. M.; Koval, C. N.; Rivers, W. T.; Basu, S.; Sheehy, A.; Michal, G.; Spinale, F. G. *Ann. Thorac. Surg.* 2008, 86, 1268-1277), collagen (Huang, N. F.; Yu, J.; Sievers, R.; Li, S.; Lee, R. J. *Tissue Eng.* 2005, 11, 1860-1866), chitosan (Lu, W.; Lu, S.; Wang, H.; Li, D.; Duan, C.; Liu, Z.; Hao, T.; He, W.; Xu, B.; Fu, Q.; Song, Y.; Xie, X.; Wang, C. *Tissue Eng.* 2009, 15, 1437-1447) and self-assembling peptides (Davis, M. E.; Motion, J. P.; Narmoneva, D. A.; Takahashi, T.; Hakuno, D.; Kamm, R. D.; Zhang, S.; Lee, R. T. Circulation 2005, 111, 442-450 and Davis, M. E.; Hsieh, P. C.; Takahashi, T.; Song, Q.; Zhang, S.; Kamm, R. D.; Grodzinsky, A. J.; Anversa, P.; Lee, R. T. *Proc. Natl. Acad. Sci. USA* 2006, 103, 8155-8160) have been tried with different degrees of beneficial effects observed, synthetic injectable hydrogels have the advantage of being well defined in chemical structure and thus amenable to manipulation on the molecular level to achieve desired properties such as a increased mechanical strength and a targeted degradation profile. Appropriate control of these functional parameters may result in improved outcomes in the post-infarction cardiac wall remodeling process.

One of our previously developed thermoresponsive and biodegradable hydrogels, poly(NIPAAm-co-AAc-co-Acryloxysuccinimide-co-HEMAPLA) (Guan, J.; Hong, Y.; Ma, Z. Wagner W R. Biomacromolecules 2008, 9, 1283-92), was found to degrade too fast (2 days in vivo), making it non-ideal for in vivo application. A more recently developed hydrogel poly(NIPAAm-co-AAc-co-HEMAPTMC) showed much slower degradation process (80% mass loss in 4 month in PBS) and was demonstrated to produce beneficial effect in altering the post-infarction remodeling and heart failure process in a rat model (Fujimoto, K. L.; Ma, Z.; Nelson, D. M.; Hashizume, R.; Guan, J.; Tobita, K.; Wagner, W. R. *Biomaterials* 2009, 30, 4357-4368). A drawback of this hydrogel, however, is that it has a pH-sensitive mechanical strength. Although the hydrogel has a tensile strength of 6 kPa at pH 3.6, at physiologic neutral pH value (7.4) the hydrogel is weakened. The mechanism for this weakening is the deprotonation of the AAc carboxyl groups, resulting in increased hydration at neutral pH, and weakening of the hydrophobic interactions between polymer chains that contributed to the mechanical strength. Utilization of the monomer AAc, however, is necessary for the hydrogel to be bio-absorbable. Without AAc to increase polymer hydrophilicity, cleavage of the PTMC residues to reveal HEMA does not increase the copolymer's hydrophilicity adequately to make the copolymer soluble at 37° C. (Fujimoto, K. L.; Ma, Z.; Nelson, D. M.; Hashizume, R.; Guan, J.; Tobita, K.; Wagner, W. R. Biomaterials 2009, 30, 4357-4368), because there are no charged residues produced on the polymer chains upon the hydrolysis of the degradable side chains of the HEMA-based biodegradable monomers (Cui, Z.; Lee, B. H.; Vernon, B. L. Biomacromolecules 2007, 8, 1280-1286).

In this Example, a novel biodegradable monomer, MAPLA, was designed and synthesized (FIG. 14). This monomer generates highly hydrophilic carboxylate groups upon hydrolytic cleavage of the PLA residues, making the copolymer adequately hydrophilic to allow dissolution with appropriate co-monomers other than AAc. Random copolymers of poly(NIPAAm-co-HEMA-co-MAPLA) formed thermoresponsive biodegradable hydrogels of relatively high mechanical strength at neutral pH (FIG. 22).

The ratio of the biodegradable monomer MAPLA in the hydrogel needs to be controlled for the hydrogel to be both bioabsorbable and injectable. First, the MAPLA contents must be high enough in the copolymer so that there can be enough carboxylate groups produced after cleavage of the PLA residues to achieve copolymer solubilization at 37° C. On the other hand, since MAPLA is a hydrophobic monomer, too high of an MAPLA content before cleavage will make the copolymer insoluble in aqueous solution even at low temperature. This effect is also seen in the increase in the viscosity of the copolymer solution with increasing MAPLA content (FIG. 21). A high viscosity will make hydrogel injection difficult, particularly in the ease of cardiac injection therapy where very small diameter needles (23G or smaller) are desirable for injection to minimize tissue trauma and bleeding risk. In results not presented, it was found that if the feed ratio of MAPLA was 12%, the copolymer (78/10/12) could not be completely solubilized at 5° C. and the resulting viscous cloudy mixture was not able to be injected through a 23G needle. Therefore, in this work, poly(NIPAAm-co-HEMA-co-MAPLA) with monomer ratios of 84/10/6, 82/10/8 and 80/10/10 were synthesized and characterized.

Figure 18B:
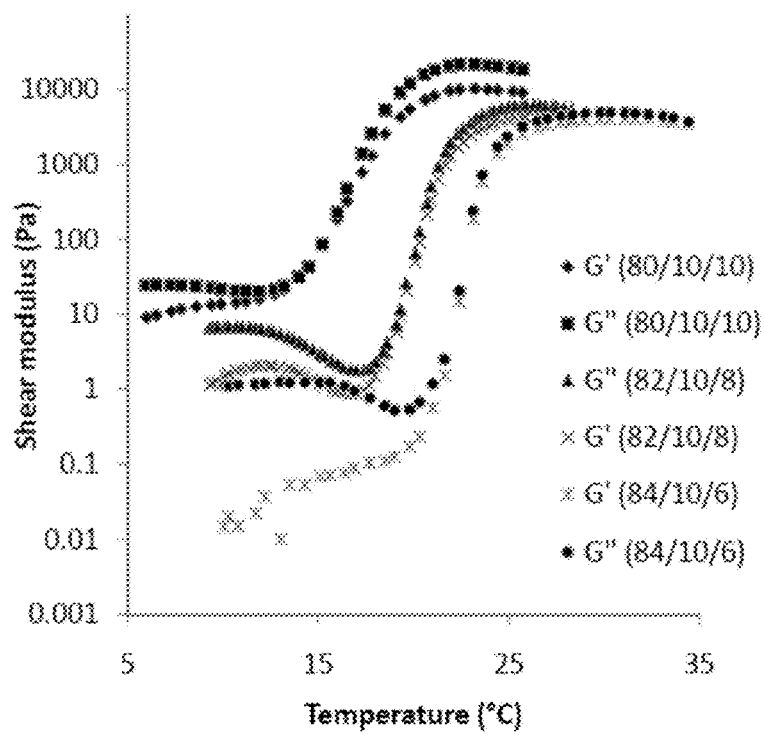
Figure 18C:
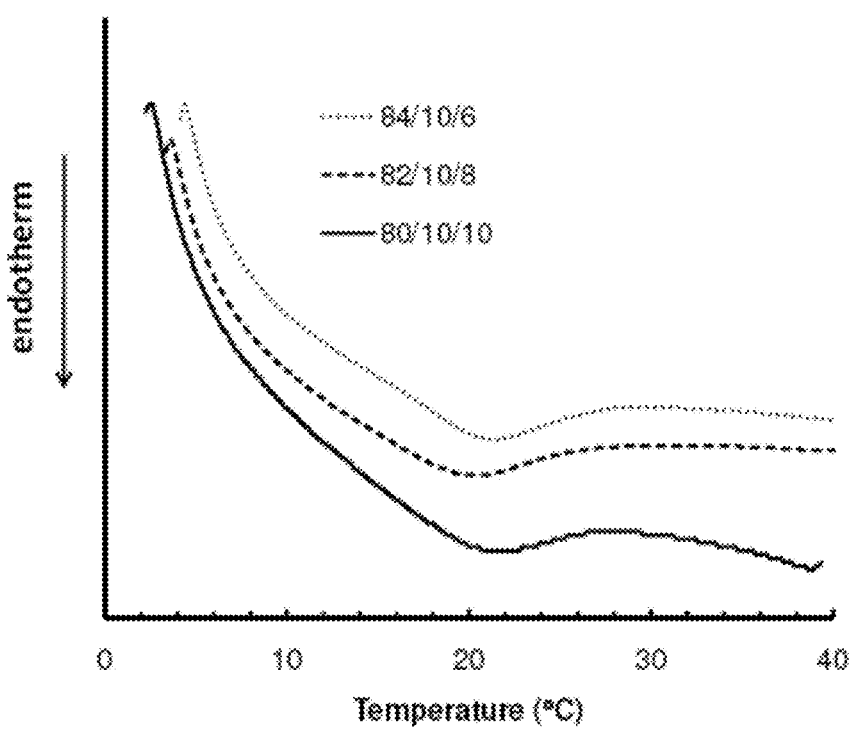

All three of the synthesized copolymers readily formed solutions in PBS at 5° C. and formed opaque solid hydrogels when the temperature was increased above 37° C. The LCST of the hydrogels increased with MAPLA content due to the enhanced hydrophobicity, as shown by optical and mechanical property analysis (FIGS. 18A and 18B). This trend, however, was not observed in the DSC analysis (FIG. 18C). It is noteworthy that LCSTs measured by different methods can vary due to differing definitions of the LCST. The LCSTs measured by mechanical property change (16, 20, 22° C. as shown in FIG. 18B) were higher than those measured optically (as shown Table 3), while the DSC curves of the three hydrogels showed broad endothermal peaks centered around 22, 21 and 22° C., respectively. Optical absorption of the hydrogel solution jumps when micelles are formed in the solution at a certain temperature to give a considerable amount of light scattering, while for mechanical analysis a higher transition temperature is necessary for a load-bearing 3-D gel network to be formed. In DSC analysis, the endothermal peaks appear when the temperature is high enough to induce the endothermal process of hydrogen bond breaking in the ice-like water molecule clusters around the hydrophobic domains and between the water molecules and amide bonds in the copolymers, together with the collapsing of the molecules from coils into globules (Rzaev, Z. M. O.; Dinc-er, S.; Pis-kin, E. *Prog. Polym. Sci.* 2007, 32, 534-595; Tian, J.; Seery, T. A. P.; Weiss, R. A. *Macromolecules* 2004, 37, 9994-10000; and Bae, Y. H.; Kim, S. W. *Polymeric materials encyclopedia: F-G, Volume* 4, edited by Salamone, J. C. CRC Press, pp. 3492).

Although the LCST-based transition of the NIPAAm-based polymer is a first-order thermodynamic transition, experimentally it is often observed as a slowly occurring continuous transition controlled by the kinetics of water diffusion out of the gel. In this work, the gelation of the three hydrogels at 37° C. also appeared as a slow process in which the polymer chains collapsed and the water diffused out of the hydrogel gradually until the hydrogels stabilized at smaller volumes (FIG. 19) with final water contents of ~45% (Table 3). The hydrogels therefore exhibited different microstructures during the gelation process, in which a relatively uniform and loose structure was found at the beginning (30 sec), while the final hydrogel formed had a much more condensed polymer phase, as shown by SEM micrographs (FIG. 19). The hydrogels containing higher MAPLA content had stronger hydrophobic interactions between molecular chains and faster polymer collapsing and water exclusion rates, as characterized by plotting the water content of the hydrogels as a function of incubation time (FIG. 20). Also due to the stronger hydrophobic interactions, the hydrogel with a higher MAPLA content showed stronger tensile and shear mechanical strength (FIGS. 22 and 23).

Figure 25:
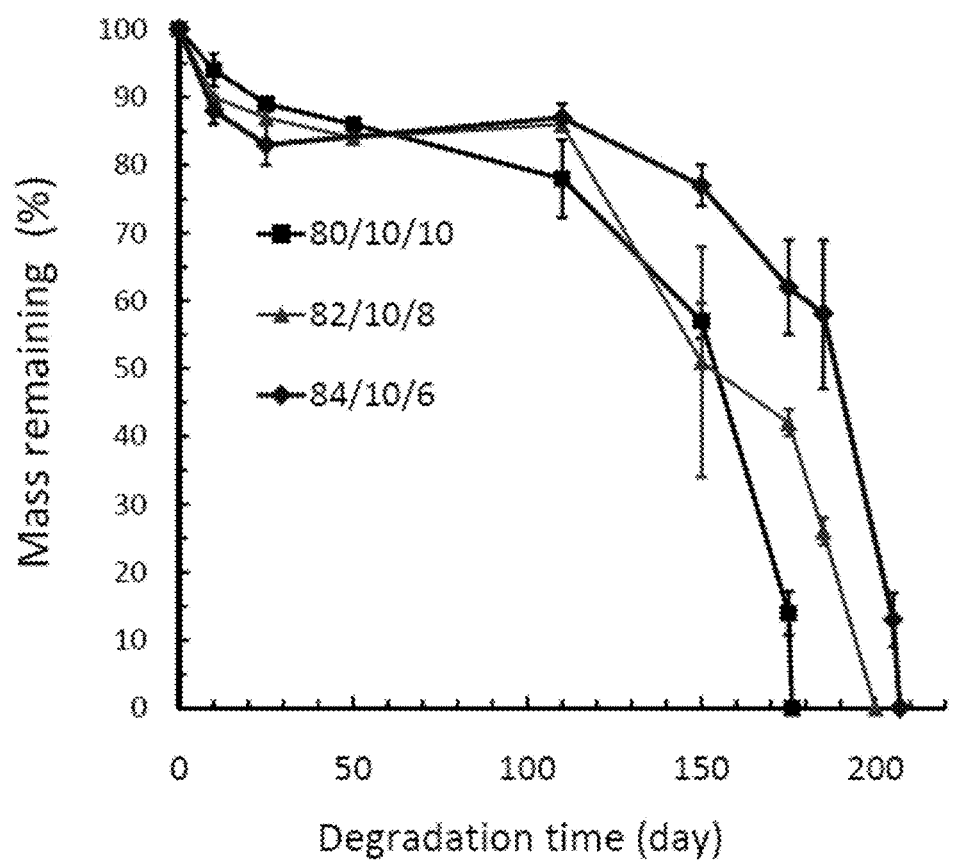
FIG. 25. Mass loss curves of poly(NIPAAm-co-HEMA-co-MAPLA) hydrogels in PBS at 37° C.

Upon removal of the PLA side chains by hydrolysis, all three copolymers became soluble at 37° C. (LCST >37° C.), verified both by the fast degradation study in 1M NaOH, and by degradation under more physiological conditions in PBS at 37° C. over a period of 8 months (FIG. 25). The degradation curves shown in FIG. 25 all followed the same pattern, in which an initial "burst" mass loss of ~10-20% over the first 3 weeks occurred, followed by ~3 months with almost no mass change, and then followed by an accelerated mass loss process over ~3 months until the hydrogels were completely dissolved. The accelerated degradation in the latter stage could be explained by positive feedback between PLA ester bond cleavage leading to increased copolymer hydrophilicity, leading to increased water content to facilitate further ester bond cleavage (Cui, Z.; Lee, B. H.; Vernon, B. L. *Biomacromolecules* 2007, 8, 1280-1286). The initial mass loss was possibly caused by the dissolution of the lower molecular weight fractions in the copolymers, while the main mass loss occurred only after enough carboxylate groups were produced by PLA side chain cleavage. The degradation rate of the hydrogel was found to be influenced by the MAPLA feed ratio. A higher MAPLA feed ratio means more carboxylate groups can be produced in the degradation process so the copolymer can be dissolved faster, while hydrogels containing less MAPLA must wait longer time for enough carboxylate to be produced. Interestingly, the initial mass loss speed of the hydrogels decreased with the increasing MAPLA content in the hydrogel, due to the fact that hydrogel with more MAPLA is more hydrophobic before degradation, slowing down the water diffusion into the hydrogel and the diffusion and dissolution of the low molecular weight fractions of the copolymer. This trend in rates reverses for the latter stage, which can be explained by the relative availability of carboxylates.

The thermally responsive hydrogels showed no negative effects on the metabolic activity and live/dead ratio of the cells (RSMC) that were co-cultured with hydrogel degradation products (FIGS. 26 and 27), confirming the potential applicability of the material for cardiac injection therapy and possibly for cell or drug delivery. A limitation of the material as a cell delivery carrier, however, is that the hydrogel contains only ~45% water at 37° C. (Table 3). With lower diffusion rates of water and nutrients likely for a denser material, this hydrogel may not provide a hospitable environment for long term cell culture. Although simple inclusion of hydrophilic monomers into the copolymer can increase the water content and improve the cell encapsulation suitability, it can also decrease the hydrophobic interactions between the molecular chains and compromise the mechanical strength of the material. The trade-off between these properties can be dictated by the planned application. In the cardiac biomaterial injection literature it is clear that the injection of acellular materials is associated with improved functional outcomes (Jiang, X. J.; Wang, T.; Li, X. Y.; Wu, D. Q.; Zheng, Z. B.; Zhang, J. F.; Chen, J. L.; Peng, B.; Jiang, H.; Huang, C.; Zhang, X. Z. *J. Biomed. Mater. Res. A* 2009, 90, 472-477 and Yu, J.; Christman, K. L.; Chin, E.; Sievers, R. E.; Saeed, M.; Lee, R. J. *J. Thorac. Cardiovasc. Surg.* 2009, 137, 180-187), so cell survival in the early stages of injection may not be critical and cell migration into a looser injected material following a period of in situ degradation may be appropriate.

Example 3

Synthesis of NIPAAm-based Random and Block Copolymers as Biodegradable Thermally Responsive Hydrogels (HEMAPTMC and HEMAPLA)

An ABA type block copolymer where A=poly(NIPAAm-co-HEMA-co-MAPLA) (80/10/10) and B=polyethylene glycol (PEG) was synthesized by atom transfer radical polymerization (ATRP). Molecular weight of the A and B blocks can be controlled to obtain hydrogels with different water content and mechanical properties. These hydrogels have potentials to be applied for injection therapy of ischemic cardiomyopathy to alter adverse remodelling and preserve cardiac function post-infarction.

Specifically, ABA type block copolymers were synthesized by ATRP. First, α-bromisobutyric acid PEG ester (BBPEG) was synthesized by reacting one of three PEGs (1, 6 or 20 kD) and α-bromoisobutyryl bromide. NIPAAm, HEMA and MAPLA were copolymerized for 24 h in methanol containing BBPEG, CuCl and the ligand 1,4,8,11-tetramethyl-1,4,8,11-tetraazacyclotetradecane with a molar ratio of 1:2:2.

Polymer structures were confirmed by NMR and FTIR. Hydrogel thermally induced sol-gel transitions and the mechanical properties were studied rheometry. 20 kD A blocks were combined with PEG blocks of 1, 6 and 20 kD. With a 20 kD PEG block, the polymer solution showed increased viscosity and formed gels with negligible water exclusion at 37° C. Copolymers with low B/A mass ratios showed hydrogel formation with water exclusion, behaving similarly to A-type hydrogels.

In conclusion, a family of NIPAAm-based block copolymers were synthesized. By manipulating the molecular design, it was possible to vary a number of key parameters important for injectable biomaterial design, including: viscosity below the transition temperature, gelation speed, gel mechanical strength, final water content, and degradation rate. Depending upon the area of application and hypothesized needs, these materials might be applied as temporary tissue bulking agents, injectable carriers for cell therapy, or as local reservoirs for controlled release.

Example 4

Figure 29:
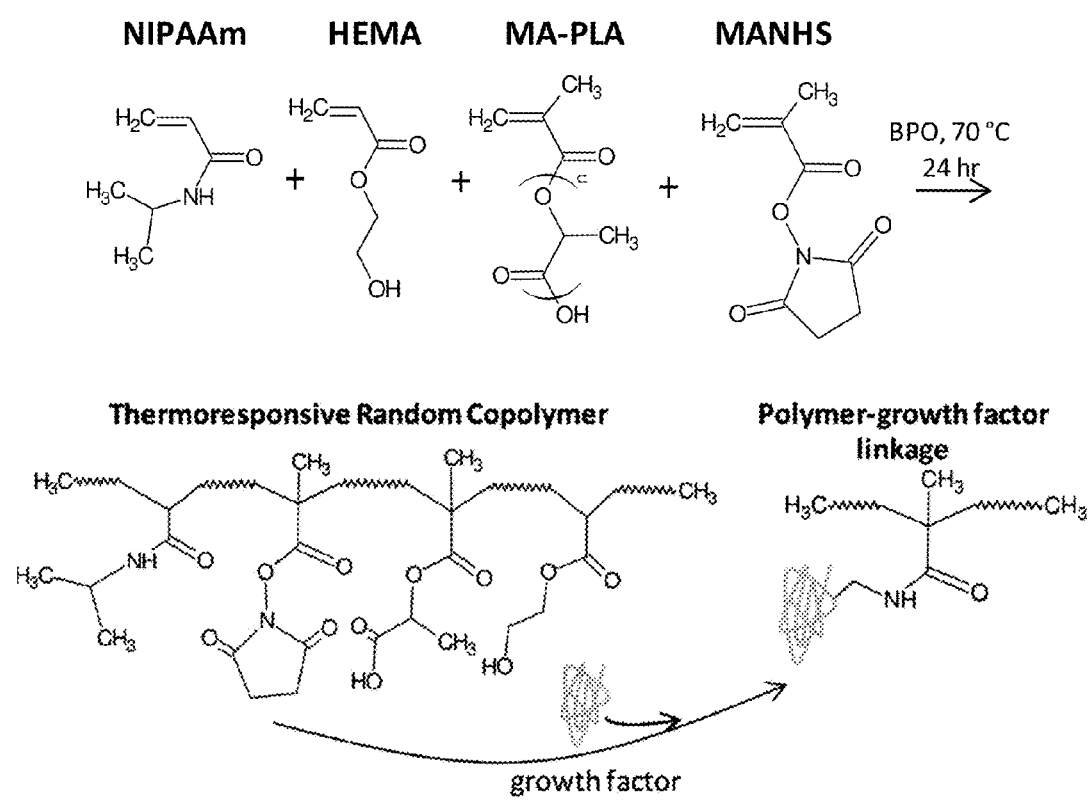
FIG. 29. Synthesis of poly(NIPAAm-co-HEMA-co-MANHS-co-MAPLA) and subsequent reaction of the MANHS mer with growth factor.

Design Rationale and Characterization of Poly (NIPAAm-Co-HEMA-Co-MANHS-co-MAPLA)+/− growth factors In order to provide the capacity for controlled release of bioactive factors from the injected hydrogels, the design of poly(NIPAAm-co-HEMA-co-MAPLA was modified to create poly(NIPAAm-co-HEMA-co-MANHS-co-MAPLA by incorporating the monomer N-hydroxysuccinimide methacrylate (MANHS) (FIG. 29). This monomer has the ability to readily react with primary amine groups (e.g. surface lysines in proteins) forming a stable amide bond and provides a means for covalent growth factor attachment to the copolymer in an aqueous environment. The covalent link reduces the burst release often encountered with hydrogel systems. This attachment technique was applied in Wang F, et al. (Acta Biomaterialia (published online). doi: 10.1016/j.actbio.2009.12.011), where poly(NIPAAm-co-AAc-co-HEMAPTMC) was used but with the addition of N-acryloxy succinimide (NAS) to bind IGF-1. The results showed IGF-1 was successfully bound to the hydrogel and remained bioactive upon release. As discussed, however, poly(NIPAAm-co-AAc-co-HEMAPTMC) does not have the mechanical strength and decreased degradation rate advantages of poly (NIPAAm-co-HEMA-co-MAPLA). We will also switch to MANHS over NAS since the succinimide ester reactivity with water is slower for MANHS, ultimately favoring amine reaction and higher loading efficiency. In preliminary studies 1 mol % MANHS has been incorporated in the polymer feed to make poly(NIPAAm-co-HEMA-co-MANHS-co-MAPLA) (Mw 25 kD, Mw/Mn ~1.5) that was subsequently loaded with protein at a loading efficiency of 46%. The majority of protein was delivered in vitro from poly(NIPAAm-co-HEMA-co-MANHS-co-MAPLA) in the first week followed by near zero-order release extending for 3 months related to polymer degradation. Because we ultimately seek a hydrogel system with bi-modal release, with bFGF delivery occurring before IGF-1, we will take advantage of the higher early release rates and use this covalent attachment system with bFGF.

Several design parameters of poly(NIPAAm-co-HEMA-co-MANHS-co-MAPLA) can be altered to influence protein release kinetics. In one example, the relative amount of MANHS incorporated into the copolymer, which determines protein binding capacity, is varied between 1-5 mol %. Increasing MANHS content not only has the potential to increase protein binding but can also be used to speed polymer degradation and thus protein delivery rate. In addition to this parameter the amount of bFGF loaded can be varied. Both parameters will influence the release profile of the protein. While studies to date have not specifically investigated the influence that burst release has on the angiogenic effects of delivered bFGF, some conclusions can be made based on direct injection studies. It has been shown that when a solution of free bFGF is injected directly into the myocardium only 16% remains after one hour (Sakakibara Y, et al. Eur J Cardiothorac Surg 2003; 24:105-11. PMID: 12853053). While some cardiac improvements have been shown from this delivery method, additional benefits of bFGF delivery with a carrier have been demonstrated (Shao Z Q, et al. Circ J 2006; 70:471-7. PMID: 16565567 and Iwakura A, et al. Heart Vessels. 2003 May; 18(2):93-9. PMID: 12756606). Delivery of bFGF from microspheres and gel systems over a range of 1-6 wk resulted in substantial vascular and functional improvements (Sakakibara Y, et al. Eur J Cardiothorac Surg 2003; 24:105-11. PMID: 12853053; Iwakura A, et al. Heart Vessels. 2003 May; 18(2):93-9. PMID: 12756606; and Tabata Y, et al. Biomaterials 1998; 19:1781-9. PMID: 9856589). The amount of bFGF remaining at the injection site 72 h after injection was roughly 30% when the factor was incorporated into gelatin microspheres—a 15× increase compared to free bFGF injection. As an example, the design of poly(NIPAAm-co-HEMA-co-MANHS-co-MAPLA) is manipulated with the objective of >70% release over the first 2 wk, with continued delivery for at least 6 wk.

Studies have also shown that improvements to cardiac function and blood flow in rats can be elicited when between 10 and 100 µg of bFGF is delivered, providing an exemplary range of bFGF loading concentrations that can be characterized in vitro (Shao Z Q, et al. Circ J 2006; 70:471-7. PMID: 16565567 and Sakakibara Y, et al. Eur J Cardiothorac Surg 2003; 24:105-11. PMID: 12853053). While there is concern that excessive bFGF delivery might lead to hemangioma formation, bFGF administration in this range has not been associated with this complication in animal studies.

In another example microparticle carriers, which offer an extended release profile, are employed as a protein delivery mechanism. Combining a suspension of growth factor-loaded (or other active agent-loaded) microparticles in solution with the protein-conjugated poly(NIPAAm-co-HEMA-co-MANHS-co-MAPLA) permits delivery of a second growth factor, where each delivery system—covalent hydrogel attachment or microparticulate—has distinct design parameters to influence release kinetics which are largely independent of the other. Microparticles of many common biomaterials such as gelatin, collagen, alginate, and poly(lactic-co-glycolic) acid (PLGA) have been synthesized and used for drug delivery with positive results (Kobsa S, et al. Pediatr Res 2008; 63:513-9. PMID: 18427296). With poly(NIPAAm-co-HEMA-co-MANHS-co-MAPLA). In an example, relatively hydrophobic PLGA microparticles are utilized since they will interact with the hydrophobic NIPAAm groups in the collapsed hydrogel, thus precluding their exclusion from the gel network during phase transition. As an example, a double emulsion system is used to form these microparticles with IGF-1 loading in a manner to protect against protein denaturation, as previously described (Singh M, et al. J Control Release 2001; 70:21-8. PMID: 11166404). We have shown that appropriately designed microparticles can deliver growth factor at a slower rate with a smaller burst than the covalent system above. PLGA (75:25, 100 kDa) microparticles (49 um diam) encapsulating BSA have been synthesized and protein release rates measured after particle mixing with poly (NIPAAm-co-HEMA-co-MAPLA). Inclusion of protein-loaded PLGA microparticles in a hydrogel system has previously been shown to nearly eliminate burst release leading to delayed protein delivery (Defail A J, et al. J Biomed Mater Res A 2006; 79:954-62. PMID: 16941588). Our results agree, showing only 4% burst release of total protein during gel formation, and only 15% released by 2 wk. This release rate is about one-third of that from the same microparticles not within a hydrogel. Later-stage protein release follows the degradation of the PLGA microparticles which increases after 4 wk in saline. A biphasic system is thus achievable wherein the majority of bFGF is released early from the hydrogel carrier followed by IGF-1 release later as the PLGA microparticles within the gel degrade. As has been shown previously, the burst and duration of protein release from PLGA microparticles can fall within a wide range depending on controllable factors such as polymer weight fraction in the microparticles, particle size, degradation time, and weight fraction of growth factor (Singh M, et al. J Control Release 2001; 70:21-8. PMID: 11166404 and Defail A J, et al. J Biomed Mater Res A 2006; 79:954-62. PMID: 16941588). One exemplary design objective for microparticles is <20% release in the first 2 wk, with an additional 60% over the 4 wk following. Since a dose range from 25 µg to 100 µg of IGF-1 has shown functional cardiac improvements in rats, a moderate total dose between 1-10 µg is used (Davis M E, et al. Proc Natl Acad Sci 2006; 103:8155-60. PMCID: PMC1472445 and Kanemitsu N, et al. J Heart Lung Transplant 2006; 25:1253-62. PMID: 17045939).

Hydrogel chemical structure is characterized with NMR, FTIR, and mass spectra. Molecular weight is determined by gel permeation chromatography. The LCST of the hydrogel solutions is determined by DSC, UV-optical absorption with temperature scanning and rheological testing with temperature scanning. Hydrogel solution viscosity below the LCST is measured with rheometry and gelation speed at 37° C. is quantified by plotting water content over time. Tensile and rheological testing provides hydrogel mechanical properties. Polymer degradation product cytotoxicity is assessed by the metabolic viability of cells cultured with medium supplemented with degradation products. Cells also are observed under fluorescence microscopy after live/dead staining when cultured atop the hydrogels. For controlled release from poly (NIPAAm-co-HEMA-co-MANHS-co-MAPLA), the attachment of bFGF to the polymer is investigated with matrix assisted laser desorption ionization (MALDI) mass spectrometry. Release kinetics of each growth factor from its polymer carrier is analyzed by enzyme-linked immunosorbant assay for the specified protein. To quantify bioactivity of the released bFGF and IGF-1 cell proliferation assays with L929 fibroblasts (Matsusaki M. et al. Biomacromolecules 2005; 6:3351-6. PMID: 16283765) and MG-63 (Singh M, et al. J Control Release 2001; 70:21-8. PMID: 11166404) cells are used, respectively with calibration to known growth factor concentrations. Failure to meet the stated design objectives for poly(NIPAAm-co-HEMA-co-MAPLA) and poly (NIPAAm-co-HEMA-co-MANHS-co-MAPLA) results in iterative material design refinement and characterization using the controllable parameters discussed above.

Example 5

Robotic Delivery of Hydrogel Compositions

The HeartLander tethered crawler consists of 2 bodies (front and rear) that each contain an independent suction pad for prehension of the epicardium using suction (Ota T, Patronik N A, Schwartzman D, Riviere C N, Zenati M A. Minimally invasive epicardial injection using a novel semi-autonomous robotic device. Circulation 2008; 118:S115-S120. doi:10.1161/CIRCULATIONAHA.107.756049). Each crawler body is 5.5×8×8 mm and is fabricated using stereolithography. These dimensions include a 2 mm diameter working channel and allow the robot to fit through an 8 mm diameter port. The drive transmission of the crawler is comprised of 2 superelastic nitinol wires (0.3 mm diameter) attached to the front body and sheathed within low-friction plastic tubes that are attached to the rear body. The wires slide freely within the plastic sheaths when driven by the motors located in a tabletop instrumentation system, controlling the distance and angle between the crawler bodies. Locomotion of the HeartLander crawler is a cyclic, inchworm-like process that is coordinated through a computer control system by regulating the wire lengths between the crawler bodies and the vacuum pressure in the corresponding suction pads. To move forward, the wires are extended to advance the front body while the rear body is under active suction. Retracting the wires after active suction has been transferred to the front body then causes the rear body to advance toward the front body. To move backward, this process is reversed. Turning is achieved by advancing the drive wires in different lengths to achieve the desired heading orientation. This low-level coordination is maintained by the computer control system, and thus the details are transparent to the surgeon. In experiments in vivo in a porcine model, HeartLander has demonstrated the ability to navigate to anterior, lateral, and posterior surfaces of the epicardium, and has performed myocardial injections of marker dye with position error of 1.7±1.0 mm (Patronik N A, et al. IEEE Transactions on Robotics 2009; 25(5):1109-1124. doi: 10.1109/TRO.2009.2027375).

The primary challenge in adapting the HeartLander system for hydrogel injection is to keep the hydrogel cool inside the injection tubing until it is injected into the myocardium. To accomplish this, a specialized jacketed needle is constructed that is cooled via liquid-metal phase transition. An initial prototype has been constructed using elemental gallium, as a check of feasibility. To achieve phase transition at the right temperature, the cooling jacket for the needle is constructed using eutectic gallium-indium (EGaIn) (Dickey M D, et al. Adv Funct Mater 2008; 18:1097-1104. doi: 10.1002/adfm.200701216). In case of need, an alternative technology is a thermoelectric cooler (Volklein F, et al. Sens Actuators A Phys 1999; 75(2):95-101. doi:10.1016/S0924-4247(99) 00002-3). Hydrogel in the syringe (within the tabletop instrumentation) and the tubing that feeds the needle will be kept cool using localized refrigeration and insulation as appropriate. The cooled injection system design will be tested in vitro using a water bath with artificial media, as well as porcine hearts from the abattoir. After design refinement the system is used to perform porcine hydrogel injections with the hydrogels described in Example 4.

Example 6

Evaluation of Thermoreponsive Hydrogel Function In vivo

For initial functional assessment of the hydrogels of Example 4 (+/−growth factors), an established rat chronic infarction model is used (Fujimoto K L, et al. J Am Coll Cardiol 2007; 49: 2292-300. PMID: 17560295 and Fujimoto K L, et al. Biomaterials 2009; 30:4357-68. PMID: 19487021). Hydrogel will be injected into the infarcted myocardium 2 wk post-MI (infarction center and border regions). Outcome assessments are compared between hydrogel-injected rats and PBS-injected control animals, as well as temporally within groups, are summarized in Table 4. Three post-injection time points are evaluated to allow evaluation of early remodeling (4 wk), comparison to our current standard (8 wk) and a relatively long time point for effect duration (16 wk).

TABLE 4

Overview of in vivo assessment approach and methods

| | |
|---|---|
| Cardiac function & wall dimensions | longitudinal echocardiography, dobutamine stress echocardiography, ventricular pressure-volume measurement, hematoxylin & eosin section measurements and biochemical assays (Western blot and RT-PCR) |
| Histology (immunohistochemistry) | |
| Vascular cell identification | α-smooth muscle actin, CD31, von-Willebrand factor |
| Contractile smooth muscle | caldesmon, calponin, smooth muscle myosin heavy chain 2 (SMMHC-2), SM-22α |
| Cellular apoptosis | TUNEL staining, active caspase-3 |
| Cellular proliferation | Ki67, phospho-histone H3 |
| Cardiomyocyte identification | Nkx2.5, GATA4, α-sarcomeric actin, α- and β-cardiac myosin heavy chains, cardiac troponin-T, and -I, and connexin 43 |

TABLE 4-continued

Overview of in vivo assessment approach and methods

| bFGF and IGF-1 delivery | human-specific bFGF and IGF-1 |
| Regional myocardial compliance | passive inflation testing in situ |

Based on the successful results of poly(NIPAAm-co-AAc-co-HEMAPTMC) in the rat model it is ready to move to the more clinically relevant porcine model and to be coupled with the HeartLander system modified for gel injection. In that experiment, a porcine chronic LV myocardial ischemia/reperfusion injury model is used, which is created by balloon occlusion of the left coronary circumferential branch for 60 min. We have substantial experience in creating this model under imaging in pigs and assessing the MI with echocardiography. Using the modified HeartLander system, hydrogel or PBS injection is performed 2 wk post-MI through a small subxiphoid incision. Based on our current results in rats, an end point 8 wk post-injection is used for the porcine model. A longer time point will ultimately be desirable, but at this stage we seek to demonstrate the effect in the large animal model to justify moving to a more extended evaluation of effects several months after injection with the most promising hydrogel. Outcome assessments will be similar to those for the rat model with some constraints on cross-reactive monoclonal antibodies.

LV function is assessed using non-invasive echocardiography and standard M-mode and 2-D measures of diastolic and systolic dimensions, wall thickness, motion, and function for healthy and infarct zones. End-diastolic area (EDA) and end-systolic area (ESA) of the LV cavity is measured by endocardial planimetery. Total and regional LV fractional area change (FAC) are calculated as [(LVEDA-LVESA)/LVEDA]×100%. The timeline for echo assessment in control and hydrogel treated rats is prior to coronary ligation, t=0 (hydrogel injection), and t=4, 8, and 16 wk after hydrogel injection. Invasive measures of LV performance are completed at t=0, 4, 8 and 16 wk prior to euthanasia for histologic assessment. Simultaneous LV pressure (with a pressure-transducer tip Millar catheter) and transthoracic echo data are acquired to calculate EDP, $P_{max}$, $+dP/dt_{max}$, $-dP/dt_{max}$, and tau. Regional myocardial function and functional reserve is assessed with combined dobutamine stress echocardiography and LV pressure measurements. In our preliminary studies we have found that dobutamine infusion did not influence heart rate, LV pressure or FAC in infarcted rats. We expect that effective hydrogel injection will lead to an increase in the functional reserve of the myocardium in treated rats. At experiment termination, passive LV inflation is performed to quantify regional myocardial compliance in the infarction zone using a videography method to track displacement of placed landmarks that we have previously employed (Fujimoto K L, et al. J Am Coll Cardiol 2007; 49: 2292-300. PMID: 17560295). This technique will allow assessment of hydrogel injection effects both when the hydrogel still remains in the wall as well as after it has been resorbed. We hypothesize that the remodeled LV wall will be softer after hydrogel treatment and after hydrogel resorbtion.

In vivo assessment of the efficacy of growth factor delivery from the hydrogels in the rat includes the functional and cellular responses outlined in Table 4, of particular note will be the vascular cell endpoints and markers of cellular proliferation. To detect bFGF and IGF-1 presence in myocardial sections, immunohistochemical staining will be performed. Heart tissue will also be collected from regions both in the infarct and border regions and homogenized to determine the bFGF and IGF-1 content with ELISA (Davis M E, et al. Proc Natl Acad Sci 2006; 103:8155-60. PMCID: PMC1472445).

The present invention has been described with reference to certain exemplary embodiments, dispersible compositions and uses thereof. However, it will be recognized by those of ordinary skill in the art that various substitutions, modifications or combinations of any of the exemplary embodiments may be made without departing from the spirit and scope of the invention. Thus, the invention is not limited by the description of the exemplary embodiments, but rather by the appended claims as originally filed.

We claim:

1. A composition, comprising a copolymer having a Lower Critical Solution Temperature (LCST) of less than 37° C., consisting essentially of N-alkyl acrylamide residues in which the alkyl is one of methyl, ethyl, propyl, isopropyl and cyclopropyl; hydroxyethylmethacrylate (HEMA) residues; and polylactide-methacrylate (MAPLA) macromer residues, wherein the MAPLA macromer residues have the following structure:

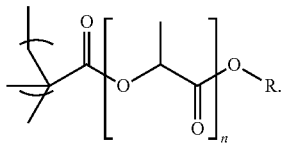

wherein R is H or $CH_3$ and n is from 1 to 10.

2. The composition of claim 1 prepared by radical polymerization of a mixture of N-alkyl acrylamide residues in which the alkyl is one of methyl, ethyl, propyl, isopropyl and cyclopropyl; hydroxyethylmethacrylate residues, and polylactide-methacrylate macromer residues.

3. The composition of claim 2 in which the polylactide-methacrylate macromer has an average lactide:methacrylate ratio of from 2:1 to 3:1.

4. The composition of claim 1 in which the N-alkyl acrylamide is N-isopropylacryamide (NIPAAm), the copolymer is prepared by radical polymerization, and the feed ratio of NIPAAm:MAPLA is 80-84:6-10.

5. The composition of claim 4 in which the feed ratio of NIPAAm:HEMA:MAPLA is 80-84:10:6-10.

6. The composition of claim 4 in which the feed ratio of NIPAAm:HEMA:MAPLA is one of 84:10:6, 82:10:8 and 80:10:10.

7. The composition of claim 1 in which the LCST of the copolymer is less than 20° C.

8. The composition of claim 1 in which the copolymer has an $M_n$ of between 20 kD and 35 kD.

9. The composition of claim 8 in which the copolymer has a polydispersity index of between 1 and 2.

10. The composition of claim 1 in which the copolymer further comprises residues comprising an amine-reactive group.

11. The composition of claim 10, in which the amine-reactive group is a succinimide group.

12. The composition of claim 10, in which the amine-reactive group is an oxysuccinimide group.

13. The composition of claim 10, in which the amine-reactive group is an isocyanate group.

14. The composition of claim 10, in which the residues comprising an amine-reactive group are N-acryloxy succinimide or N-hydroxysuccinimide methacrylate residues.

15. The composition of claim 1 in which the N-alkyl acrylamide is N-isopropylacrylamide (NIPAAM).

16. The composition of claim 1 in which the copolymer further comprises one or more polyethylene glycol blocks of between 0.5 and 25 kD.

17. The composition of claim 1, further comprising an active agent.

18. The composition of claim 17 in which the active agent is one or more of an antiseptic, an antibiotic, an analgesic, an anesthetic, a chemotherapeutic agent, a clotting agent, an anti-inflammatory agent, a metabolite, a cytokine, a chemoattractant, a hormone, a steroid, a protein and a nucleic acid.

19. The composition of claim 18 in which the active agent is one or both of basic fibroblast growth factor (bFGF) and insulin-like growth factor-1 (IGF-1).

20. The composition of claim 17 comprising microparticles comprising an active agent.

21. The composition of claim 20 in which the microparticles comprise one or more of gelatin, collagen, alginate, and poly(lactic-co-glycolic) acid (PLGA).

* * * * *